(12) United States Patent
Bobo et al.

(10) Patent No.: US 11,076,797 B2
(45) Date of Patent: Aug. 3, 2021

(54) SYSTEMS AND METHODS FOR THE IDENTIFICATION OF MEDICAL CONDITIONS, AND DETERMINATION OF APPROPRIATE THERAPIES, BY PASSIVELY DETECTING ACOUSTIC SIGNALS FROM CEREBRAL VASCULATURE

(71) Applicant: Cerenetex, Inc., Newport Beach, CA (US)

(72) Inventors: Benjamin William Bobo, Irvine, CA (US); David Robbins Asbury, Wildomar, CA (US); Devendra Goyal, Yorba Linda, CA (US); Mohsin Shah, Tustin, CA (US); John Chen, Tustin, CA (US); Sahar Bou-Ghazale Toukmaji, Irvine, CA (US)

(73) Assignee: Cerenetex, Inc., Newport Beach, CA (US)

( * ) Notice: Subject to any disclaimer, the term of this patent is extended or adjusted under 35 U.S.C. 154(b) by 47 days.

(21) Appl. No.: 16/380,841

(22) Filed: Apr. 10, 2019

(65) Prior Publication Data

US 2019/0307388 A1 Oct. 10, 2019

Related U.S. Application Data

(60) Provisional application No. 62/767,038, filed on Nov. 14, 2018, provisional application No. 62/655,752, filed on Apr. 10, 2018.

(51) Int. Cl.
*A61B 5/00* (2006.01)
*A61B 5/11* (2006.01)
(Continued)

(52) U.S. Cl.
CPC .......... *A61B 5/4064* (2013.01); *A61B 5/0022* (2013.01); *A61B 5/026* (2013.01);
(Continued)

(58) Field of Classification Search
CPC ..... A61B 5/026; A61B 5/6803; A61B 5/4082; A61B 5/4088; A61B 5/4094; A61B 5/165;
(Continued)

(56) References Cited

U.S. PATENT DOCUMENTS 4,008,711 A * 2/1977 Olinger ................. A61B 7/001
600/371
5,492,129 A * 2/1996 Greenberger ............ A61B 7/04
181/131

(Continued)

FOREIGN PATENT DOCUMENTS

AT        495791 T      2/2011
AT        527016 T     10/2011
(Continued)

OTHER PUBLICATIONS

Brennan et al., "An update on the blood vessel in migraine", Curr Opin Neurol. Jun. 2010; 23(3): 266-284. doi: 10.1097/WCO. 0b013e32833821c1.

(Continued)

*Primary Examiner* — Carl H Layno
*Assistant Examiner* — Anh-Khoa N Dinh
(74) *Attorney, Agent, or Firm* — Novel IP

(57) ABSTRACT

The present specification describes a system for diagnosing or screening one or more pathologies in a patient. The system includes a headset with at least one microphone or accelerometer to passively receive vibrations generated by the cerebral vasculature of the patient's brain, computing devices coupled with the headset for processing the received vibrations to obtain a unique signal, and a signal analyzer to analyze the signal in order to determine if the data includes patterns uniquely indicative of at least one of tension headaches, migraines, depression, dementia, Alzheimer's dis-
(Continued)

ease, epilepsy, Parkinson's disease, autism, cerebral vasospasm and meningitis.

24 Claims, 44 Drawing Sheets

(51) Int. Cl.
| A61B 5/026 | (2006.01) |
| A61B 5/16 | (2006.01) |
| A61B 7/00 | (2006.01) |
| A61B 7/04 | (2006.01) |
| G16H 40/67 | (2018.01) |
| G16H 40/20 | (2018.01) |

(52) U.S. Cl.
CPC ............ *A61B 5/1102* (2013.01); *A61B 5/165* (2013.01); *A61B 5/4082* (2013.01); *A61B 5/4088* (2013.01); *A61B 5/4094* (2013.01); *A61B 5/4824* (2013.01); *A61B 5/6803* (2013.01); *A61B 5/7264* (2013.01); *A61B 5/7282* (2013.01); *A61B 5/7405* (2013.01); *A61B 5/7445* (2013.01); *A61B 7/04* (2013.01); *A61B 2562/0204* (2013.01); *A61B 2562/0219* (2013.01); *A61B 2562/06* (2013.01)

(58) Field of Classification Search
CPC ... A61B 5/4064; A61B 5/1102; A61B 5/7405; A61B 5/7445; A61B 5/0022; A61B 5/7264; A61B 5/4824; A61B 5/7282; A61B 2562/0219; A61B 2562/06; A61B 2562/0204; A61B 7/04; A61B 7/001; A61B 8/0808; A61B 5/02; A61B 5/16; G16H 40/67; G16H 50/20
USPC .................................................. 600/586, 595
See application file for complete search history.

(56) References Cited

U.S. PATENT DOCUMENTS

| | | |
|---|---|---|
| 5,919,144 A | 7/1999 | Bridger |
| 6,491,647 B1 | 12/2002 | Bridger |
| 6,887,199 B2 | 5/2005 | Bridger |
| 7,720,530 B2 | 5/2010 | Causevic |
| 7,865,244 B2 | 1/2011 | Giftakis |
| 7,904,144 B2 | 3/2011 | Causevic |
| 7,945,316 B2 | 5/2011 | Giftakis |
| 8,041,418 B2 | 10/2011 | Giftakis |
| 8,041,419 B2 | 10/2011 | Giftakis |
| 8,068,911 B2 | 11/2011 | Giftakis |
| 8,108,038 B2 | 1/2012 | Giftakis |
| 8,108,046 B2 | 1/2012 | Giftakis |
| 8,112,148 B2 | 2/2012 | Giftakis |
| 8,112,153 B2 | 2/2012 | Giftakis |
| 8,209,009 B2 | 6/2012 | Giftakis |
| 8,209,019 B2 | 6/2012 | Giftakis |
| 8,214,035 B2 | 7/2012 | Giftakis |
| 8,239,030 B1 | 8/2012 | Hagedorn |
| 8,380,316 B2 | 2/2013 | Hagedorn |
| 8,473,024 B2 | 6/2013 | Causevic |
| 8,478,394 B2 | 7/2013 | Prichep |
| 8,485,979 B2 | 7/2013 | Giftakis |
| 8,744,562 B2 | 6/2014 | Giftakis |
| 8,761,868 B2 | 6/2014 | Giftakis |
| 8,792,974 B2 | 7/2014 | Rothman |
| 8,838,227 B2 | 9/2014 | Causevic |
| 8,838,247 B2 | 9/2014 | Hagedorn |
| 8,905,932 B2 | 12/2014 | Lovoi |
| 8,911,087 B2 | 12/2014 | Publicover |
| 8,938,301 B2 | 1/2015 | Hagedorn |
| 8,942,813 B1 | 1/2015 | Hagedorn |
| 8,948,860 B2 | 2/2015 | Causevic |
| 8,958,882 B1 | 2/2015 | Hagedorn |
| 8,989,836 B2 | 3/2015 | Machon |
| 9,165,472 B2 | 10/2015 | Hagedorn |
| D743,039 S | 11/2015 | Hagedorn |
| 9,198,587 B2 | 12/2015 | Rothman |
| 9,269,046 B2 | 2/2016 | Rothman |
| 9,282,930 B2 | 3/2016 | Machon |
| 9,477,813 B2 | 10/2016 | Rothman |
| RE46,189 E | 11/2016 | Prichep |
| D771,823 S | 11/2016 | Hagedorn |
| 9,629,568 B2 | 4/2017 | Hagedorn |
| 9,711,056 B1* | 7/2017 | Nguyen .................. G09B 5/02 |
| D799,050 S | 10/2017 | Hagedorn |
| 9,788,747 B2 | 10/2017 | Hagedorn |
| 9,877,664 B2 | 1/2018 | Machon |
| 9,931,069 B2 | 4/2018 | Publicover |
| 10,092,195 B2 | 10/2018 | Lovoi |
| 10,548,501 B2 | 2/2020 | Hagedorn |
| 10,660,537 B2 | 5/2020 | Hagedorn |
| 10,780,268 B2 | 9/2020 | Hagedorn |
| 2004/0049105 A1* | 3/2004 | Crutchfield ............. A61B 8/56 600/407 |
| 2005/0124897 A1 | 6/2005 | Chopra |
| 2006/0135877 A1 | 6/2006 | Giftakis |
| 2006/0135881 A1 | 6/2006 | Giftakis |
| 2006/0136006 A1 | 6/2006 | Giftakis |
| 2006/0195144 A1 | 8/2006 | Giftakis |
| 2006/0224067 A1 | 10/2006 | Giftakis |
| 2007/0032737 A1 | 2/2007 | Causevic |
| 2007/0238939 A1 | 10/2007 | Giftakis |
| 2007/0239054 A1 | 10/2007 | Giftakis |
| 2007/0239060 A1 | 10/2007 | Giftakis |
| 2007/0239230 A1 | 10/2007 | Giftakis |
| 2007/0260147 A1 | 11/2007 | Giftakis |
| 2007/0260286 A1 | 11/2007 | Giftakis |
| 2007/0260289 A1 | 11/2007 | Giftakis |
| 2007/0265536 A1 | 11/2007 | Giftakis |
| 2007/0265677 A1 | 11/2007 | Giftakis |
| 2008/0033490 A1 | 2/2008 | Giftakis |
| 2008/0208073 A1 | 8/2008 | Causevic |
| 2009/0247894 A1 | 10/2009 | Causevic |
| 2009/0264785 A1 | 10/2009 | Causevic |
| 2010/0041962 A1 | 2/2010 | Causevic |
| 2010/0049101 A1 | 2/2010 | Chopra |
| 2010/0222694 A1 | 9/2010 | Causevic |
| 2011/0087082 A1 | 4/2011 | Giftakis |
| 2011/0105913 A1 | 5/2011 | Giftakis |
| 2011/0125048 A1 | 5/2011 | Causevic |
| 2011/0144520 A1 | 6/2011 | Causevic |
| 2011/0270117 A1* | 11/2011 | Warwick ............. A61B 5/0006 600/544 |
| 2012/0041330 A1 | 2/2012 | Prichep |
| 2012/0083717 A1 | 4/2012 | Alleman |
| 2012/0271377 A1 | 10/2012 | Hagedorn |
| 2012/0293773 A1 | 11/2012 | Publicover |
| 2013/0116015 A1 | 5/2013 | Lee |
| 2013/0184603 A1 | 7/2013 | Rothman |
| 2013/0281759 A1 | 10/2013 | Hagedorn |
| 2014/0051940 A1* | 2/2014 | Messerschmidt .... A61B 5/6815 600/301 |
| 2014/0058292 A1* | 2/2014 | Alford ................. A61N 1/0529 601/2 |
| 2014/0257073 A1 | 9/2014 | Machon |
| 2014/0288614 A1 | 9/2014 | Hagedorn |
| 2014/0289172 A1* | 9/2014 | Rothman ............. A61B 5/0476 706/11 |
| 2014/0316221 A1 | 10/2014 | Rothman |
| 2014/0350431 A1 | 11/2014 | Hagedorn |
| 2015/0032021 A1* | 1/2015 | Chen .................... A61B 5/6803 600/544 |
| 2015/0045606 A1 | 2/2015 | Hagedorn |
| 2015/0051663 A1 | 2/2015 | Hagedorn |
| 2015/0072324 A1* | 3/2015 | Pracar .................... A61B 5/16 434/236 |
| 2015/0112409 A1 | 4/2015 | Hagedorn |
| 2015/0157266 A1 | 6/2015 | Machon |
| 2016/0000354 A1 | 1/2016 | Hagedorn |
| 2016/0015289 A1 | 1/2016 | Simon |

(56) References Cited

U.S. PATENT DOCUMENTS

| | | | |
|---|---|---|---|
| 2016/0022167 A1* | 1/2016 | Simon | A61B 5/378 600/301 |
| 2016/0081608 A1* | 3/2016 | Lovoi | A61B 5/4064 600/483 |
| 2016/0132654 A1 | 5/2016 | Rothman | |
| 2016/0151018 A1 | 6/2016 | Machon | |
| 2016/0166190 A1 | 6/2016 | Publicover | |
| 2016/0256130 A1 | 9/2016 | Hamilton | |
| 2016/0278736 A1 | 9/2016 | Hamilton | |
| 2016/0367217 A1 | 12/2016 | Flores, II | |
| 2017/0027467 A1 | 2/2017 | Hagedorn | |
| 2017/0049611 A1 | 2/2017 | Rosh Vora | |
| 2017/0119347 A1 | 5/2017 | Flores, II | |
| 2017/0188932 A1 | 7/2017 | Singer | |
| 2017/0188992 A1 | 7/2017 | O'Brien | |
| 2017/0188993 A1 | 7/2017 | Hamilton | |
| 2017/0188994 A1 | 7/2017 | Flores, II | |
| 2017/0215760 A1 | 8/2017 | Hagedorn | |
| 2017/0307420 A1 | 10/2017 | Flores, II | |
| 2018/0020941 A1 | 1/2018 | Hagedorn | |
| 2018/0021021 A1 | 1/2018 | Zwierstra | |
| 2018/0064364 A1 | 3/2018 | Oziel | |
| 2018/0067600 A1 | 3/2018 | Li | |
| 2018/0078165 A1 | 3/2018 | Machon | |
| 2018/0103927 A1 | 4/2018 | Chung | |
| 2018/0103928 A1 | 4/2018 | Costa | |
| 2018/0103992 A1 | 4/2018 | Guyuron | |

FOREIGN PATENT DOCUMENTS

| | | |
|---|---|---|
| AU | 2006275864 A1 | 2/2007 |
| AU | 2009222024 A1 | 9/2009 |
| AU | 2009222024 B2 | 5/2011 |
| AU | 2011292220 A1 | 3/2013 |
| AU | 2013306411 A1 | 12/2014 |
| AU | 2011292220 B2 | 2/2015 |
| AU | 2014226506 A1 | 10/2015 |
| AU | 2013306411 B2 | 6/2016 |
| AU | 2014226506 B2 | 5/2017 |
| AU | 2017202427 A1 | 5/2017 |
| CA | 2616974 A1 | 2/2007 |
| CA | 2939790 A1 | 2/2007 |
| CA | 2717170 A1 | 9/2009 |
| CA | 2784267 A1 | 7/2011 |
| CA | 2808097 A1 | 2/2012 |
| CA | 2836779 A1 | 11/2012 |
| CA | 2873688 A1 | 7/2013 |
| CA | 2904529 A1 | 9/2014 |
| CA | 2616974 C | 10/2016 |
| CA | 2717170 C | 1/2017 |
| CA | 2939790 C | 1/2017 |
| CA | 2992961 A1 | 1/2017 |
| CA | 3008804 A1 | 7/2017 |
| CA | 2904529 C | 10/2017 |
| CN | 102014742 A | 4/2011 |
| CN | 102014742 B | 9/2013 |
| CN | 104519960 A | 4/2015 |
| CN | 105520732 A | 4/2016 |
| DE | 602005026054D1 | 3/2011 |
| EP | 1833557 A1 | 9/2007 |
| EP | 1833558 A1 | 9/2007 |
| EP | 1909643 A2 | 4/2008 |
| EP | 1909643 A4 | 3/2010 |
| EP | 2262422 A1 | 12/2010 |
| EP | 1833557 B1 | 1/2011 |
| EP | 1833558 B1 | 10/2011 |
| EP | 2512332 A1 | 10/2012 |
| EP | 2605700 A1 | 6/2013 |
| EP | 2710515 A2 | 3/2014 |
| EP | 2262422 B1 | 8/2014 |
| EP | 2814387 A1 | 12/2014 |
| EP | 2823760 A1 | 1/2015 |
| EP | 2710515 A4 | 2/2015 |
| EP | 2888004 A1 | 7/2015 |
| EP | 2964083 A1 | 1/2016 |
| EP | 1909643 B1 | 3/2016 |
| EP | 3068294 A1 | 9/2016 |
| EP | 2823760 B1 | 5/2017 |
| EP | 2710515 B1 | 4/2018 |
| EP | 3310261 A1 | 4/2018 |
| EP | 3324841 A1 | 5/2018 |
| HK | 1137634 A | 8/2010 |
| HK | 1156492 A1 | 5/2014 |
| HK | 1200303 A | 8/2015 |
| HK | 1219217 A | 3/2017 |
| HK | 1219640 A | 4/2017 |
| IL | 189163 | 8/2008 |
| IL | 207959 | 2/2016 |
| IL | 207959 A | 2/2016 |
| IN | 397KOLNP2008 A | 12/2008 |
| IN | 3251KOLNP2010 A | 11/2010 |
| IN | 622KOLNP2013 A | 7/2013 |
| IN | 1585MUMNP2014 A | 5/2015 |
| IN | 2928KOLNP2015 A | 2/2016 |
| JP | 2015533526 A | 11/2015 |
| SG | 139858 A1 | 3/2008 |
| WO | 2005061053 A1 | 7/2005 |
| WO | 2006066098 A1 | 6/2006 |
| WO | 2006066099 A1 | 6/2006 |
| WO | 2006066280 A1 | 6/2006 |
| WO | 2006066099 A9 | 8/2006 |
| WO | 2006086075 A1 | 8/2006 |
| WO | 2007016149 A2 | 2/2007 |
| WO | 2007016149 A3 | 4/2009 |
| WO | 2009111426 A1 | 9/2009 |
| WO | 2009129279 A1 | 10/2009 |
| WO | 2009138882 A2 | 11/2009 |
| WO | 2011084394 A1 | 7/2011 |
| WO | 2012024175 A1 | 2/2012 |
| WO | 2012162205 A2 | 11/2012 |
| WO | 2012162205 A3 | 3/2013 |
| WO | 2013063053 A1 | 5/2013 |
| WO | 2013109492 A1 | 7/2013 |
| WO | 2014031142 A1 | 2/2014 |
| WO | 2013109492 A8 | 8/2014 |
| WO | 2014137549 A1 | 9/2014 |
| WO | 2015073903 A1 | 5/2015 |
| WO | 2015187401 A1 | 12/2015 |
| WO | 2016205824 A1 | 12/2016 |
| WO | 2017013655 A1 | 1/2017 |
| WO | 2017116582 A1 | 7/2017 |
| WO | 2017118964 A1 | 7/2017 |
| WO | 2017120361 A1 | 7/2017 |
| WO | 2017120382 A1 | 7/2017 |
| WO | 2017120388 A1 | 7/2017 |
| WO | 2017189623 A1 | 11/2017 |
| WO | 2018017614 A1 | 1/2018 |
| WO | 2018075415 A1 | 4/2018 |
| WO | 2018075416 A1 | 4/2018 |
| WO | 2019200001 A1 | 10/2019 |

OTHER PUBLICATIONS

Poh et al., "Cardiovascular Monitoring Using Earphones and a Mobile Device", IEEE Pervasive Computing, 2010. Digital Object Identifier 10.1109/MPRV.2010.91.

Voss et al., "Detecting changes in intracranial pressure using ear-canal reflectance and otoacoustic emissions", Hearing Research as part of teh MEMRO group of manuscripts, Jul. 8, 2009.

Ganslandt et al., "Evaluation of a novel noninvasive ICP monitoring device in patients undergoing invasive ICP monitoring: preliminary results" J Neurosurg, Aug. 8, 2017, Published online Aug. 8, 2017; DOI: 10.3171/2016.11.JNS152268.

Canning et al., "Noninvasive and Continuous Blood Pressure Measurement via Superficial Temporal Artery Tonometry", Aug. 2016Conference proceedings: . . . Annual International Conference of the IEEE Engineering in Medicine and Biology Society. IEEE Engineering in Medicine and Biology Society. DOI: 10.1109/EMBC. 2016.7591453.

Mom et al., "Vasospasm of labyrinthine artery in cerebellopontine angle surgery: evidence brought by distortion-product otoacoustic

(56) References Cited

OTHER PUBLICATIONS emissions", Eur Arch Otorhinolaryngol (2014) 271:2627-2635, DOI 10.1007/s00405-013-2753-0.
International Search Report for PCT/US19/26833, dated Sep. 13, 2019.
Written Opinion of the International Searching Authority for PCT/US19/26833, dated Sep. 13, 2019.
Wikipedia, "Electret microphone", Mar. 28, 2016 (Mar. 28, 2016), retrieved on Jul. 5, 2019 from https://en.wikipedia.org/w/index.php?title=Elecret_microphone&oldid=712378585; entire document, especially p. 1 para 1.

\* cited by examiner

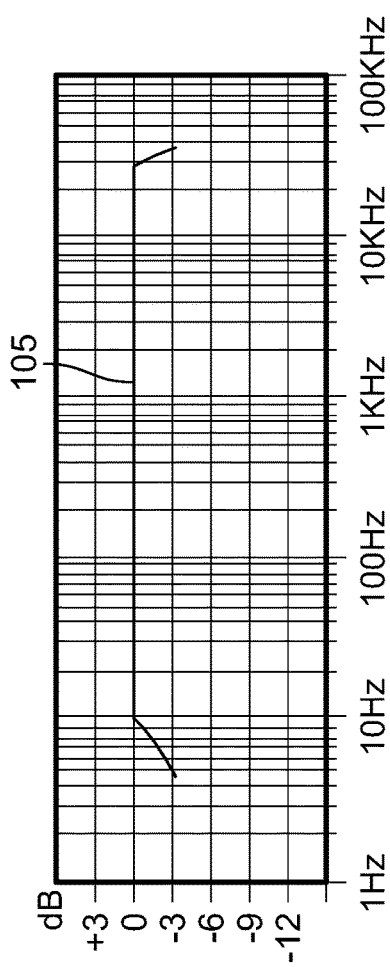
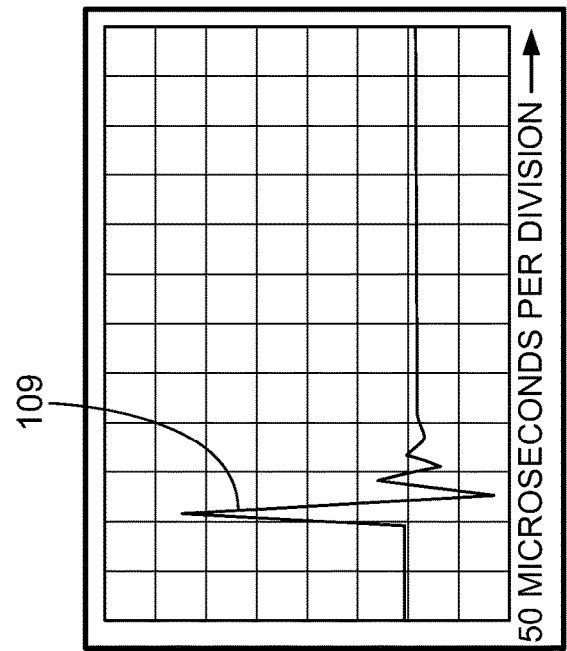
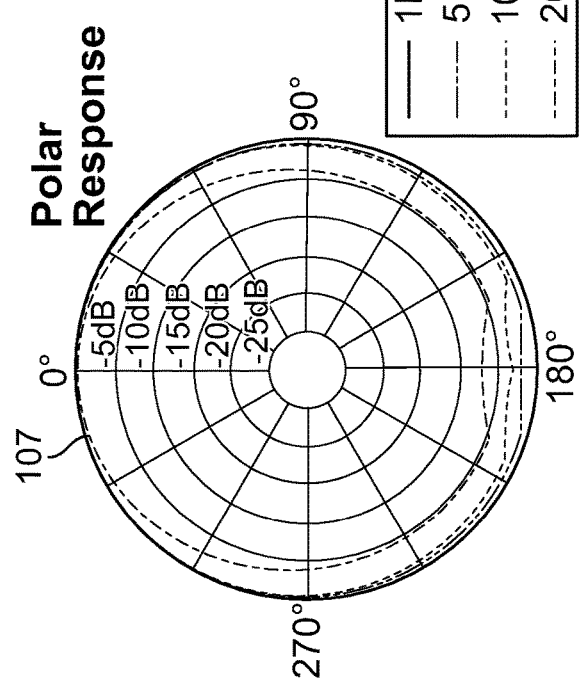
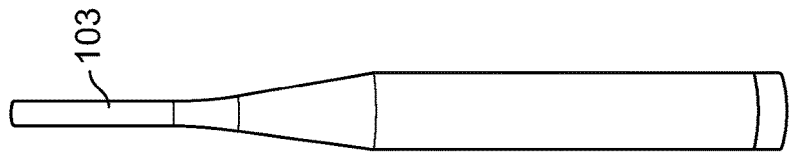

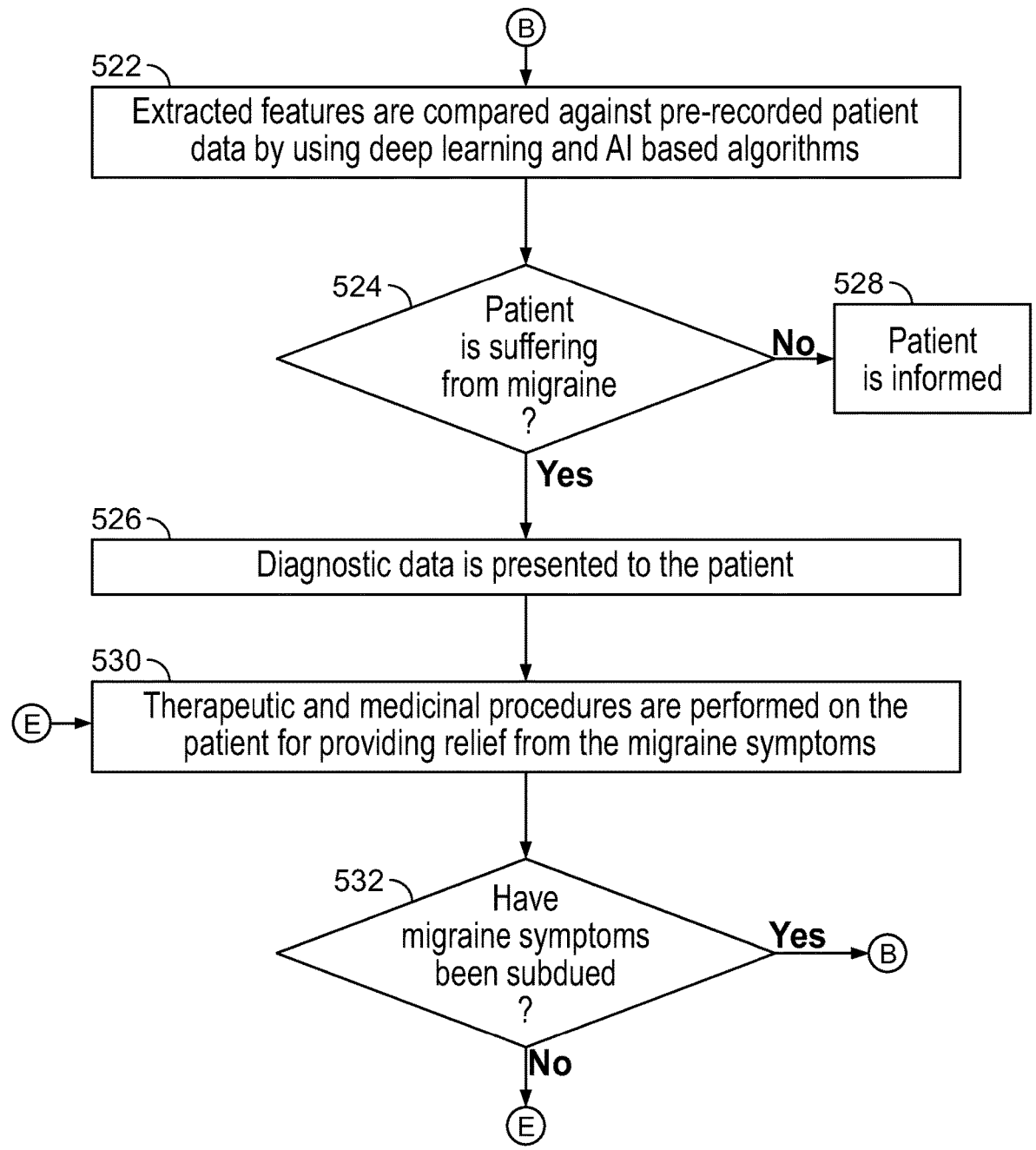
FIG. 5A(Contd.)

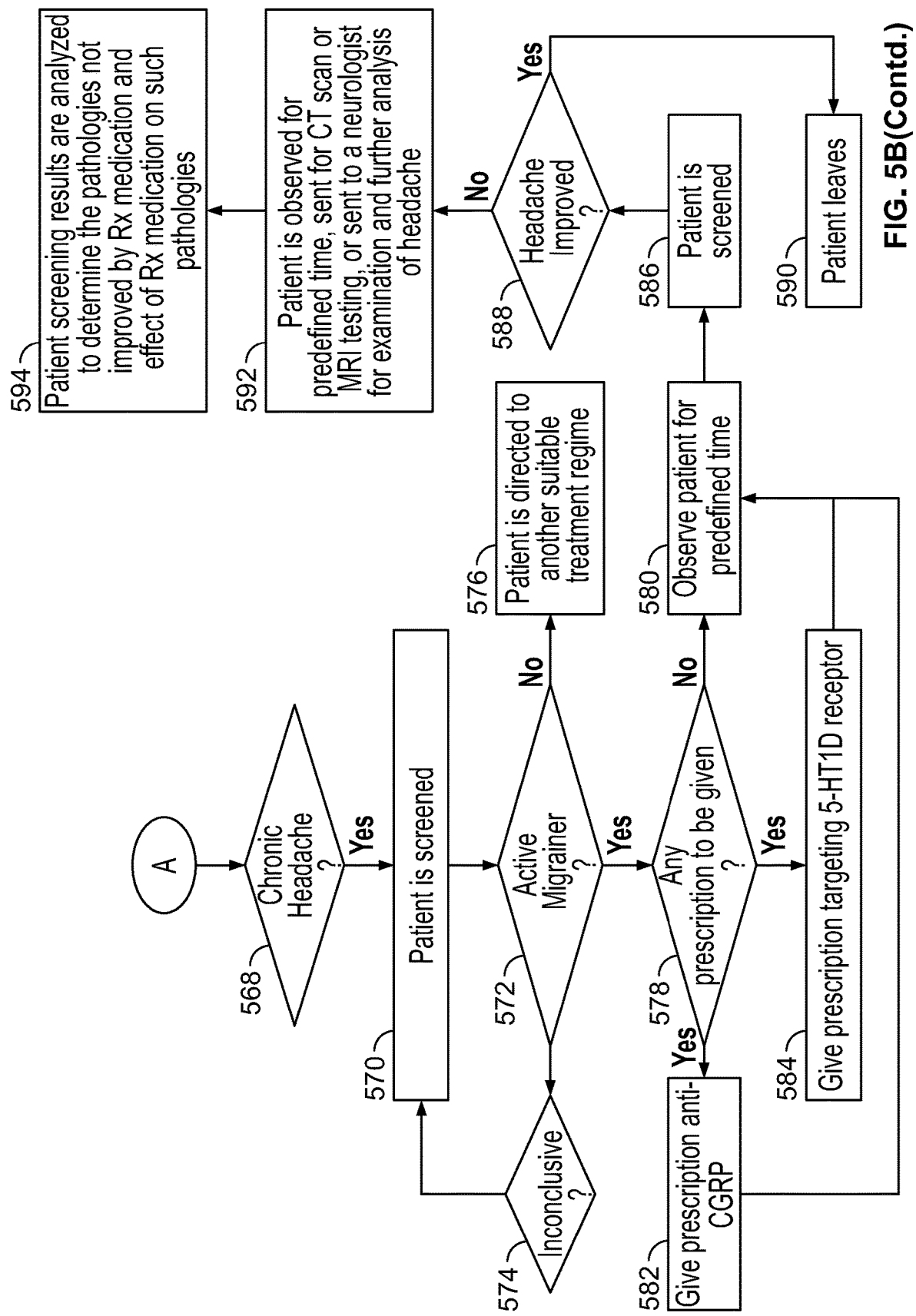
FIG. 5B(Contd.)

SYSTEMS AND METHODS FOR THE IDENTIFICATION OF MEDICAL CONDITIONS, AND DETERMINATION OF APPROPRIATE THERAPIES, BY PASSIVELY DETECTING ACOUSTIC SIGNALS FROM CEREBRAL VASCULATURE

CROSS-REFERENCE

The present specification relies on U.S. Patent Provisional Application No. 62/767,038, entitled "Systems and Methods for the Diagnosis of Medical Conditions Using a Detection of Signals Generated from Blood Flow in the Brain" and filed on Nov. 14, 2018, for priority and is hereby incorporated by reference in its entirety. The present specification also relies on U.S. Patent Provisional Application No. 62/655,752, entitled "Neurological Diagnostic and Therapeutic Device and Method" and filed on Apr. 10, 2018, for priority and is also hereby incorporated by reference in its entirety.

FIELD

The present specification relates generally to systems and method for non-invasively diagnosing and treating a plurality of medical conditions and/or pathologies. More specifically, the present specification relates to systems and methods for diagnosing and treating brain-related conditions, such as migraines and headaches, using a detection of signals generated from blood flow in the brain.

BACKGROUND

Currently, there are approximately 39 million people suffering from migraines in the U.S. and about one billion worldwide. Migraine patients can have significant risks of strokes and other neurological impairments. They lose productivity and their work, personal and family lives are affected.

Some of the most common causes that lead to migraines in patients are underlying central nervous system disorders, irregularities in the brain's blood vessel system or vascular system, genetic predisposition, and abnormalities of brain chemicals and nerve pathways. It is also currently believed that vasodilation and vasoconstriction are a byproduct (or secondary effects) of migraines while neuronal dysfunction is the primary driver in the pathophysiology of the disorder. It has been observed that nerve fibers involved in the localization of pain ascend from the trigeminal to the thalamus and sensory cortex of the trigeminovascular system of a patient experiencing symptoms of migraine; and distribution of headache pain to the upper neck and head are from the trigeminal nerve. Also, a self-propagating wave of cellular depolarization (cortical spreading depression) that spreads slowly across the cerebral cortex and has been linked to migraine aura and headache, as it activates neurons in the trigeminal nerve leading to inflammatory changes and headaches. Further, the neurons of a patient suffering from migraines become increasingly responsive to nociceptive (i.e. pain) stimulation and many of the symptoms of migraine, including throbbing headache pain and exacerbation of headache by physical activity are linked to neuron sensitization.

A majority of migraine patients do not get a timely and appropriate diagnosis or prescriptions to address the migraines. Currently, when a new patient presents in a neurologist's office with a suspicion of migraines, the neurologist is required to have the patient fill out a questionnaire and subjectively perform a work up on the patient based on symptoms, family history, medical history, neurological history and exam, MRI/CT scan, and blood tests. Based on this subjective assessment, the neurologist prescribes drugs to treat. The neurologist then waits for the patient to return in weeks or months to perform another subjective workup and seek to understand the impact of the drugs on the migraine. This is a time-consuming process, which may frustrate the patient if the recommendations and therapy are not effective. Even worse, however, initial therapeutic prescriptions may not be appropriately tailored to the patient, leading to ineffective treatments, or more problematically, mini-strokes in the patient.

U.S. Pat. Nos. 6,887,199 and 6,491,647 disclose a head-mounted brain sensor which non-invasively senses acoustic signals generated from pulsing blood flow on or around a patient's head. The assessment monitor may be used to detect conditions such as head trauma, stroke and hemorrhage. However, the observed changes in signal characteristics from normal to pathological states has to do with changes in acoustic properties as a result of injury, not of chronic brain conditions such as migraines. Moreover, the indicated locations of where the brain sensor(s) should be mounted, such as the forehead, will likely result in the detection of peripheral blood flow around the patient's head, as opposed to the cerebral vasculature.

Similarly, U.S. Pat. Nos. 10,092,195 and 8,905,932 are directed toward a head sensing system which detecting a vascular condition non-invasively in the human body. The assessment system may be used to detect conditions such as stroke, aneurysms, and hemorrhage. Again, the observed changes in signal characteristics from normal to pathological states has to do with changes in acoustic properties as a result of acute injury, not of chronic brain conditions such as migraines, and the indicated locations of where the brain sensor(s) should be mounted will likely result in the detection of peripheral blood flow around the patient's head, as opposed to the cerebral vasculature.

Usually holistic approaches to treating migraine, such as but not limited to meditation, acupuncture, cold water on the scalp, Valsalva maneuver have either no effect or a placebo effect on migraine symptoms. Pain relieving medications such as aspirin, ibuprofen, acetaminophen, caffeine (NSAIDS) and other over the counter drugs usually only dull the migraine pain for 3-4 hours leading to rebound headaches and drug overuse and may cause ulcers and gastrointestinal bleeding. Some pain-relieving medications containing triptans may cause strokes, arrhythmia, rebound headache, nausea, dizziness, drowsiness and palpitations in migraine patients. Other pain-relieving medications containing ergots may cause vomiting, tingling of the extremities, Pruritis, weakness of the legs and worsening of nausea in migraine patients. Yet other pain-relieving medications containing opioids are habit-forming, addictive and may cause severe opioid induced constipation, respiratory depression with risk of death when combined with a sedative such as Ambien or Benzodiazepines such as Temazepam or Alprazolam in migraine patients. Other pain-relieving medications containing glucocorticoids may increase sugar level, diabetes, osteoporosis, ulcers, gastritis, elevate cholesterol, cause weight gain, hirsutism, acne, and severe osteoporosis in migraine patients.

Currently available migraine preventive cardiovascular drugs such as beta blockers may have side effects such as arrhythmias, V-tach, worsened heart failure, depression, hallucinations, fatigue, marked impotence with males, bradycardia and hypotension in migraine patients. Sometimes anti-depressants may worsen or trigger migraine; and may cause sleepiness, dry mouth, constipation, weight gain, decreased cognition, anhedonia, lethargy, and increased suicide risk in migraine patients. Some anti-seizure drugs (Depacon AKA Valproic Acid, Depakote, Topamax) being used as migraine preventive drugs may cause nausea, tremors, weight gain, hair loss, dizziness, diarrhea, weight loss, memory difficulties, concentration problems, cognitive decline, tingling around the lips, hepatic issues, osteoporosis in migraine patients. Some patients are prescribed Botox (Chemodenervation with BOTOX A, Xeomin, Dysport, Myobloc) as preventive treatment for migraines. This is a costly, lengthy and painful process (involving sometimes up to 31 injections administered to the patient in three months) and may cause neck pain, headache, worsening of migraine, muscular weakness and eyelid ptosis in said patients.

Currently, there are no reliable, available diagnostic devices to provide a quick and efficient way of distinguishing between a migraine, tension headache and other non-traumatic injury brain-related conditions and deliver an objective, quantitative assessment of the patient's condition. Patients usually have to undergo elaborate examination procedures including CT scans, which are time consuming, tedious and expensive and are used to only rule out bleeding, not to diagnose migraines.

There is therefore a need for an objective means to determine the nature of a patient's condition and thereby help diagnose a spectrum of brain-related non-traumatic disease conditions and offer targeted therapies. There is also a need for a diagnostic system and method that would enable quick efficient and cost-effective diagnosis of several pathologies including migraines. There is also a need for a diagnostic system and method that would provide the requisite data needed to determine what therapy to diagnosis, what therapeutic protocol to adopt, and/or whether a particular drug or therapy is effective.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a system for diagnosing one or more pathologies in a patient, wherein the system comprises: a headset comprising at least one microphone or accelerometer to passively receive vibrations generated by a cerebral vasculature of the patient's brain; at least one computing device coupled with the headset for processing the received vibrations to obtain a signal; and a signal analyzer coupled with the at least one computing device and configured to analyze the signal to identify a pattern indicative of one or more predefined pathologies, wherein the predefined pathologies comprise at least one of tension headaches, migraines, depression, vascular dementia, Alzheimer's disease, epilepsy, vascular Parkinson's disease, autism, cerebral vasospasm, or meningitis.

Optionally, the signal analyzer is configured to differentiate between each of the predefined pathologies and output an audio or visual indicator that specifically identifies one of the predefined pathologies while concurrently excluded a remainder of the predefined pathologies.

Optionally, the signal analyzer is not configured to identify a traumatic brain injury, stroke, aneurysm, or hemorrhage.

Optionally, the headset comprises two microphones, wherein each of the two microphones is provided within each ear covering of the headset.

Optionally, the at least one microphone captures and outputs bi-hemispheric data and has an output for detecting vibration in a range of 0-750 kHz.

Optionally, the headset is an electrostatic headset comprising a pre-amplifier, a frequency equalizer and a noise cancellation module.

Optionally, the headset comprises a signal quality indicator configured to indicate a quality of the vibrations being received, a light source configured to visually indicate that the headset is in an operational mode, and a light array configured to indicate a level of battery charge.

Optionally, the at least one computing device comprises at least one of an Internet of Things (IoT) device, mobile phone, tablet device, desktop computer or laptop computer.

Optionally, the at least one microphone or accelerometer is configured to be positioned within a predefined distance of at least one of the patient's basilar artery, anterior inferior cerebellar artery, anterior vestibular artery, internal auditory artery, common cochlear artery, internal carotid artery, or ophthalmic artery. Optionally, the predefined distance is 10 mm.

Optionally, the at least one microphone or accelerometer is configured to be positioned outside of a predefined distance from at least one of the patient's zygoma, external carotid artery, internal maxillary artery, facial artery, or occipital artery. Optionally, the predefined distance is 5 mm.

Optionally, the at least one microphone or accelerometer is configured to be positioned within a first predefined distance of at least one of the patient's basilar artery, anterior inferior cerebellar artery, anterior vestibular artery, internal auditory artery, common cochlear artery, internal carotid artery, or ophthalmic artery and outside of a second predefined distance from at least one of the patient's zygoma, external carotid artery, internal maxillary artery, facial artery, or occipital artery, wherein the first predefined distance is less than the second predefined distance. Optionally, the first predefined distance is within a range of 0 mm to 5 mm and the second predefined distance is at least 5 mm.

Optionally, the signal analyzer is coupled with the at least one computer device via at least one of a wireless network connection, a wired connection or a Bluetooth connection.

Optionally, the system further comprises one or more databases coupled with the signal analyzer, wherein the one or more databases comprises pre-determined signal classifications comprising specific frequencies, frequency ranges, energies, energy ranges, periodicities or periodicity ranges unique to each of the predefined pathologies. Optionally, the signal analyzer comprises one or more algorithms configured to detect one or more of the predefined pathologies present in the signal by comparing the analyzed signal with the pre-determined signal classifications comprising specific frequencies unique to each of the predefined pathologies.

Optionally, the system further comprises a second computing device configured to receive the pattern, compare the pattern to a plurality of predefined patterns indicative of the one or more predefined pathologies, and categorize the pattern as being representative of the one or more predefined pathologies. Optionally, the plurality of predefined patterns are indicative of a plurality of different migraine types. Optionally, the plurality of different migraine types comprise aura, without aura, basilar, hemiplegic, ophthaloplegic, vestibular or chronic. Optionally, the plurality of predefined patterns is derived from signal measurements taken from individuals other than the patient.

The present specification also discloses a method for determining if a patient is suffering from a condition, wherein the condition is at least one of tension headaches, migraines, depression, vascular dementia, Alzheimer's disease, epilepsy, vascular Parkinson's disease, autism, cerebral vasospasm or meningitis, the method comprising: positioning at least one microphone or accelerometer within a first predefined distance of at least one of the patient's basilar artery, anterior inferior cerebellar artery, anterior vestibular artery, internal auditory artery, common cochlear artery, internal carotid artery, or ophthalmic artery and outside of a second predefined distance from at least one of the patient's zygoma, external carotid artery, internal maxillary artery, facial artery, or occipital artery, wherein the first predefined distance is less than the second predefined distance; capturing a signal transduced through a medium, wherein the medium is at least one of air, tissue, bone, vasculature, or nerves, wherein the signal is generated by blood flow in a cerebral vasculature of the patient's brain and is not a function of a second signal originating external to the patient, and wherein the signal is captured using at least one of the accelerometer or the microphone; digitizing the captured signal using a first component in data communication with the accelerometer or microphone; transmitting the digitized captured signal to a signal analyzer using a second component in data communication with the first component; using the signal analyzer, acquiring the digitized captured signal and processing the acquired digitized captured signal to identify a signature, wherein the signature is a function of a non-zero amplitude, frequency and periodicity of the signal and wherein the signature is uniquely indicative of one of a tension headache, a migraine, depression, vascular dementia, Alzheimer's disease, epilepsy, vascular Parkinson's disease, autism, cerebral vasospasm or meningitis.

Optionally, the first predefined distance is within a range of 0 mm to 5 mm and the second predefined distance is at least 5 mm.

Optionally, the method further comprises accessing one or more databases, wherein the one or more databases comprises pre-determined signal classifications comprising specific frequencies, frequency ranges, energies, energy ranges, periodicities or periodicity ranges unique to each of a plurality of predefined pathologies.

Optionally, the signal analyzer comprises one or more algorithms configured to detect one or more of a plurality of predefined pathologies present in the signal by comparing the signal with pre-determined signal classifications comprising specific frequencies unique to each of the plurality of predefined pathologies.

Optionally, the method further comprises, using a computing device, receiving the signature, compare the signature to a plurality of predefined patterns indicative of one or more predefined pathologies, and categorize the signature as being representative of the one or more predefined pathologies.

Optionally, the plurality of predefined patterns is indicative of a plurality of different migraine types. Optionally, the plurality of different migraine types comprise aura, without aura, basilar, hemiplegic, ophthaloplegic, vestibular or chronic. Optionally, the plurality of predefined patterns is derived from signal measurements taken from individuals other than the patient.

The present specification also discloses a diagnostic system for determining if a patient is suffering from a condition, wherein the condition is at least one of tension headaches, migraines, depression, vascular dementia, Alzheimer's disease, epilepsy, vascular Parkinson's disease, autism, cerebral vasospasm or meningitis, the diagnostic system comprising: at least one of an accelerometer or a microphone configured to capture a signal transduced through a medium, wherein the medium is at least one of air, tissue, bone, vasculature, or nerves, wherein the signal is generated by blood flow in the brain and is not a function of a second signal originating external to the patient, and wherein the accelerometer or the microphone is positioned no more than 1 foot from an ear of the patient; a digitizer in data communication with the accelerometer or microphone and configured to digitize the captured signal; a transmitter in data communication with the digitizer and configured to transmit the digitized captured signal; a signal analyzer configured to acquire the digitized captured signal and process the acquired digitized captured signal to identify a signature, wherein the signature is a function of a non-zero amplitude, frequency and periodicity of the signal and wherein the signature is uniquely indicative of one of a tension headache, a migraine, depression, vascular dementia, Alzheimer's disease, epilepsy, vascular Parkinson's disease, autism, cerebral vasospasm or meningitis.

The present specification also discloses a method for diagnosing one or more pathologies in a patient, the method comprising: receiving audio data comprising vibrations generated from cardiac cycles of the patient using a headset positioned on the patient's head; processing the audio data to obtain a spectrograph comprising a unique frequency pattern corresponding to the patient; comparing the obtained spectrograph with pre-recorded spectrographs comprising frequencies unique to a predefined type of pathology to obtain a diagnostic result; and conveying the diagnostic result to the patient.

Optionally, the pathology is a migraine. Optionally, the method further comprises collecting the patient's medical history relating to migraines by using a pre-treatment questionnaire before receiving the audio data from the patient.

Optionally, the processing of audio data comprises cancelling noise signals from the audio data by comparing the audio data with a plurality of pre-recorded identified environmental noises and filter the pre-recorded identified environmental noises from the audio data, wherein the noise signals comprise all signals not originating from the patient's ear canal. Optionally, the identified environmental noises comprise noises caused by at least one of air conditioning (AC), lighting, microphone, human movement, keyboard clicks, car traffic, low frequency noise, respiration, or speech.

Optionally, receiving audio data comprises capturing changes in pressure caused by a pulsation of blood through blood vessel walls of the patient in form of pressure-related audio waves and converting the captured pressure-related audio waves to electrical energy by using one or microphones placed within one or both ear coverings of the headset.

Optionally, the method further comprises differentiating between at least one of a non-migraine condition, an active migraine condition, an asymptomatic migraine condition and a post therapy migraine condition in the patient. Optionally, said differentiation between said migraine conditions is performed by determining unique frequency patterns within frequency analyses and/or spectrographs corresponding to each of the migraine conditions.

Optionally, conveying the diagnostic result to the patient comprises visually presenting the diagnostic result in a graphical user interface on a user device or a mobile phone.

Optionally, the method further comprises capturing facial expressions or speech patterns of the patient and using the captured facial expressions or speech patterns to enhance an accuracy of a diagnosis of the predefined type of pathology.

The present specification also discloses a method of diagnosing a migraine in a patient using a device having at least one of an accelerometer or a microphone, comprising: positioning the microphone or the accelerometer within a first predefined distance of at least one of the patient's basilar artery, anterior inferior cerebellar artery, anterior vestibular artery, internal auditory artery, common cochlear artery, internal carotid artery, or ophthalmic artery and outside of a second predefined distance from at least one of the patient's zygoma, external carotid artery, internal maxillary artery, facial artery, or occipital artery, wherein the first predefined distance is less than the second predefined distance; using the device, capturing an analog signal transmitted through a head of the patient, wherein the analog signal is generated by blood flow in the patient's brain and wherein the analog signal is not a function of a second signal originating external to the patient; using a digitizer in data communication with at least one of the accelerometer or the microphone, transforming the analog signal into a digital signal; using a transmitter in data communication with the digitizer, transmitting the digital signal to a digital signal processing module; using the digital signal processing module, acquiring the digital signal and processing the digital signal to identify a signature of the migraine, wherein the signature has a first signal peak having a non-zero amplitude and a frequency in a range of 20 Hz to 1000 Hz and a second signal peak having a non-zero amplitude and a frequency in a range of 20 Hz to 1000 Hz, wherein the first signal peak and second signal peak are separated by a time period of no more than 60 seconds; and, based on said processing of the digital signal, generating a visual or auditory output indicative of whether the patient has said migraine.

Optionally, the signature has a first signal peak having a non-zero amplitude and a frequency in a range of 20 Hz to 800 Hz. Optionally, the signature has a second signal peak having a non-zero amplitude and a frequency in a range of 20 Hz to 800 Hz.

Optionally, the first signal peak and second signal peak are separated by a time period ranging from 1.7 seconds to 5 seconds.

Optionally, the first signal peak and second signal peak are separated by a time period that is 30 seconds or less.

Optionally, the first predefined distance is less than 10 mm and the second predefined distance is more than 5 mm.

The present specification also discloses a system for diagnosing one or more pathologies in a patient, the system comprising: a sensor positioned to passively detect vibrations generated by the vasculature of the patient's brain; at least one computing device coupled with the sensor for recording and processing the received vibrations to obtain a signal; and a signal analyzer coupled with the at least one computing device and configured to analyze the signal to identify a pattern indicative of one or more predefined pathologies, wherein the predefined pathologies comprise at least one of tension headaches, migraines, depression, vascular dementia, Alzheimer's disease, epilepsy, vascular Parkinson's disease, autism, cerebral vasospasm, or meningitis.

Optionally, the sensor is positioned to detect vibrations in at least one of basilar artery, anterior inferior cerebellar artery, anterior vestibular artery, internal auditory artery, common cochlear artery, or internal carotid artery of the patient.

Optionally, the sensor is positioned in an ear canal of the patient.

Optionally, the sensor is positioned to detect vibrations in an ophthalmic artery of the patient.

Optionally, the sensor is a stethoscope positioned over closed eyelids of the patient.

Optionally, the system further comprises a reference sensor for enabling removal of signals detected from peripheral arteries of the patient.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings:

FIG. 1B illustrates the M30 microphone provided by Earthworks, Inc., which may be used in accordance with an embodiment of the present specification;

FIG. 1C is a graph illustrating a frequency response of the M30 microphone;

FIG. 1D is a graph illustrating a polar response of the M30 microphone;

FIG. 1E is a graph illustrating an impulse response of the M30 microphone;

DETAILED DESCRIPTION

Figure 1A:
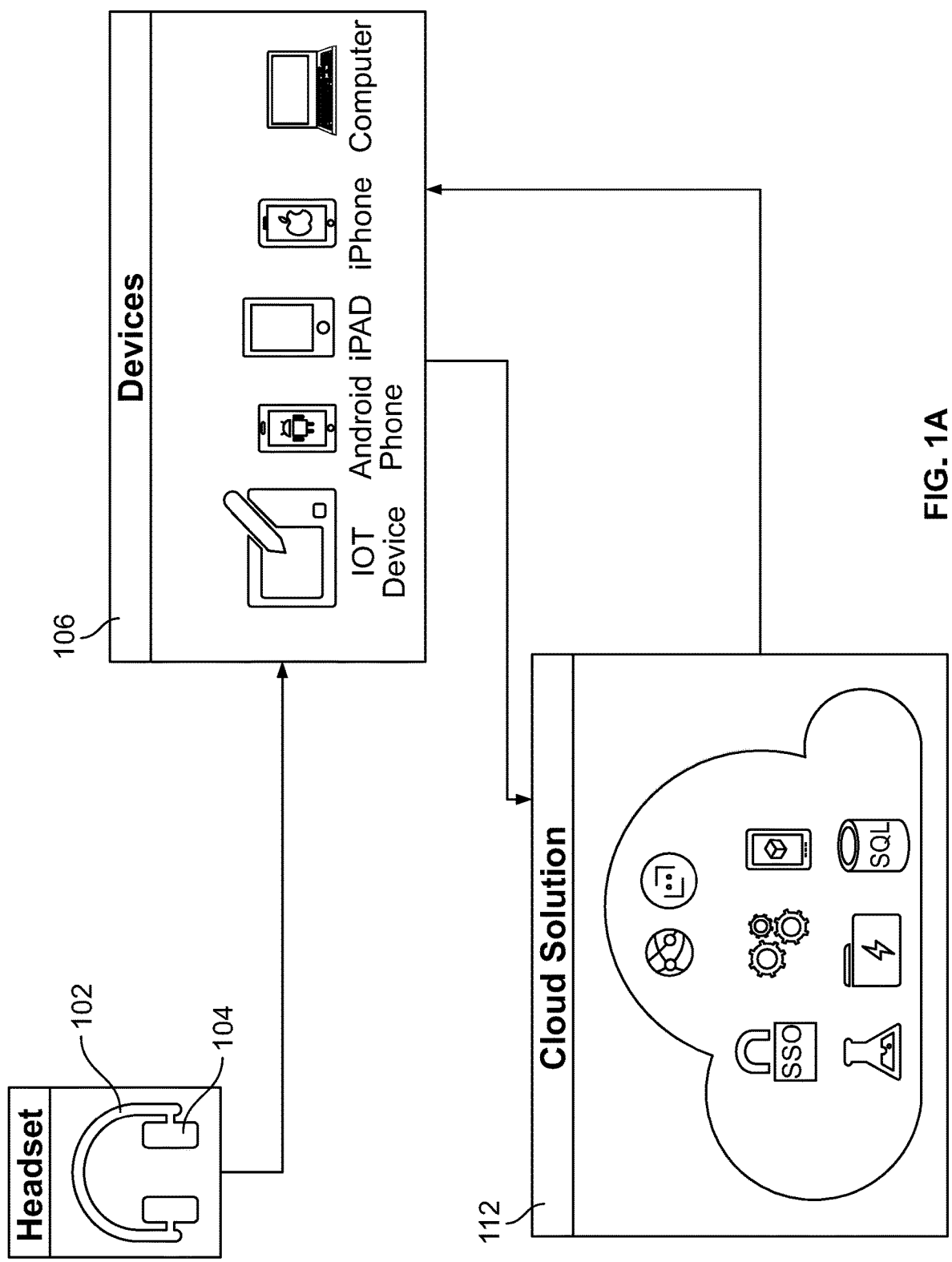
FIG. 1A is a block diagram illustrating a system of diagnosing and treating a plurality of pathologies in a patient, in accordance with an embodiment of the present specification.

In an embodiment, the present specification provides a system and method for diagnosing and treating a plurality of medical conditions/pathologies such as, but not limited to, non-traumatic brain conditions, migraines, depression, vascular dementia, Alzheimer's disease, epilepsy, vascular Parkinson's, autism spectrum, cerebral vasospasm, and meningitis pathologies. These chronic, non-traumatic brain conditions differ from traumatic brain injuries (TBI) which present acutely and involve brain swelling and bleeding with a gross insult on the brain. The neuro-chronic pathologies listed above present differently from an acoustic perspective, relative to acoustic characteristics seen with TBI, wherein each condition has a vascular component and a resultant frequency expression resulting in a unique signature different from the signature produced by TBI. Furthermore, detection of non-traumatic brain conditions requires a careful determination of what vasculature structures are being detected to avoid detecting blood flow signatures through a patient's peripheral head vasculature as opposed to blood flow signatures through the patient's brain.

The present specification is directed towards multiple embodiments. The following disclosure is provided in order to enable a person having ordinary skill in the art to practice the specification. Language used in this specification should not be interpreted as a general disavowal of any one specific embodiment or used to limit the claims beyond the meaning of the terms used therein. The general principles defined herein may be applied to other embodiments and applications without departing from the spirit and scope of the specification. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the specification have not been described in detail so as not to unnecessarily obscure the present specification.

In the description and claims of the application, each of the words "comprise", "include", and "have", and forms thereof, are not necessarily limited to members in a list with which the words may be associated. It should be noted herein that any feature or component described in association with a specific embodiment may be used and implemented with any other embodiment unless clearly indicated otherwise.

In the specification the term "module" represents any digital or software component ranging from a discrete chip to a software algorithm the processing of which is distributed across multiple servers.

In an embodiment, the present specification provides a headset designed to be placed on a patient's head with at least one sensor, such as an accelerometer or microphone, positioned proximate to the patient's ear canal, such as within an ear cover of a headset. The headset is configured to passively detect the vibration of a fluid or elastic solid generated from the cardiac cycle of the patient and, more specifically, from the pulsatile cerebral blood flow, as opposed to peripheral blood flow in the patient's head. In embodiments, the headset may be configured to passively detect acoustic frequencies. In various embodiments, the detected vibrations are compared with a predefined set of pre-recorded vibrations for determining whether the detected vibrations from the patient correspond to any of a plurality of medical conditions/pathologies such as, but not limited to, non-traumatic brain conditions, migraines, depression, dementia, Alzheimer's disease, epilepsy, Parkinson's, autism spectrum, cerebral vasospasm and meningitis.

In an embodiment, the one or more sensors passively receive the vibrations generated by the vasculature of the patient's brain. The vibrations (data) may be, in an embodiment, transmitted via Bluetooth from the headset to an Internet of Things (IOT) device that is configured to store algorithms configured to identify the pathology of interest, provide diagnostic data to the patient or transmit the diagnostic data to a cloud computing platform for analysis, and send the information back to the patient's smart device allowing the patient to obtain therapy for the pathology. In embodiments, data may be transmitted via any wired or wireless means. In embodiments, the headset may include a microchip or real-time operating system (RTOS).

In an embodiment, the vibrations generated by the pulsatile cerebral hemodynamics (cardiac cycle) of the patient is displayed as a heat spectrograph, which when compared with the heat spectrograph of a healthy person, demonstrates a shift in frequencies associated with one or more pathologies.

Figure 1F:
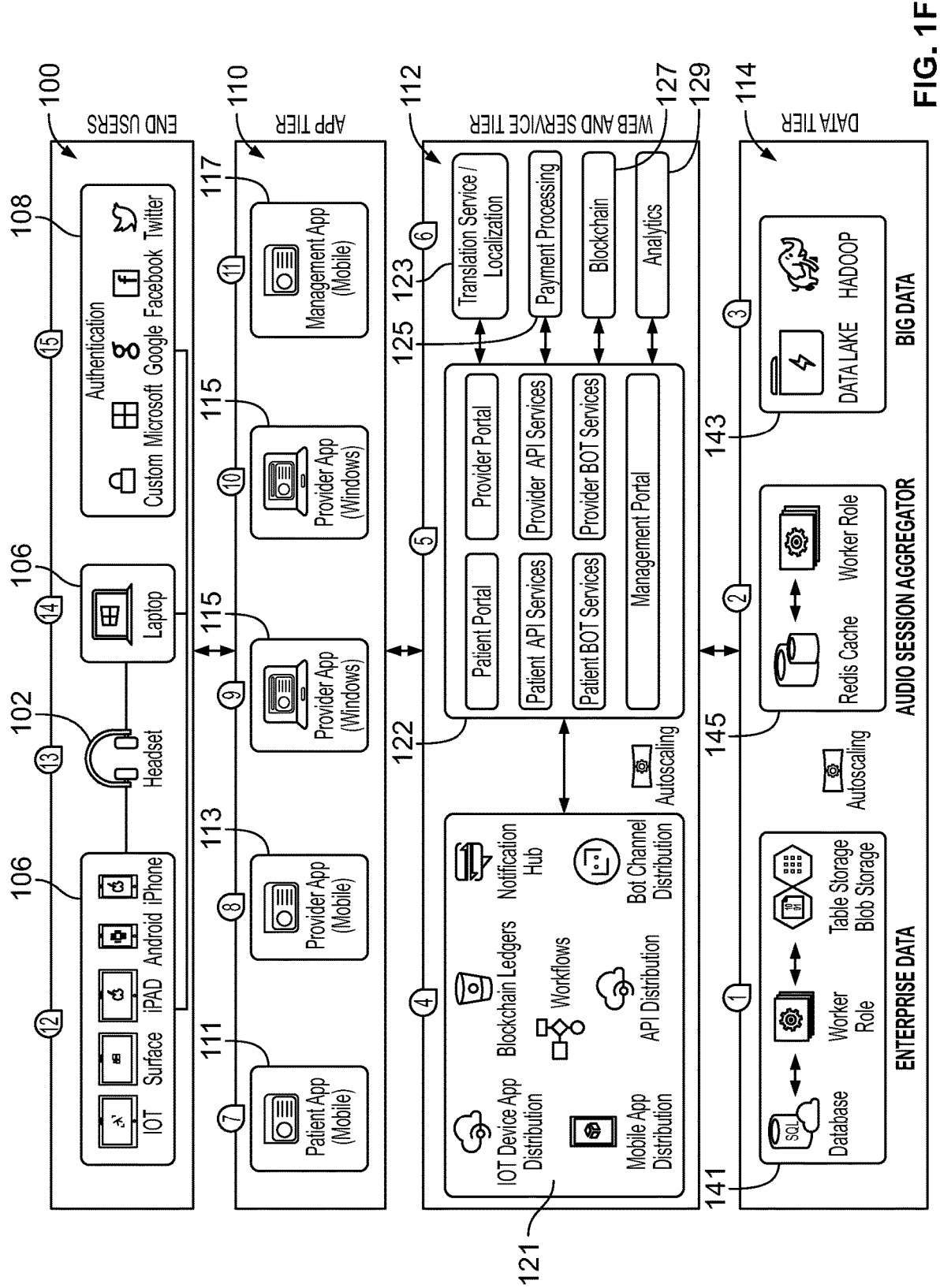
FIG. 1F is a block diagram illustrating a plurality of functional layers in the system of diagnosing and treating a plurality of pathologies in a patient, in accordance with an embodiment of the present specification.

FIG. 1A is a block diagram illustrating a system of diagnosing and treating a plurality of pathologies in a patient, in accordance with an embodiment of the present specification. FIG. 1F is a block diagram illustrating a plurality of functional layers in the system of diagnosing and treating a plurality of pathologies in a patient, in accordance with an embodiment of the present specification.

Referring to FIGS. 1A and 1F, the system comprises a headset 102 comprising two microphones 104, one microphone provided within each ear covering of the headset. The microphones 104 are configured to passively receive the vibrations generated by the vasculature of the brain of a patient wearing the headset 102. In an embodiment, the microphones (or pre-amplifiers, A/D converters, or blue tooth transmitters) 104 provide bi-hemispheric data and are designed to have a flat, consistent output to detect vibration in the range of 0-750 kHz. In an embodiment, the two ear coverings of the headset 102 have a parabolic design to enhance the capture of the vibrations generated by the patient and enhance the detected vibrations relative to external noise. In other embodiments, the ear coverings of the headset 102 may be designed in any suitable manner for detecting the vibrations from the patient's vasculature.

In another, less preferred embodiment, the headset 102 is an electrostatic headset comprising a pre-amplifier, a frequency equalizer and a noise cancellation module. The headset comprises a signal generating apparatus configured to generate an acoustic or ultrasound signal into the brain. In preferred embodiments, the headset 102 is configured to passively receive the vibrations generated by the vasculature of the brain of a patient and does not include a signal generating apparatus, including any acoustic or ultrasound generating apparatus.

In various embodiments, the microphone 104 is accurate in the time and frequency domain and has a uniform polar response, a flat free-field frequency response, fast impulse response and is stable with respect to temperature changes. An exemplary microphone is the M30 microphone 103 provided by Earthworks, Inc.™, illustrated in FIG. 1B, which may be used in accordance with an embodiment of the present specification. The M30 microphone provides a frequency response in the range of 5 Hz to 30 KHz±1/−3 dB. FIG. 1C is a graph illustrating a frequency response 105 of the M30 microphone. The M30 microphone has an omni-directional polar pattern, a sensitivity of 34 mV/Pa and a maximum acoustic input of 138 dB SPL. FIG. 1D is a graph illustrating a polar response of the M30 microphone. FIG. 1E is a graph illustrating an impulse response 109 of the M30 microphone. As is known, a self-noise below 10 dB is difficult to obtain in a microphone, as even a very quiet recording room will contribute more ambient noise than 10 dB-A. Typically, extremely low self-noise figures are only found on large diaphragm condenser microphones. Noise in the range of 11-15 dB-A is the minimum self-noise figure that can be found on a small diaphragm condenser or a large diaphragm condenser with tube electronics. Typically, 16-19 dB-A is a desirable self-noise, and 20-23 dB-A is a high self-noise figure for a studio microphone, as this is a noise level that's clearly audible. Such noise figures may be acceptable for recording loud sources but may not be used for recording anything below speaking level. In various embodiments, the preferred microphone 104 has a self-noise of less than or equal to 20 dB-A. In some embodiments, the microphones 104, or pre-amplifiers of the headset 102, comprise Phoenix Audio® (pre-amp) DRS-8-MK2 microphone pre-amps, having the following specifications: (1) High Pass Filter: on Push-button Switch (Roll-off–6 dB per octave @ 80 Hz); (2) Class A (DSOP-2) Output specs— Frequency response: 20 Hz to 20 kHz+/−0.5 dB (2) Noise=− 90 dB @ 20 Hz to 20 kHz; and (3) Gain Range (Mic input): −30 to −70 in 5 dB steps with 10 dB more available on the fader. In some embodiments, a clean power source is also provided. In some embodiments, the power source comprises a Monster® Power AVS 2000.

In an embodiment, the headset 102 comprises an accelerometer to detect movement from a patient's head, and not just from the patient's vasculature. In an embodiment, the patient is held still by using head gear or one or more harnesses and multiple accelerometers are used to capture signals indicative of movement by the patient. Those captures signals can then be used to cancel out noise generated from movement. In various embodiments, the site of the transducer is distant from muscles and skin that are activated and can move during the examination.

In an embodiment, the headset 102 comprises a signal quality indicator (SQI) to indicate the quality of a signal prior to a test being run, a light emitting diode (LED) to indicate that the headset is on and a light array to indicate a level of battery charge. In an embodiment, the headset 102 may be coupled with a plurality of user computing devices 106 such as, but not limited to Internet of Things (IoT) devices, mobile phones, tablets, and computers 106 via a wireless connection such as, but not limited to, a Wi-Fi network, cellular, or a Bluetooth connection. In embodiments, the user devices 106 enable display of data captured by the headset 102 and other notifications to the user using the headset. In embodiments, the user may be required to provide authentication information by using one of a plurality of authentication methods comprising custom authentication, or authentication methods provided by service providers 108 such as, but not limited to Google®, Facebook®, and Twitter®. In some embodiments, the headset 102, user devices 106, and service providers are grouped in an end user's tier 100.

In embodiments, a plurality of software applications 110 executing on the user devices 106 enable connection of the user devices 106 with the headset 102 as well as with a cloud solution computing platform (web and service tier) 112 via a wireless connection such as, but not limited to, a Wi-Fi network, cellular, or a Bluetooth connection. The applications 110 may comprise patient mobile applications 111, service provider mobile applications 113, service provider Windows® applications 115, and management applications 117, which also enable transfer and display of information captured/processed by the headset 102 and the cloud solution computing platform 112.

In various embodiments, the cloud solution computing platform (web and service tier) 112 comprises a management portal 122, a workflow module 121, and a set of service or storage modules, including, but not limited to, a translation service/localization module 123, a payment processing module 125, a blockchain module 127, and an analytics module 129. In embodiments, the management portal 122 comprises a patient portal, patient API services, patient BOT services, a provider portal, provider API service, and provider BOT services. The management portal 122 is in data communication with the workflow module 121, which controls IOT device application distribution, blockchain ledgers, a notification hub, mobile application distribution, API distribution, and BOT channel distribution. The management portal 122 is also in data communication with each of the translation service/localization module 123, payment processing module 125, blockchain module 127, and analytics module 129, providing patients and providers access to these modules via the patient portal and provider portal, for various services.

The vibrations detected by the microphones 104 are analyzed by a signal analyzer comprising at least one processor and a plurality of programmatic instructions stored in a memory, where the plurality of programmatic instructions include DSP, and machine learning, Artificial Intelligence, deep learning, neural networks (NN) and pattern recognition based algorithms, such as neural networks and artificial intelligence systems, in order to detect one or more of a set of pre-defined pathologies present in the detected vibrations of the patient. Preferably, pre-recorded acoustic patterns and specific frequencies unique to each kind of pathology are stored in one or more databases 114 coupled with the signal analyzer, which may be executed in a cloud solution computing platform 112.

Each pathology generates a unique acoustic pattern and specific frequency that enables identification of the pathology. For example, migraines generate (depicted by a spectrograph) a unique frequency pattern associated with the migraine. Using DSP, machine learning, and or AI pattern recognition based algorithms, the migraine severity levels may be identified. In an embodiment, data describing a pathology collected from each case is used to expand the database, which further enhances the quality/accuracy of the AI algorithms. In an embodiment, each patient's data is also sent to a secure website which provides patients an encrypted/password protected access to their data and history.

In an embodiment, the cloud solution computing platform 112 is coupled with one or more user devices 106 via a wireless connection such as, but not limited to, a Wi-Fi network, or a Bluetooth connection. In various embodiments, the user devices 106 comprise a graphical user interface (GUI) for displaying at least a diagnosis of the patient's condition. In an embodiment, the GUI displays one or more pathologies determined by the AI algorithms. In an embodiment, the user devices 106 also receive packets of diagnostic information from the cloud solution computing platform 112, to provide information on the severity of the pathology and display the information as a quantitative value.

Figure 2:
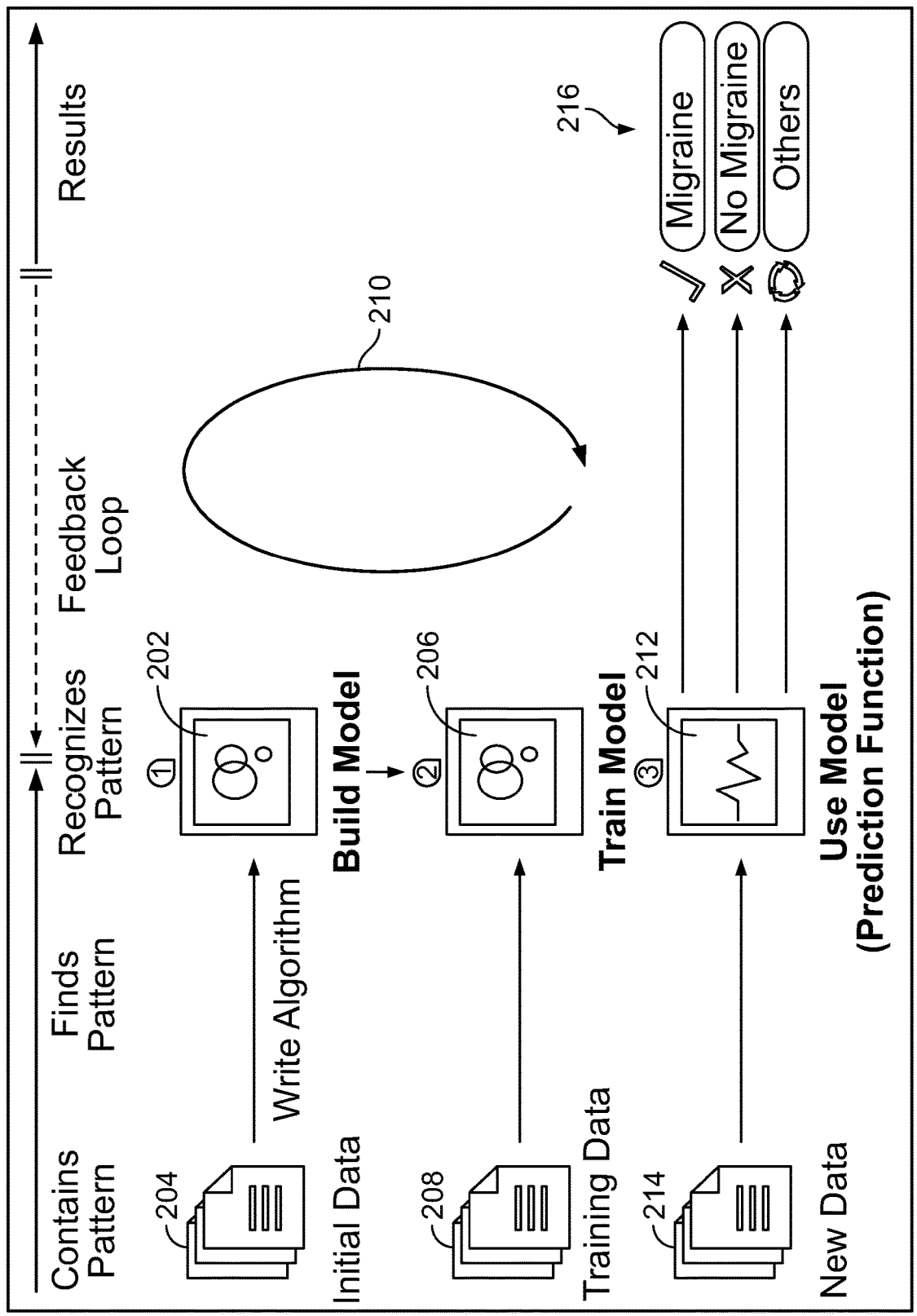
FIG. 2 is a block diagram illustrating a process of diagnosing pathologies by using artificial intelligence (AI) based algorithms, in accordance with an embodiment of the present specification.

FIG. 2 is a block diagram illustrating a process of diagnosing pathologies by using a signal analyzer 202 configured to process initial data 204 comprising patterns defining a pathology for identifying said patterns by comparison with one or more predefined recorded patterns. The build model 202 is developed using a training model 206 by employing training data 208, as well as by providing the results of the build model 202 as a feedback 210 to the training model 206. The feedback 210 enables the training model 206 to learn to recognize diagnostic patterns and develop into a use model 212. The use model 212 identifies diagnostic patterns, in any new input data 214, by comparison, and provides results 216 conveying if a pathology such as 'migraine' is present in the data 214 or not.

Figure 3:
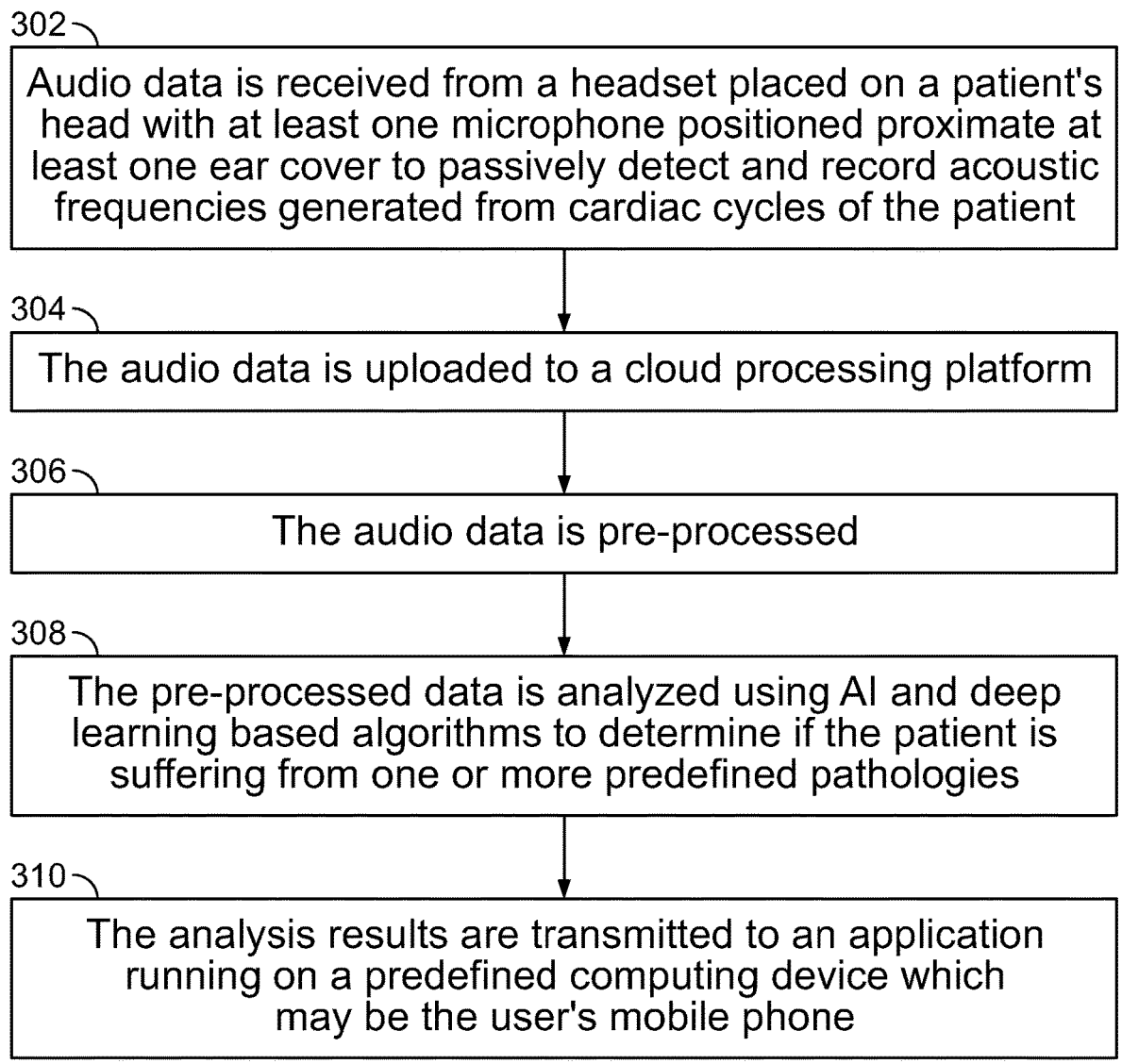
FIG. 3 is a flow diagram illustrating a data flow during the process of diagnosing a pathology in a patient, in accordance with an embodiment of the present specification.

FIG. 3 is a flow diagram illustrating a data flow during the process of diagnosing a pathology in a patient, in accordance with an embodiment of the present specification. At step 302 audio data is received from a headset placed on a patient's head with at least one accelerometer or microphone positioned within 1 foot of the patient's ear. In a preferred embodiment, at least one microphone is positioned within each ear cover of the headset to passively detect and record vibrations generated by blood flow within a patient's brain from cardiac cycles of the patient.

At step 304, the captured audio data is digitized and transmitted to a cloud processing platform. In an embodiment, the audio data is stored in a mobile application, which in turn uploads the data to the cloud processing platform. Next the data is pre-processed at step 306. In an embodiment, the audio data is cleaned by applying noise reduction techniques to obtain clean audio patient data. In an alternate embodiment, the audio data is processed at a local device and then uploaded to a cloud platform.

In an embodiment, audio data may be processed via a beamforming technique. In this technique, two microphones would be employed in each ear, forming a beam of interest. In an embodiment, beamforming can be used to remove noise by attenuating all noises in the environment and focusing on the narrow beam pointing towards the ear canal to extract the signal of interest. In this embodiment, noise is not removed from the signal, rather any signal that falls outside of the beam of interest, and therefore any signal that is not coming directly from the ear canal, would be cancelled.

The cleaned or scrubbed audio data is then processed to obtain spectrograph images. At step 308 the pre-processed data is analyzed using AI and deep learning-based algorithms to determine if the patient is suffering from one or more predefined pathologies. At step 310 the results are transmitted to an application running on a predefined computing device which may be the user's mobile phone.

Figure 4A:
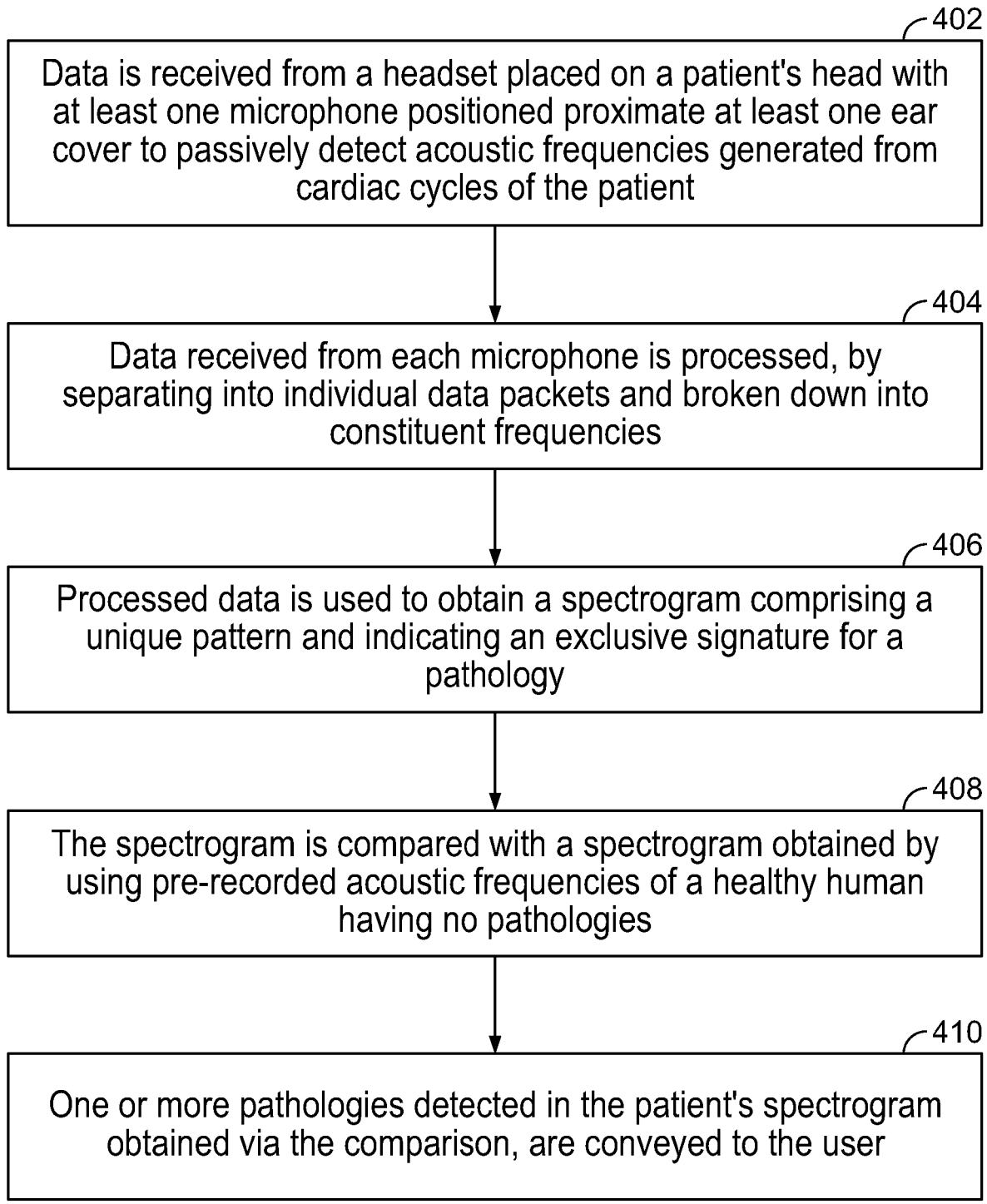
FIG. 4A is a flow chart illustrating a method of diagnosing and treating a plurality of pathologies in a patient, in accordance with an embodiment of the present specification.

The method of determining and displaying pathologies corresponding to a patient's acoustic data is further described with reference to FIG. 4. FIG. 4A is a flow chart illustrating a method of diagnosing and treating a plurality of pathologies in a patient, in accordance with an embodiment of the present specification. At step 402 data is received from a headset placed on a patient's head with one microphone positioned within each ear cover to passively detect vibrations generated from cardiac cycles of the patient. In an embodiment, the microphones passively receive vibrations generated by the vasculature of the brain. In an embodiment, the acoustic data comprises signals having a frequency above 150 Hz. In some embodiments, the acoustic data comprises signals having a frequency range between 20 Hz and 200 Hz. In other embodiments, the acoustic data comprises signals having a frequency range greater than 200 Hz. In some embodiments, the acoustic data comprises signals having a frequency range between 200 Hz and 750 Hz. In various embodiments, signals are analyzed in the frequency domain and as a function of time.

At step 404 the data received from each microphone is processed. In an embodiment, the received data is separated into individual data packets and decomposed into constituent frequencies using any known data transformation algorithm such as but not limited to Fourier transform, wherein the frequencies and the amplitude of the received vibrations are examined as a function of time. In various embodiments the data received from each microphone may be used to generate unique patterns and features that may indicate an exclusive signature for different pathologies. The vibrations obtained from the cardiac cycle (diastole & systole) range from a normal baseline of approximately 15-20 Hz and shift further down the spectrum to approximately 30 to 80 Hz, depending on the pathology being assessed.

At step 406 the processed data is used to obtain a spectrograph comprising a unique pattern and indicating an exclusive signature for a pathology. In an embodiment, the processed data comprises predefined frames of audio signals having frequencies ranging from approximately 150 Hz to 1000 Hz. In an embodiment, a sum of all energies within said range is computed with respect to each frame to obtain a spectrograph of the captured data.

At step 408 the spectrograph is compared with a spectrograph obtained by using pre-recorded vibrations of a healthy human having no pathologies. In various embodiments, the patient's spectrograph may be compared with a plurality of pre-recorded spectrographs for determining if any of a set of pre-defined pathologies are present in the patient's acoustic data. In an embodiment, the time, frequency and amplitude of vibrations generated by the vasculature of the brain of the patient are compared with those of a healthy human or of humans with specific pathologies, such as tension headaches, migraines, depression, dementia, Alzheimer's disease, epilepsy, Parkinson's disease, autism, cerebral vasospasm and meningitis.

In various embodiments the comparison of the patient's spectrograph with other spectrographs to obtain if the patient suffers from any of a plurality of pre-defined pathologies is achieved in the signal analyzer by using artificial intelligence (AI), machine learning or pattern recognition based algorithms. In an embodiment, distinctive acoustic patterns and frequencies generated from a pathology, if present in a patient's spectrograph, are identified by using AI, machine learning and pattern recognition-based algorithms. In an exemplary embodiment, the spectrograph of a patient suffering from migraine is analyzed with respect to a spectrograph of a person not suffering from migraines. In various embodiments, specific types of migraines (with Aura, without Aura, Basilar, Hemiplegic, Ophthaloplegic, Vestibular or Chronic) can be detected by analyzing vibration spectrographs by using the signal analyzer.

Accordingly, referring to FIG. 1F, the data tier 114 comprises a plurality of databases, including enterprises databases 141, big data 143, and/or an audio session aggregator 145 that receives, stores, and/or catalogs signal signatures, spectrographs, frequency windows, and/or data patterns, each of which is indicative of a different migraine type, such as Aura, without Aura, Basilar, Hemiplegic, Ophthaloplegic, Vestibular or Chronic. Additionally, in other embodiments, the data tier 114 comprises a plurality of databases, including enterprises databases 141, big data 143, and/or an audio session aggregator 145 that receives, stores, and/or catalogs signal signatures, spectrographs, frequency windows, and/or data patterns, each of which is indicative of a different non-traumatic brain condition, including, but not limited to, depression, vascular dementia, Alzheimer's disease, epilepsy, vascular Parkinson's, autism, cerebral vasospasm, and/or meningitis.

At step 410 one or more pathologies detected in the patient's spectrograph are displayed to the user via a GUI running on a computing device. In an embodiment, the signal analyzer detects the features of the waveform and provides a qualitative and quantitative diagnostic output to assess if the patient has the pathology or not. In an embodiment, the qualitative output is a simple stop light where green is no pathology present, yellow is pathology below a threshold level present and red is pathology above a threshold present. In other embodiments, a quantitative number, on a scale of 1 to 10 is displayed to describe the severity of the detected pathology.

Figure 4B:
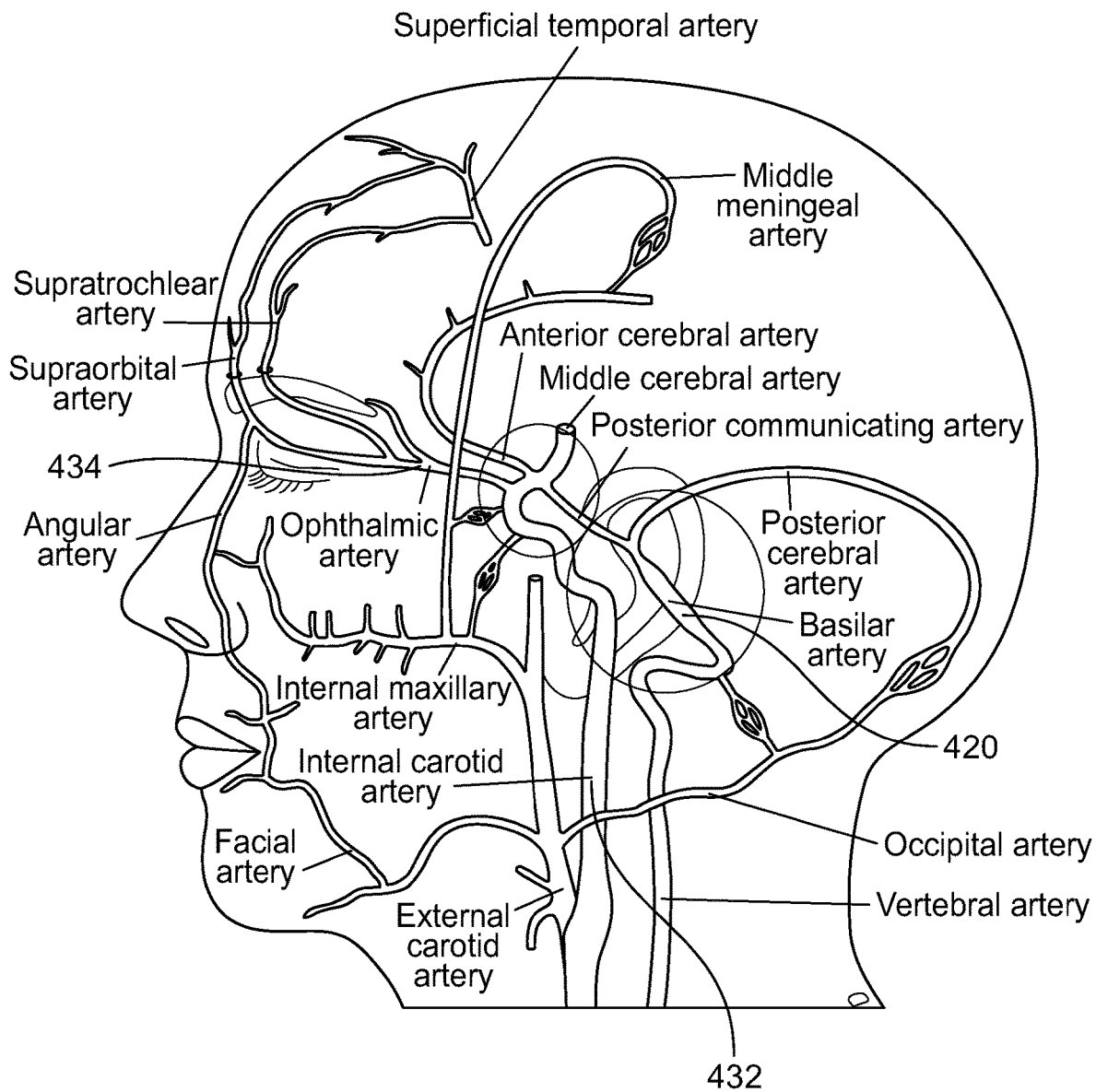
FIG. 4B illustrates flow of blood through arteries in a person's head.
Figure 4C:
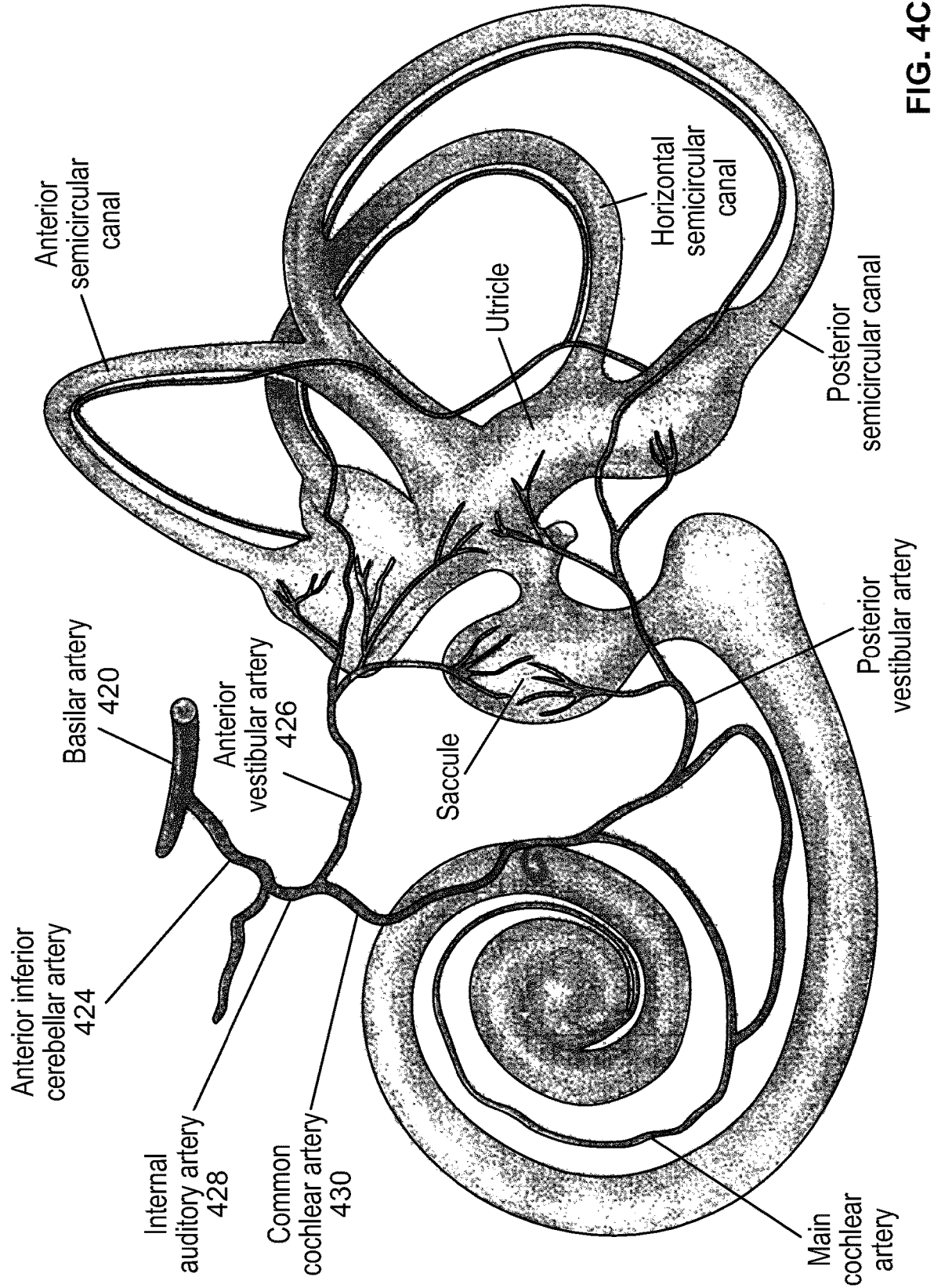
FIG. 4C is diagrammatic representation of the arteries carrying blood to a person's head.

In various embodiments, cerebral vasculature response (vasodilation and vasoconstriction), byproducts of the underlying migraine condition, can be measured and identified. Since the human heart pumps blood bilaterally to the brain through the carotid arteries, pumping of the heart, along with asymmetric blood flow, pulses the blood through the cerebral blood vessels. FIG. 4B illustrates flow of blood through arteries in a person's head. FIG. 4C is diagrammatic representation of the arteries carrying blood to a person's head. Since the human heart pumps blood bilaterally to the brain through the carotid arteries, pumping of the heart, along with asymmetric blood flow, pulses the blood through the cerebral blood vessels. In various embodiments, cerebral vasculature response (vasodilation and vasoconstriction), are measured via such cerebral arteries, and identified.

Referring to FIGS. 4B and 4C, a patient's cerebral vasculature response may be measured via the basilar artery 420, the anterior inferior cerebellar artery 424, the anterior vestibular artery 426, the internal auditory artery 428, the common cochlear artery 430, the internal carotid artery 432, the ophthalmic artery 434, or the branches of any of the aforementioned arteries ("Target Cerebral Vasculature"). In embodiments, cerebral vasculature response may be measured via said arteries by placing a sensor within the ear canal of the person or within a predefined distance from a wall of one or more of the Target Cerebral Vasculature. In one embodiment, the predefined distance is within 0 mm to 20 mm, preferably within 0 mm to 10 mm, and more preferably within 0 mm to 5 mm, or any increments therein.

In contrast, it is preferred to avoid placing sensors in locations that would result in the detection of peripheral blood flow, which is not indicative of the actual cerebral vasculature. Such locations may include above the zygoma which is the bony arch of the cheek formed by connection of the zygomatic and temporal bones of the person, the external carotid artery, the internal maxillary artery, the facial artery, the occipital artery or the branches of any of the aforementioned arteries ("Non-Target Peripheral Vasculature"). In particular, it is preferable to place a sensor outside of a predefined distance from a wall of one or more of the Non-Target Peripheral Vasculature. In one embodiment, the predefined distance is outside of 20 mm, preferably outside of 10 mm, more preferably outside of 5 mm, even more preferably outside of 2 mm, or any increments therein.

Therefore, it is important to position the sensors in a location and configuration where the primary signals being received by the sensors are indicative of the acoustic properties of blood flow through the Target Vasculature and not indicative of the acoustic properties of blood flow through the Non-Target Vasculature. In one embodiment, one, more than one, or all of the sensors are physically positioned closer to at least one of the Target Cerebral Vasculature relative to each of the Non-Target Peripheral Vasculature. In one embodiment, one, more than one, or all of the sensors are physically positioned within 5 mm of a wall of at least one of the Target Cerebral Vasculature and further than 5 mm from each of the Non-Target Peripheral Vasculature. In one embodiment, one, more than one, or all of the sensors are physically positioned within 10 mm of at least one of the Target Cerebral Vasculature and further than 10 mm from each of the Non-Target Peripheral Vasculature. In one embodiment, one, more than one, or all of the sensors are physically positioned within 0 mm to 5 mm of at least one of the Target Cerebral Vasculature and further than 5 mm from each of the Non-Target Peripheral Vasculature.

Figure 4D:
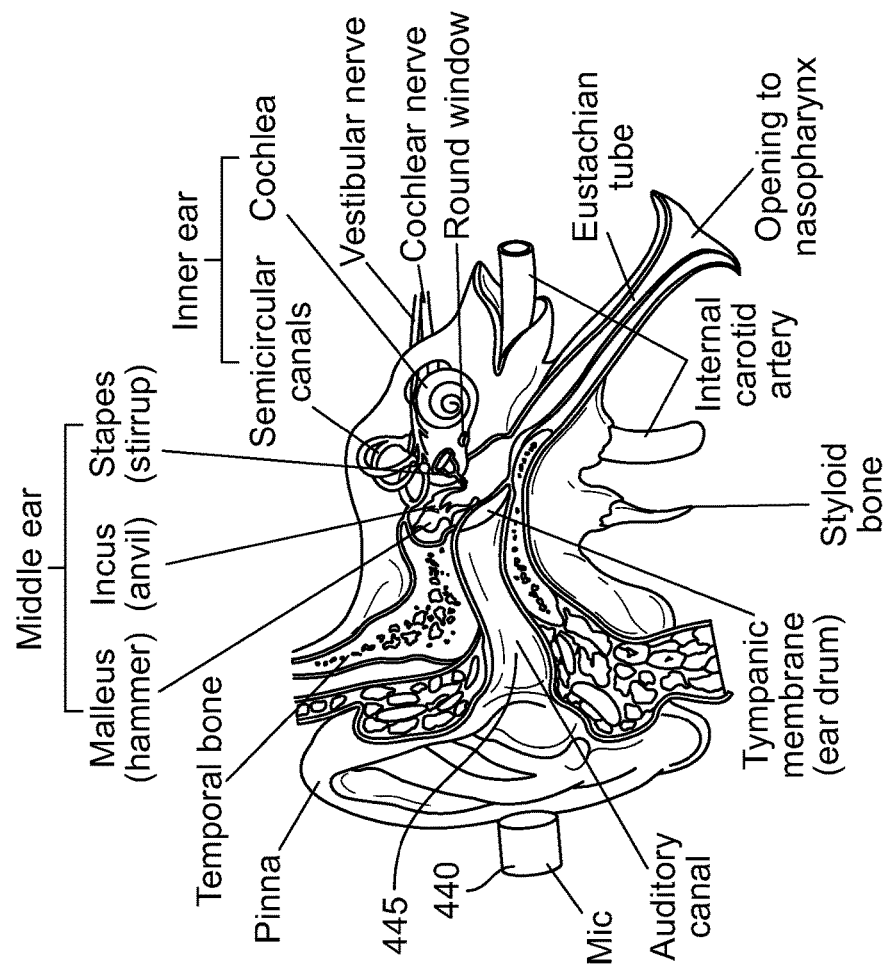
FIG. 4D illustrates microphones placed near the ear canal of a person, in accordance with an embodiment of the present specification.
Figure 4E:
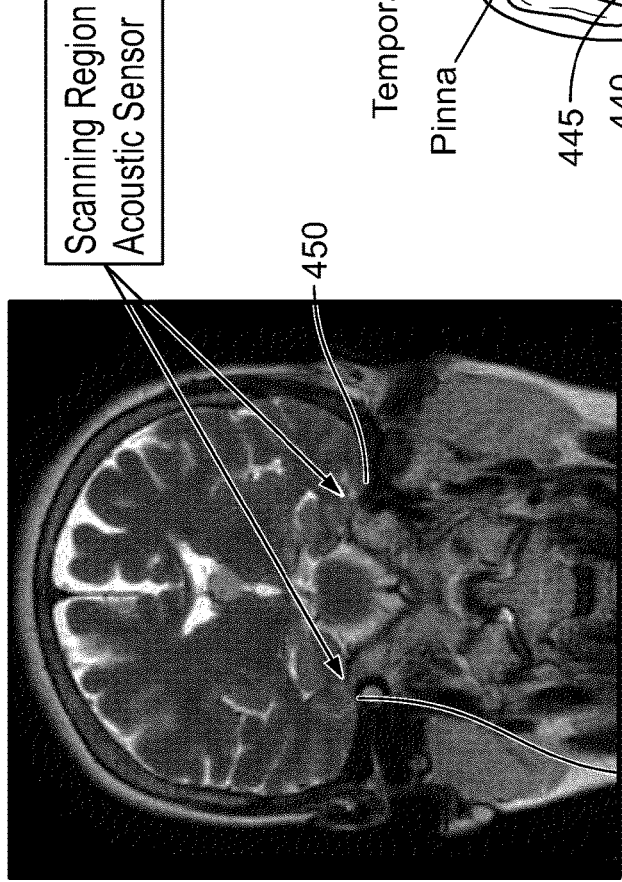
FIG. 4E illustrates scanning regions of acoustic sensors within the brain of a person, in accordance with an embodiment of the present specification.

In an embodiment, the pulsation of blood through artery walls is picked up by sensitive microphones placed near the ear canal. FIG. 4D illustrates microphones 440 placed near the ear canal 445 of a person, in accordance with an embodiment of the present specification. FIG. 4E illustrates scanning regions 450 of acoustic sensors within the brain of a person, in accordance with an embodiment of the present specification. It has been observed that pulsation of blood through the cerebral vasculature is impacted by migraine in a predictable way. Hence, in various embodiments, the vibration from patients suffering from migraine are analyzed by using the signal analyzer, classified, and the results provided to the clinician In embodiments, where cerebral vasculature response is measured via the ophthalmic artery 434, a sensor may be placed over closed eyelids of the person. It is to be noted that in various embodiments, the cerebral vasculature response is measured via internal arteries within the head of a person and not via peripheral arteries which can be felt pulsating via the forehead of the person. Prior art discloses acquiring signals from superficial arteries from the patient's forehead and comparing the signal to a reference signal indicative of peripheral vasculature (radial artery), which is a completely different method than that disclosed in the present specification. It is not possible to passively capture a signal indicative of cerebral vasculature from a person's forehead. Hence, the present specification discloses alternate locations (such as, but not limited to those disclosed above) for placement of sensors for collecting the cerebral vasculature response. It should be appreciated, therefore, that the microphone in the present invention is positioned to acquire signals that are more indicative of the cerebral vasculature of the patient's brain than of the peripheral vasculature of the patient's brain. In one embodiment, it is preferred to position the microphone, sensor, and/or accelerometer away from peripheral vessel structures such as, but not limited to, the superficial temporal artery and proximal branches (terminal branches of the internal carotid artery, supratrochlear artery, supraorbital artery).

In an embodiment a reference sensor is employed to enable removal of signals from non-cerebral sources, such as but not limited to peripheral arteries. In other embodiments, no reference sensor is employed, no reference signal is used to generate the signatures described herein, or no reference signal indicative of a patient's arterial or radial blood flow is used to generate the signatures described herein.

Figure 4F:
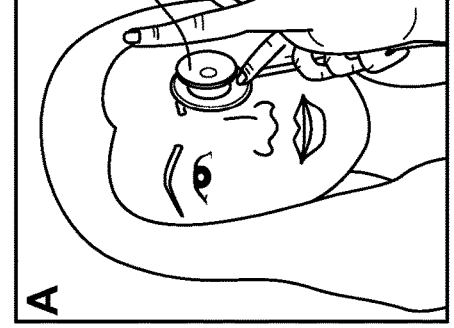
FIG. 4F illustrates a method of performing ocular auscultation.

In an embodiment, cerebral vasculature response may be measured via the ophthalmic artery of a person by using retinal sensing methods. In an embodiment, ophthalmic artery response is measured by using a stethoscope over closed eyelids of a person. Ocular auscultation is a physical exam maneuver that consists of listening to the vascular sounds of the head and neck by placing the stethoscope on the surface of the eyelids and surrounding structures. FIG. 4F illustrates a method of performing ocular auscultation. As shown in FIG. 4F the bell of a stethoscope 460 is gently placed over a patient's closed eye. To minimize the sound produced by eyelid tremor, the patient is asked to stare at a fixed point while the examiner gently closes one of the eyes and firmly places the stethoscope over the closed eye.

In an embodiment, electronic stethoscopes may be used for ocular auscultation. A conventional problem with acoustic stethoscope is that the sound level captured may be very low. A low sound level may be overcome by using digital stethoscopes which amplify the low sounds or 'bruits' captured from the eye. An electronic stethoscope converts the acoustic sound waves obtained through the 'chest piece' of the stethoscope into electronic signals which are then transmitted from specially designed circuits and processed for best hearing and also allow the energy to be amplified and optimized for listening at various different frequencies. The circuitry also allows the sound energy to be digitized, encoded and decoded, to have the ambient noise reduced or eliminated, and sent through speakers or headphones or transmitted for further processing.

Figure 5A:
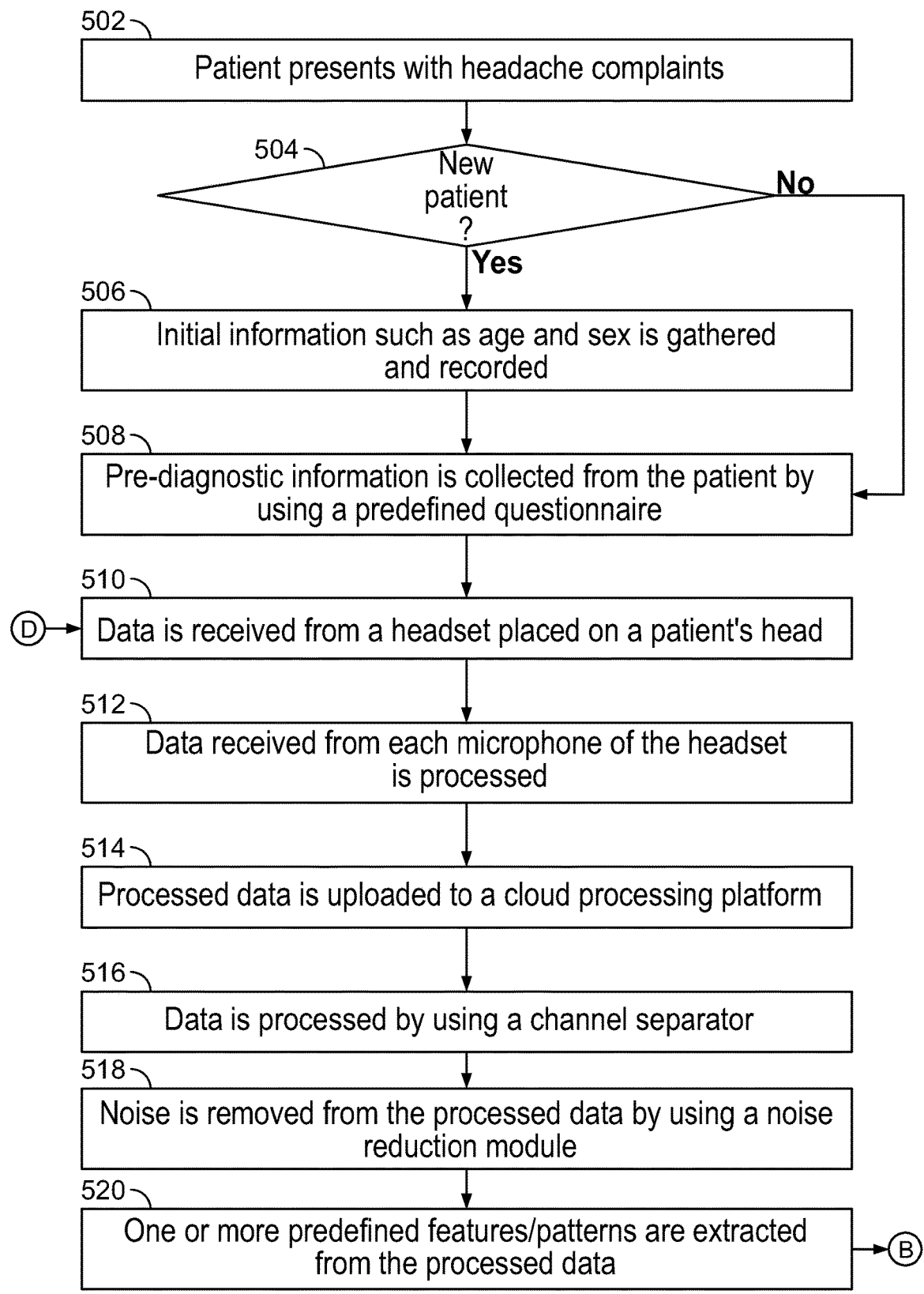
FIG. 5A is a flowchart illustrating the steps of diagnosing and treating a migraine in a patient, in accordance with an embodiment of the present specification.

Referring back to migraines, a migraine may be caused by a neurogenic disorder causing a secondary change in cerebral profusion associated with neurogenic inflammation. These changes in cerebral profusion produce identifiable vibration that are analyzed by the signal analyzer, classified, and the results provided to the clinician FIG. 5A is a flowchart illustrating the steps of diagnosing and treating a migraine in a patient, in accordance with an embodiment of the present specification. At step 502 a patient presents with a general, undiagnosed headache. At step 504 it is determined if the patient is a new patient or already registered with the diagnostic system of the present specification. If the patient is a new patient, at step 506 initial information regarding the patient's age and sex, and other demographic data, is captured and recorded in a database. Next, at step 508, pre-diagnostic information is collected from the patient by using a predefined questionnaire.

In an embodiment, the questionnaire comprises questions, such as but not limited to:

1. How many migraines do you experience each month on average?
2. How many regular headaches do you have per month on average?
3. How long do your migraine headaches usually last after you take migraine medicine?
    a. 2 hrs.; b. 3-4 hrs; c. 5-12 hrs; d. 12-24 hrs; e. several days; f. 1 week or longer
4. How long do your migraine headaches last if you do not take your migraine medicine?
    a. 2 hrs.; b. 3-4 hrs; c. 5-12 hrs; d. 12-24 hrs; e. several days; f. 1 week or longer

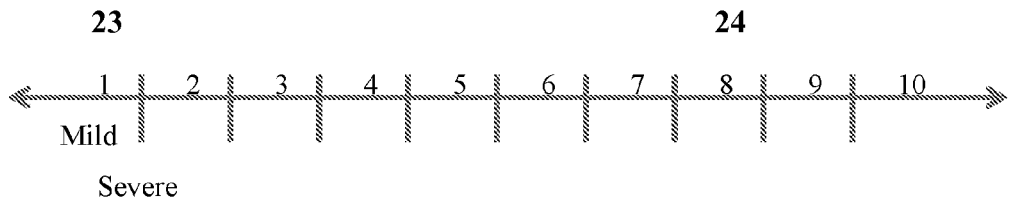

6. Where is your migraine headache usually located? (Circle all the apply and indicate which area hurts the most.)

Above/behind the eye   Right  Left  Both  Other       Areas: _____

Temporal Area          Right  Left  Both

Occipital/Back of Head  Right  Left  Both  Area that hurts the most: _____

7. How old were you when your migraine started?
8. How would you describe your migraine headaches?

Throbbing/pounding  Ache/pressure  Like a tight band    Dull
    Other

9. Do your migraine headaches awaken you at night?

Never      Occasionally      Often

10. Do any of the following occur before or during your migraine headaches? (Check all that apply)

| | | |
|---|---|---|
| Nausea  Vomiting | Diarrhea | |
| Bothered by light/noise | Blurred/double vision | Sparkling, flashing, or colored lights |
| Eyelid puffy | Eyelid droops | Loss of vision |
| Feeling lightheaded | Numbness / tingling | Weakness of arm or leg |
| Difficulty concentrating | Speech difficulty | Loss of consciousness |
| Runny nose | Other_____ | |

11. Do any of the following bring on your migraine headaches or make them worse? (Check all that apply)

Stress (worry, anger)      Bright Sunshine      Weather change

Letdown" after stress      Loud noise      Heavy lifting

Air travel      Fatigue      Certain smells or perfume

Missed meals      Sexual activity      Coughing, straining, bending over

Certain foods (chocolate, cheese, beer, MSG)      Other

12. Do any of the following make your migraine headaches better?

Rest      Exercise      Quiet and darkness

Hot or cold compress      Massage      Warm shower

Pressure over migraine headache area      Other

13. If you are female, do your migraine headaches change with the following? (Check all that apply)

Menstrual periods      Birth control pills      Pregnancy
    Other hormonal drugs 14. 14. Have you ever had a head or a neck injury requiring medical treatment?

No      Yes - If "yes", describe: _____

15. 15. Have you ever been diagnosed to have any health disorder (e.g. high blood pressure, asthma, heart disease, gastric ulcers)?

No      Yes - If "yes," please list:

16. Have you had your migraine headaches evaluated by a neurologist? No    Yes - If "yes", when, where, and by whom?

What was the diagnosis? (Check all that apply):

Migraine       Tension-type       Cluster       Other, specify —

17. List all past tests you had for your migraine headaches:

MRI Brain/Neck/Both (circle: Brain / Neck / Both)
    MRI w/contrast   MRI w/o contrast    CT Scan       EEG
    Sleep Study Other: _____ When/How long ago:

18. List all past treatment(s) for your migraine headaches:

Botox       Nerve Block       IV Meds Medication
    Other Preventatives:

19. Have you had Botox to treat your migraines in the past?   No   Yes - If so, how many treatments did you receive and what was the dosage? _____ What kind of relief did you get?   Complete   Partial   None How long did the relief last? _____

20. Which Medications are or have you taken?

| Abortive | Past | Current | Preventative | Past | Current | Other | Past | Current |
|---|---|---|---|---|---|---|---|---|
| Triptan | | | Topamax | | | | | |
| Maxalt | | | Valproic Acid | | | | | |
| Relpax | | | Amitriptyline | | | | | |
| Amerge | | | Topiramate | | | | | |
| Zomig | | | Beta Blockers | | | | | |
| Imitrex | | | Inderal | | | | | |
| Frova | | | Lopressor | | | | | |
| Fiorinal/Fioricet | | | Propranolol | | | | | |

| Ergots | | Anti-Depressants | | | | | |
|---|---|---|---|---|---|---|---|
| Axert | | Other Blood Pressure | | | | | |
| Treximet | | Other Anti-Depressants | | | | | |

21. Are you taking any over-the-counter drugs to treat your migraine headaches?   No   Yes - If "yes", list the medications under the "Other List" column above and how many times in the last month have you used the over-the-counter medications? _____

22. Have you been treated for a psychiatric condition, if so what condition and when was the last treatment? _____

23. Have you had hormone or vitamin levels checked? No Yes - If "yes", list when and the results.

24. Have you been treated for sinus or other related issues such as deviated septum? No Yes - If "yes", list the treatment provided. _____

25. Do you have numbness or tingling in the hands and/or neck? No Yes

26. How would you rate your general health in the last month? (Check one)   Excellent   Good   Fair   Poor 27. To what extent do your migraine headaches affect your quality of life? (Check one)

Extremely   Moderately   Very little   Not at all

28. Have you suffered from a head trauma or injury?   No   Yes - If "yes", state the nature of the injury, when the injury occurred and treatment provided. _____

29. Have you been diagnosed with or had the following treatments within the past year? If so when/how often? Eye exam _____ TMJ _____ Snore _____ Wear mouth guard _____ Wake up w/migraine _____ Wear CPAP _____ Have seizures _____ Other _____

List any other medical condition, injury or concern not previously asked above that you feel we should know about.

In various embodiments, the patient's response to the questionnaire is automatically analyzed using the signal analyzer to provide predictive analytics as an additional feature to the diagnostic system of the present specification, further enhancing the accuracy, sensitivity, or specificity of a migraine diagnosis. Moreover, the data captured on a single patient can be compared to that of recorded responses of other patients to obtain a goal-directed therapy for the patient. In an exemplary scenario, a pre-treatment questionnaire may be used to query similar patient profiles and help detect patterns around food allergies. For example, it is documented that migraine can be caused by food allergies. By providing similar cases, the signal analyzer may direct a physician to instruct a patient to avoid the determined foods causing allergies.

At step 510 data is received from a headset placed on a patient's head with at least one accelerometer or one microphone positioned within at least one of the headset ear covers to passively detect and record vibrations generated from cardiac cycles of the patient. In an embodiment, the microphone or accelerometer passively receives vibrations generated by the vasculature of the brain. In an embodiment, the headset converts any changes in pressure caused by the pulsation of the blood through the vessel walls to electrical energy using the microphone or accelerometer placed near the ear canal of the patient. In an embodiment, due to the sensitivity required to measure the changes in pressure, the patient is placed in an environment with noise contributing equipment turned off and lighting minimized for detecting and recording the vibrations.

At step 512 the data received from each microphone of the headset is processed by audio processing APIs (Application Processing Interface), which are responsible for digitizing the audio data. At step 514 the processed data is uploaded to a cloud processing platform. In an embodiment, the data generated from each microphone of the headset is stored in a mobile application, where it is processed by using the audio processing APIs, and is then uploaded to the cloud processing platform at step 514. Because there are two microphones on different channels, the data may be captured and processed separately or the data is separated into unique channels and processed separately. At step 516, the data from each microphone is processed by using a channel separator. At step 518, noise is removed from the processed data by using a noise reduction module comprising a database of classified and identified noises that may be present in the environment when a patient's recording is made, such as, but not limited to noises caused by air conditioning (AC), electric lights, overhead lights, microphone, floor creaking, keyboard clicks, respiration, or speech.

Figure 6A:
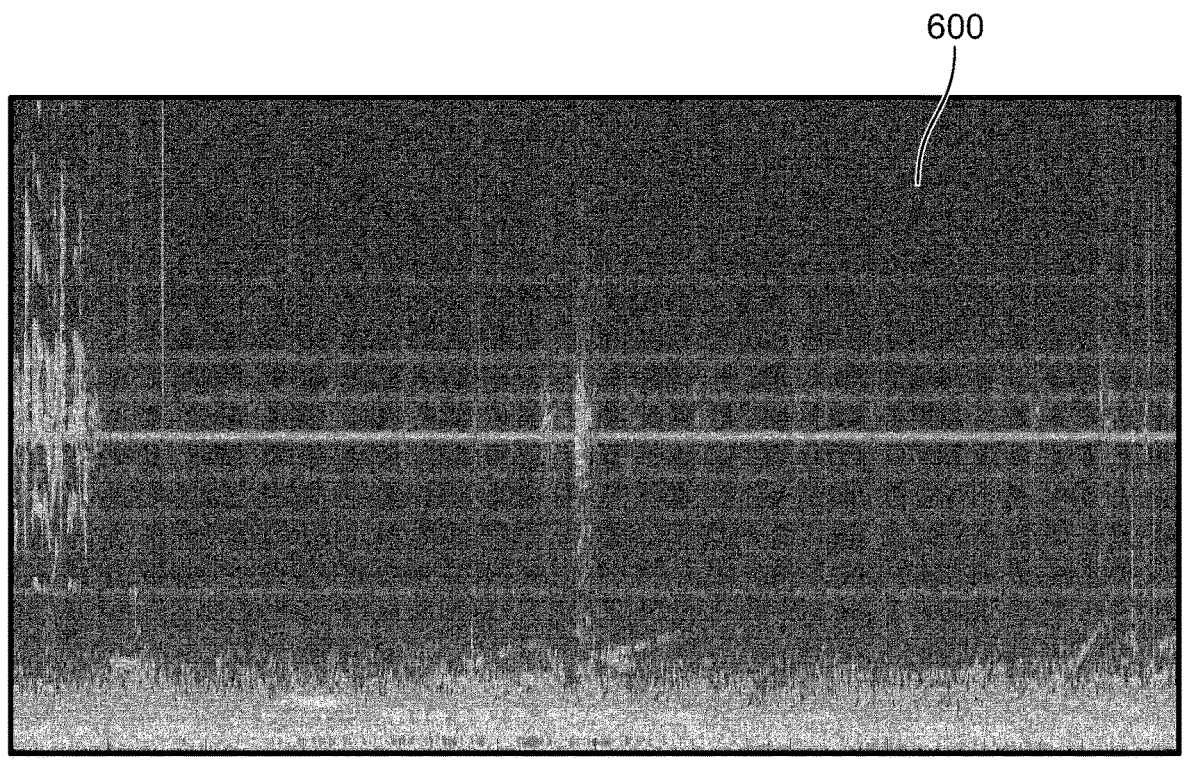
FIG. 6A illustrates a graph classifying identified noises that may be present in the environment when a patient's recording is made, in accordance with an embodiment of the present specification.
Figure 6B:
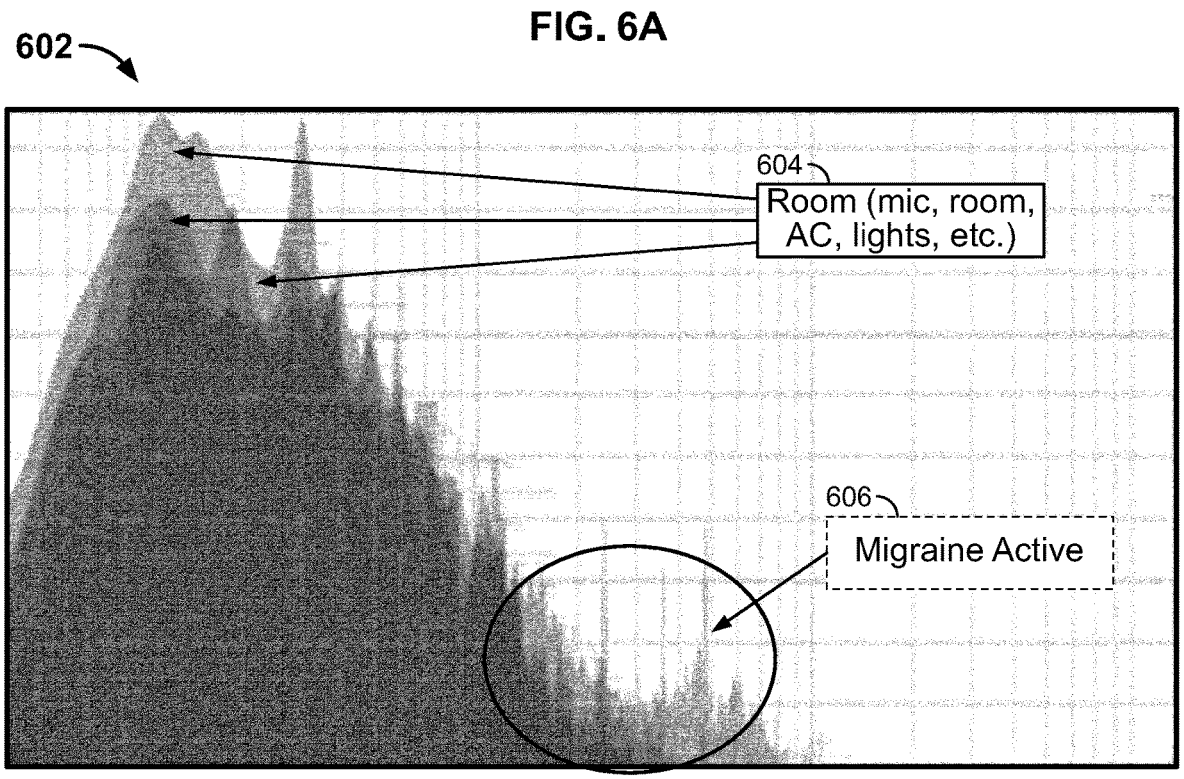
FIG. 6B is a graph illustrating signals of interest from among the identified noises shown in FIG. 6A.

FIG. 6A illustrates a graph 600 classifying identified noises that may be present in the environment when a patient's recording is made, in accordance with an embodiment of the present specification. FIG. 6B is a graph 602 illustrating signals of interest from among the identified noises shown in FIG. 6A. As shown in graph 602, noises 604 captured from the room, such as, but not limited to noises caused by air conditioning (AC), electric lights, overhead lights, microphone, floor, keyboard clicks, respiration, or speech, are then separated from signals 606 of interest, which are generated by the patient suffering from a pathological condition such as migraine.

Figure 6C:
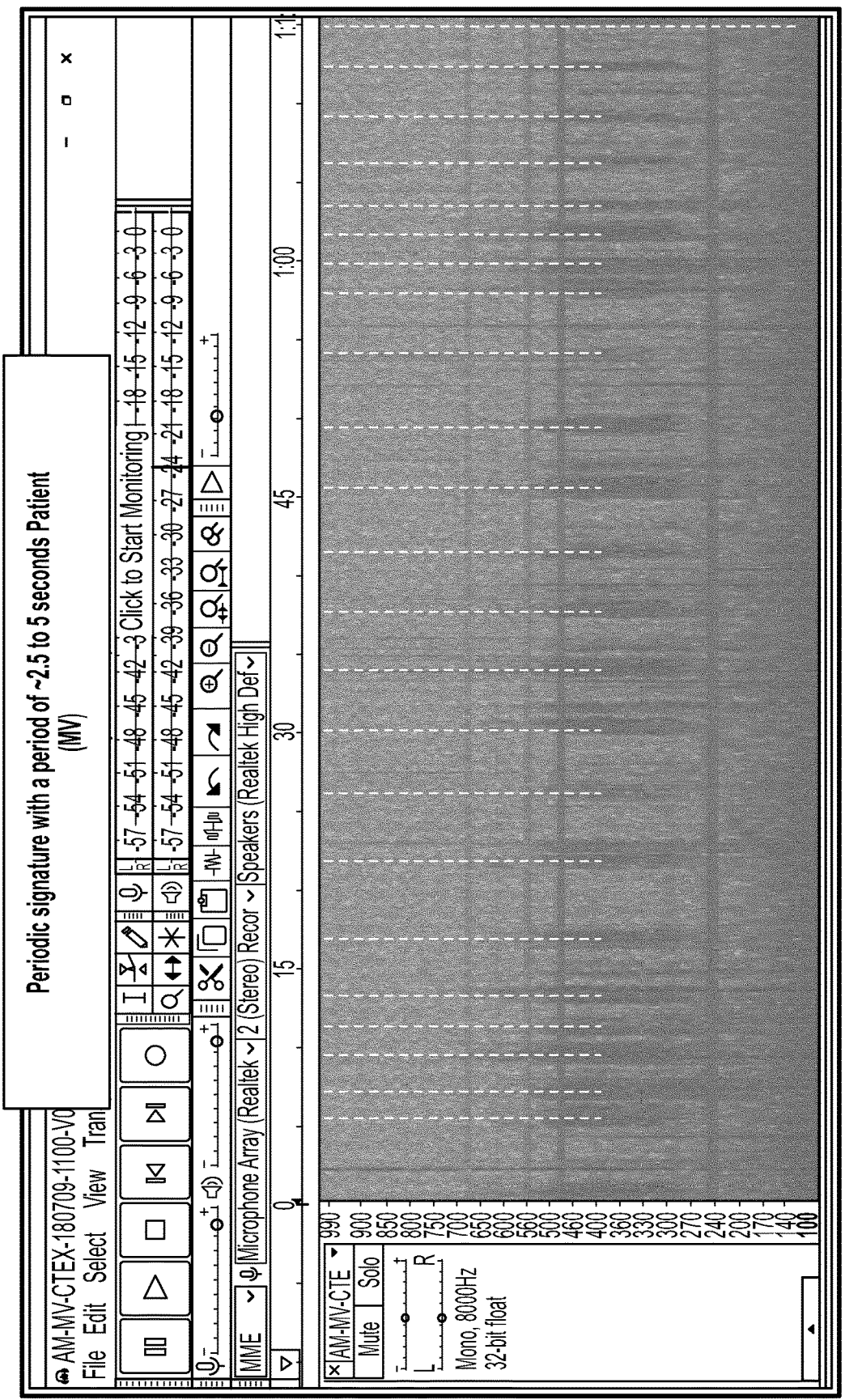
FIG. 6C illustrates periodicity data of a first active migraine patient at periods ranging between 2.5 seconds to 5 seconds, and frequency ranging between 0 Hz-1000 Hz, in accordance with an embodiment of the present specification.

Referring back to FIG. 5A, at step 520 one or more predefined features/patterns such as but not limited to energy, bandwidth and periodicity are extracted from the processed data. In an exemplary case scenario, periodicity of six active migraine patients (Initials: CP, MV, TM, KN, SP, DC), was extracted from the processed data at periods ranging between 1.7 seconds to 5 seconds, and frequency ranging between 0 Hz-1000 Hz. FIG. 6C illustrates periodicity data 608 of a first active migraine patient at periods ranging between 2.5 seconds to 5 seconds, and frequency ranging between 0 Hz-1000 Hz, or more specifically in a range of less than 200 Hz, 200 Hz to 500 Hz, 50 Hz to 200 Hz, or any increment within 5 Hz to 1000 Hz, in accordance with an embodiment of the present specification.

Figure 6D:
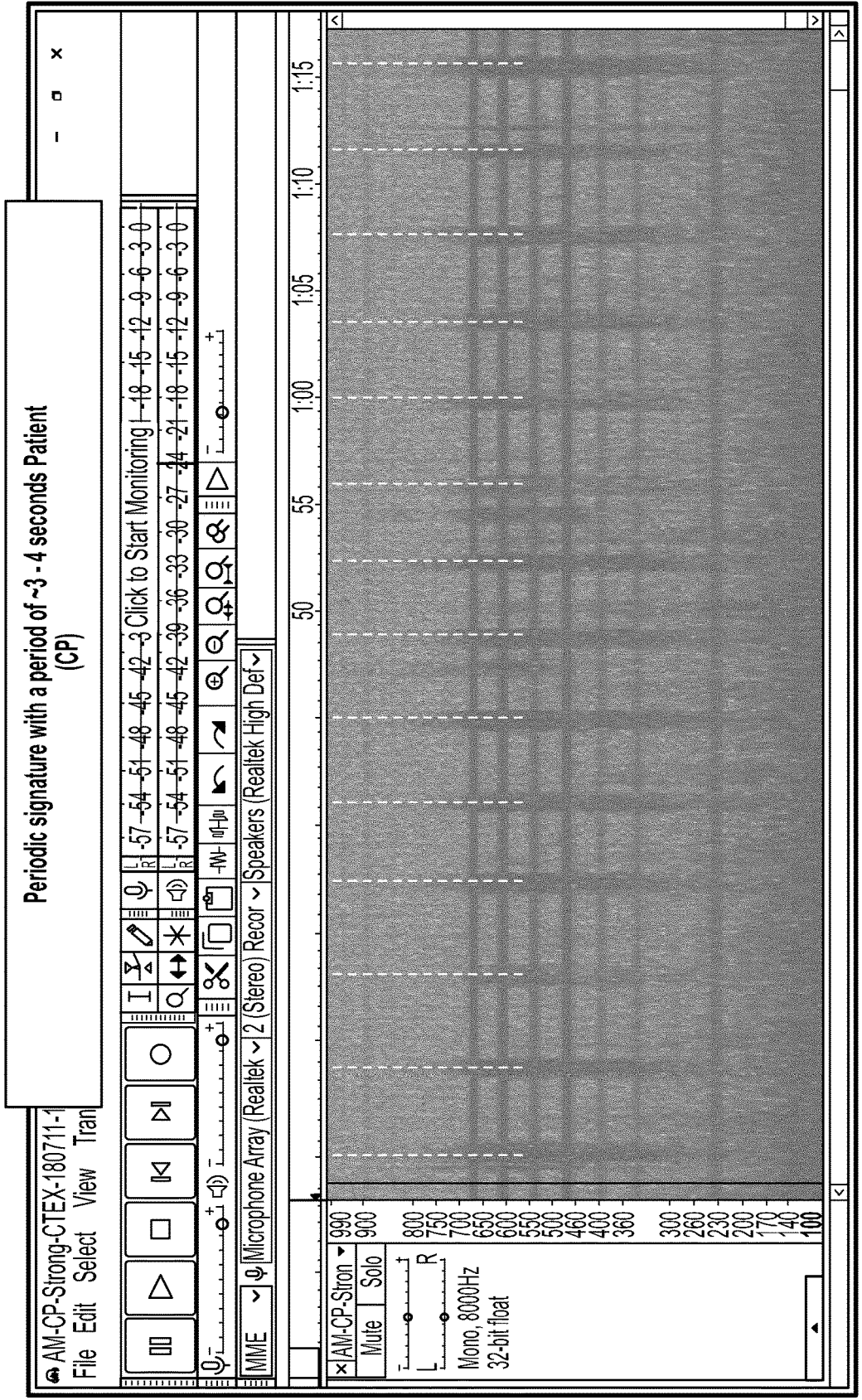
FIG. 6D illustrates periodicity data of a second active migraine patient at periods ranging between 3 seconds to 4 seconds, and frequency ranging between 0 Hz-1000 Hz, in accordance with an embodiment of the present specification.
Figure 6E:
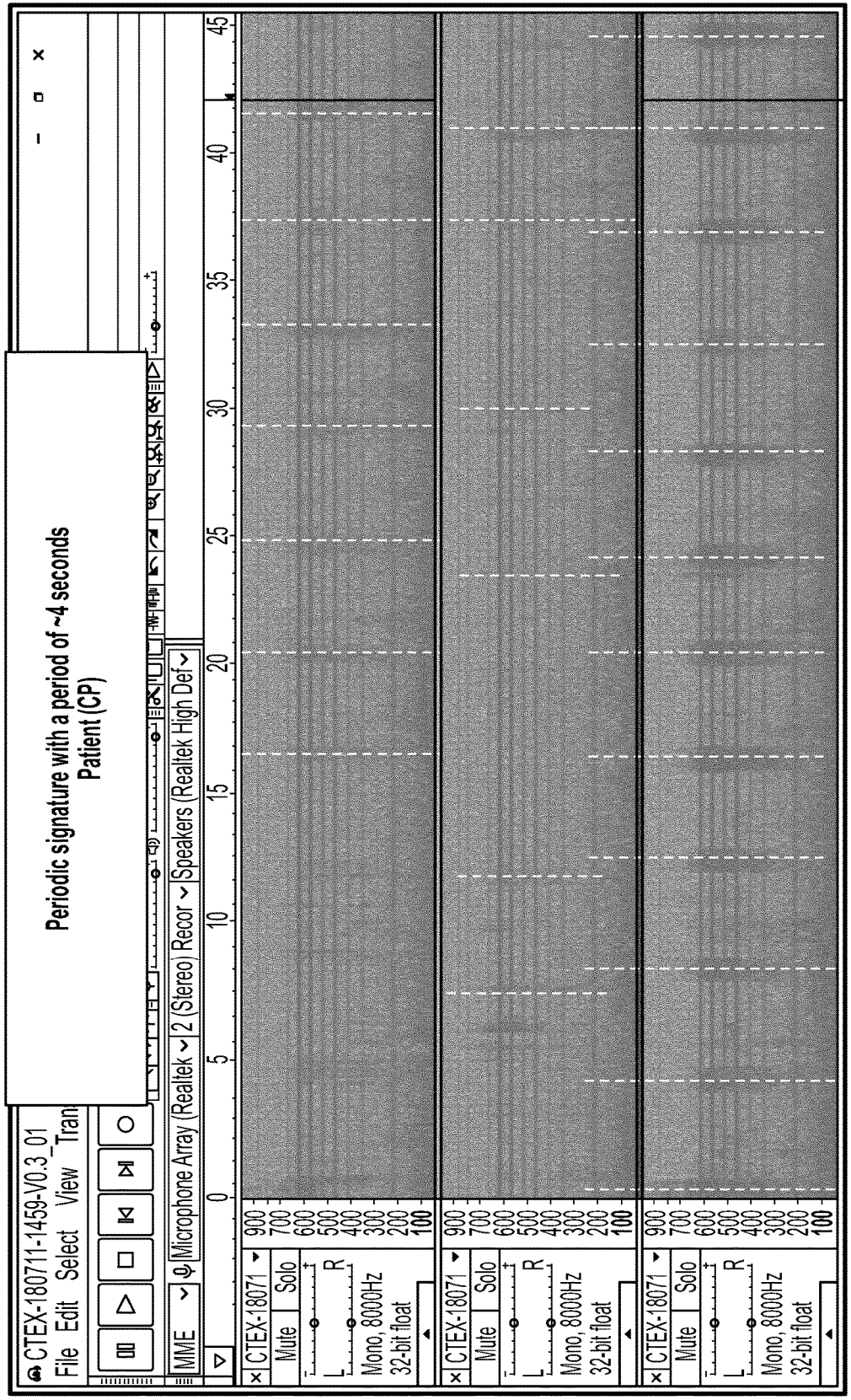
FIG. 6E illustrates periodicity data of a third active migraine patient at periods ranging around 4 seconds, and frequency ranging between 0 Hz-1000 Hz, in accordance with an embodiment of the present specification.

FIG. 6D illustrates periodicity data 610 of a second active migraine patient at periods ranging between 3 seconds to 4 seconds, and frequency ranging between 0 Hz-1000 Hz, in accordance with an embodiment of the present specification. FIG. 6E illustrates periodicity data 612 of a third active migraine patient at periods ranging around 4 seconds, and frequency ranging between 0 Hz-1000 Hz, in accordance with an embodiment of the present specification.

Figure 6F:
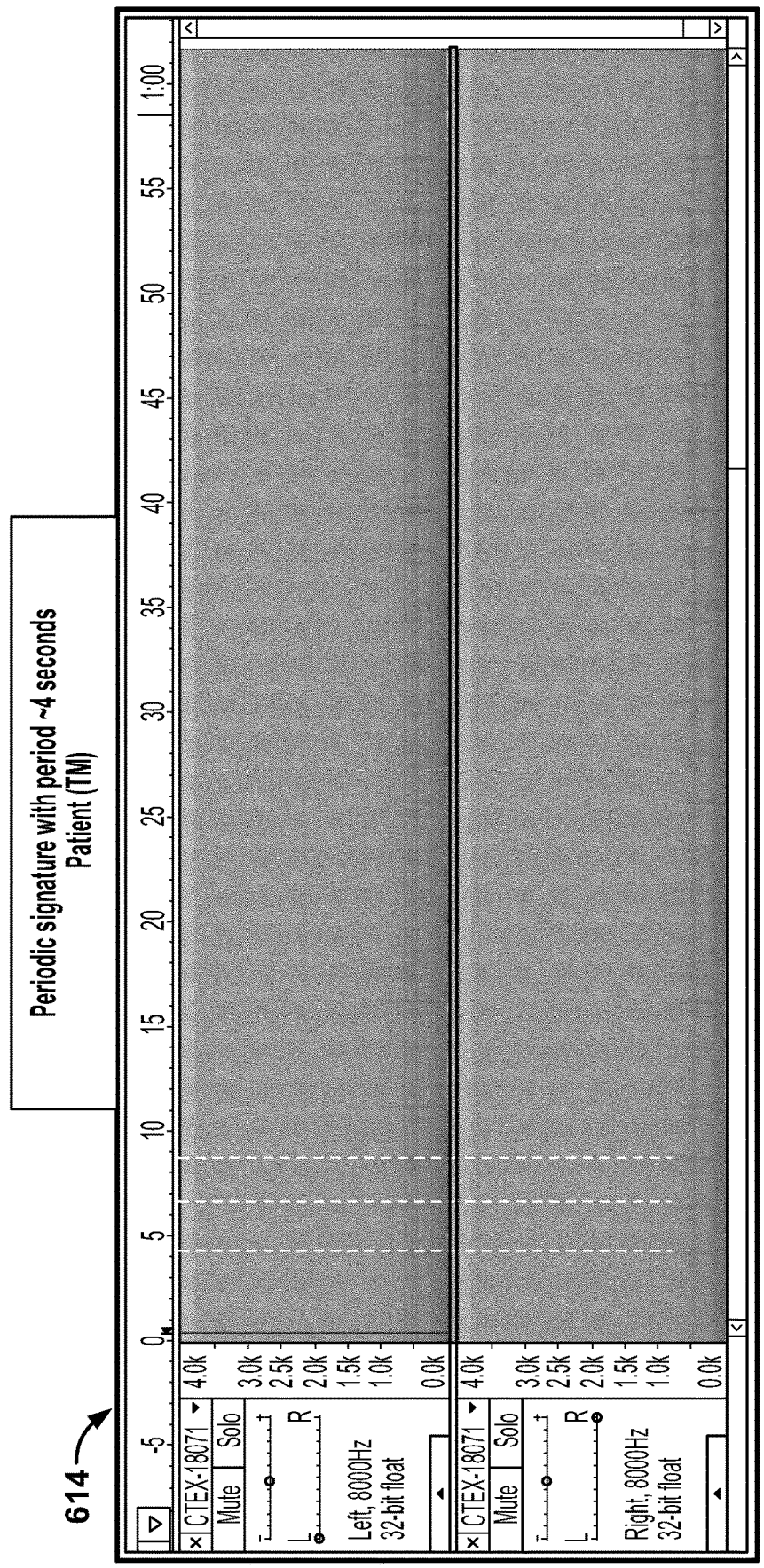
FIG. 6F illustrates periodicity data of a fourth active migraine patient at periods ranging around 4 seconds, and frequency ranging between 0 Hz-1000 Hz, in accordance with an embodiment of the present specification.
Figure 6G:
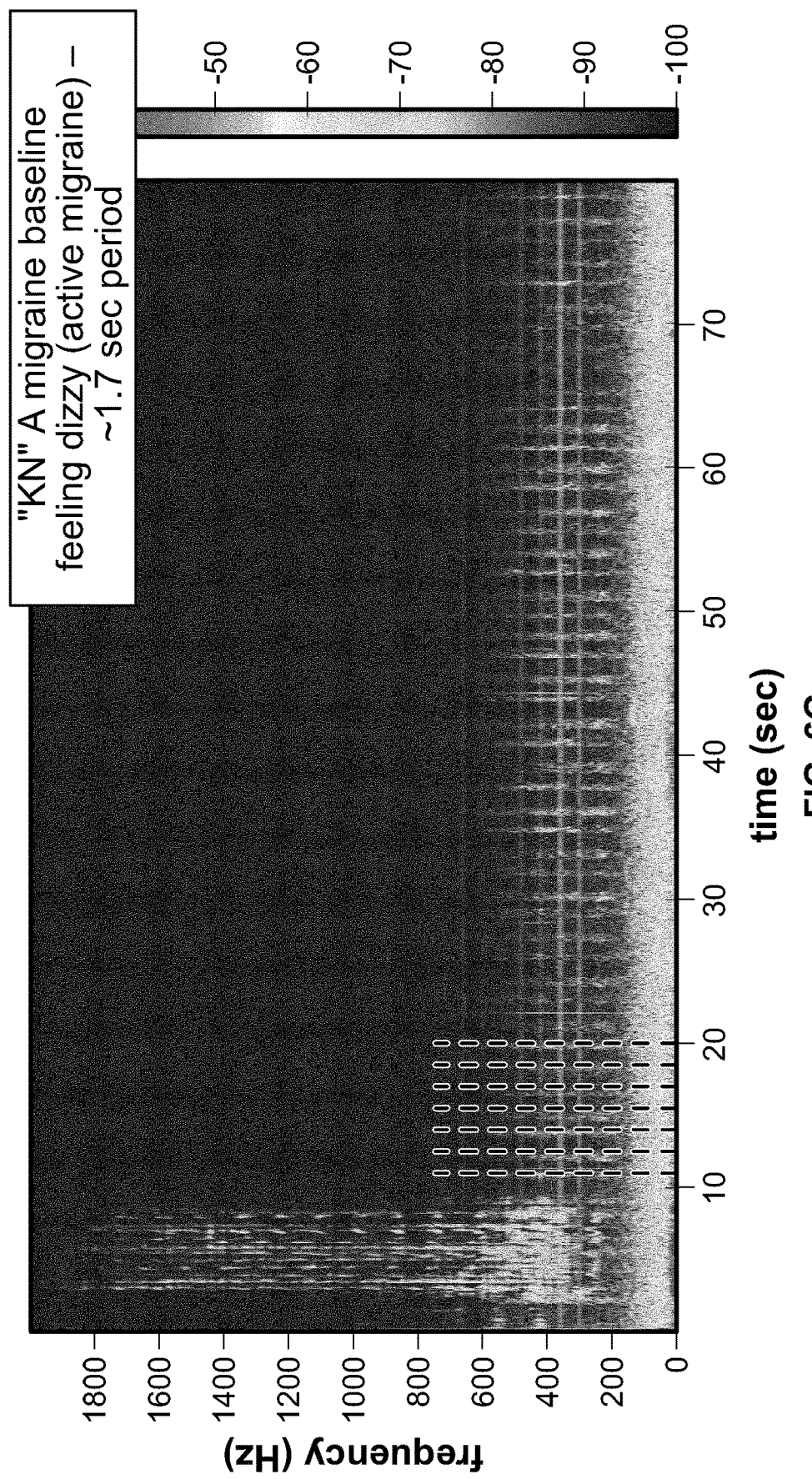
FIG. 6G illustrates periodicity data of a fifth active migraine patient at periods ranging around 1.7 seconds, and frequency ranging between 0 Hz-1000 Hz, in accordance with an embodiment of the present specification.
Figure 6H:
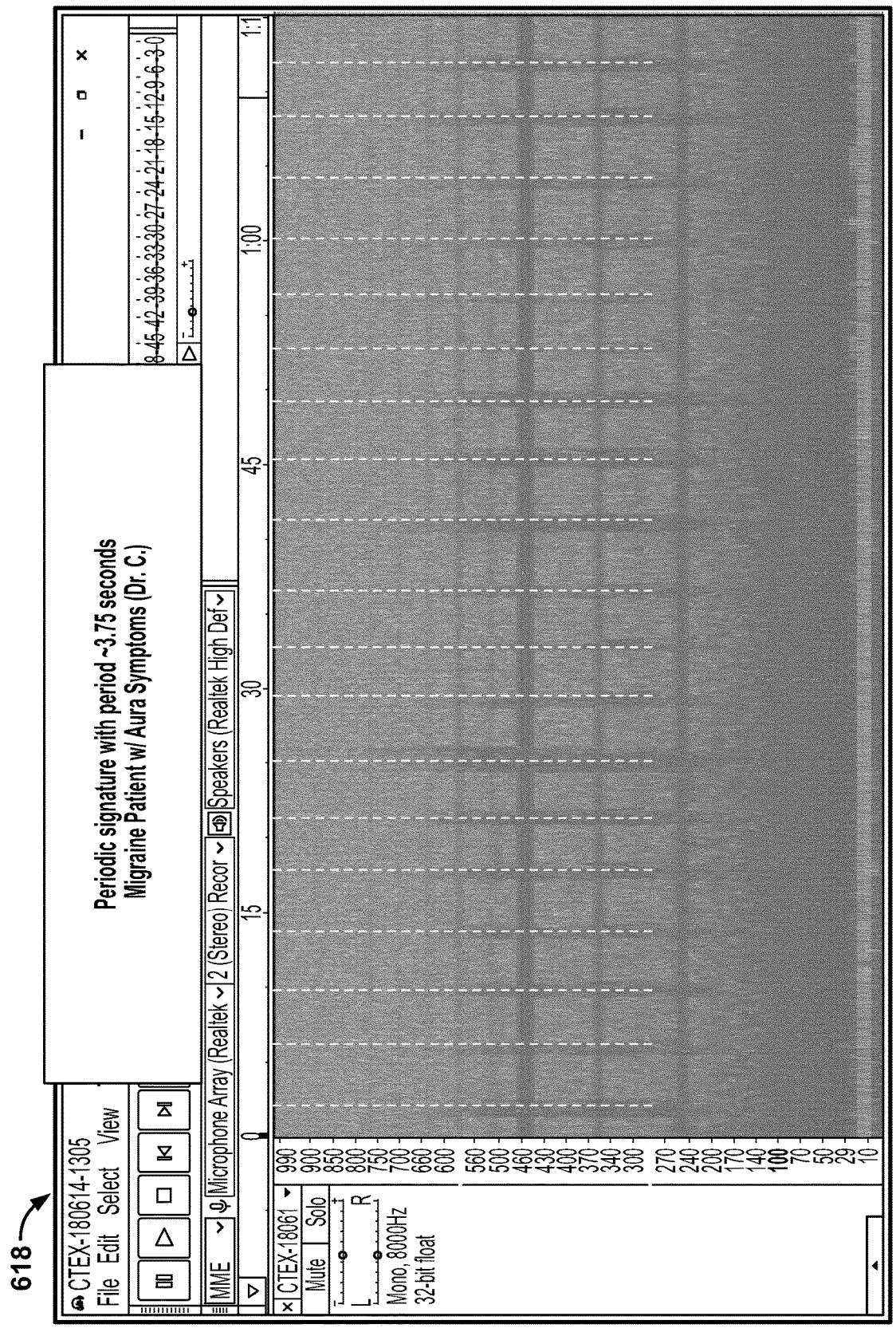
FIG. 6H illustrates periodicity data of a sixth active migraine patient at periods ranging around 3.75 seconds, and frequency ranging between 0 Hz-1000 Hz, in accordance with an embodiment of the present specification.

FIG. 6F illustrates periodicity data 614 of a fourth active migraine patient at periods ranging around 4 seconds, and frequency ranging between 0 Hz-1000 Hz, in accordance with an embodiment of the present specification. FIG. 6G illustrates periodicity data 616 of a fifth active migraine patient at periods ranging around 1.7 seconds, and frequency ranging between 0 Hz-1000 Hz, in accordance with an embodiment of the present specification. FIG. 6H illustrates periodicity data 618 of a sixth active migraine patient at periods ranging around 3.75 seconds, and frequency ranging between 0 Hz-1000 Hz, in accordance with an embodiment of the present specification.

Referring back to FIG. 5A, at step 522 the extracted features are compared against pre-recorded patient data by using the signal analyzer applying deep learning and AI based algorithms (via API calls), to determine if the patient is suffering from at least one of the pathologies at step 524. At step 526, if the patient is suffering from a particular condition, such as a migraine, diagnostic data is presented to the patient. At step 528, the patient is informed, if it is determined that the patient is not suffering from any condition. The diagnosis may be presented in a plurality of formats and on a plurality of devices such as, but not limited to, a mobile phone, a computer, and IOT devices. At step 530, therapeutic and medicinal procedures are performed on the patient for providing relief from the migraine symptoms. In an embodiment, the patient is treated using therapeutic waves via the headset for treating the migraine. At step 532 it is determined if the migraine symptoms have been subdued. If the migraine symptoms have been subdued detection and recording of vibrations generated from cardiac cycles of the patient is performed again by using the headset as in step 508. In an embodiment, a defined therapy in terms of time and energy is provided after a patient is screened for migraine using the headset and a feedback loop. The patient is screened again to determine efficacy or impact on migraine and, if needed, another therapy session is initiated. In an embodiment, the delivered energy may be ultrasound. In embodiments, the screening device of the present specification may be employed with any migraine therapy device.

In various embodiments, each patient data collected via headphones generates unique patterns and features. These unique features are used to create an exclusive signature for each pathology. In an embodiment of the present specification, a unique signature of the data collected with respect to persons suffering from migraine as well as key attributes to characterize the active migraine signature have been identified and are used for diagnosing a patient suffering from migraines. Patients that present with a headache and are diagnosed and treated by using the methods described in the present specification may be classified into the following categories:

Non-Migraine: patient does not experience migraine and does not have any identified underlying condition(s);

Migraine Asymptomatic: patient is not currently afflicted with a migraine or patient who have complained of migraine previously but does not have any identified underlying condition(s);

Migraine Active: patient from Migraine Asymptomatic classification afflicted with an active migraine at the time of the recording;

Migraine Active after Treatment (Rx): patient from Migraine Active who has taken medicine known to alleviate the migraine and waited 30 to 60 minutes prior to the acoustic recording.

Figure 5B:
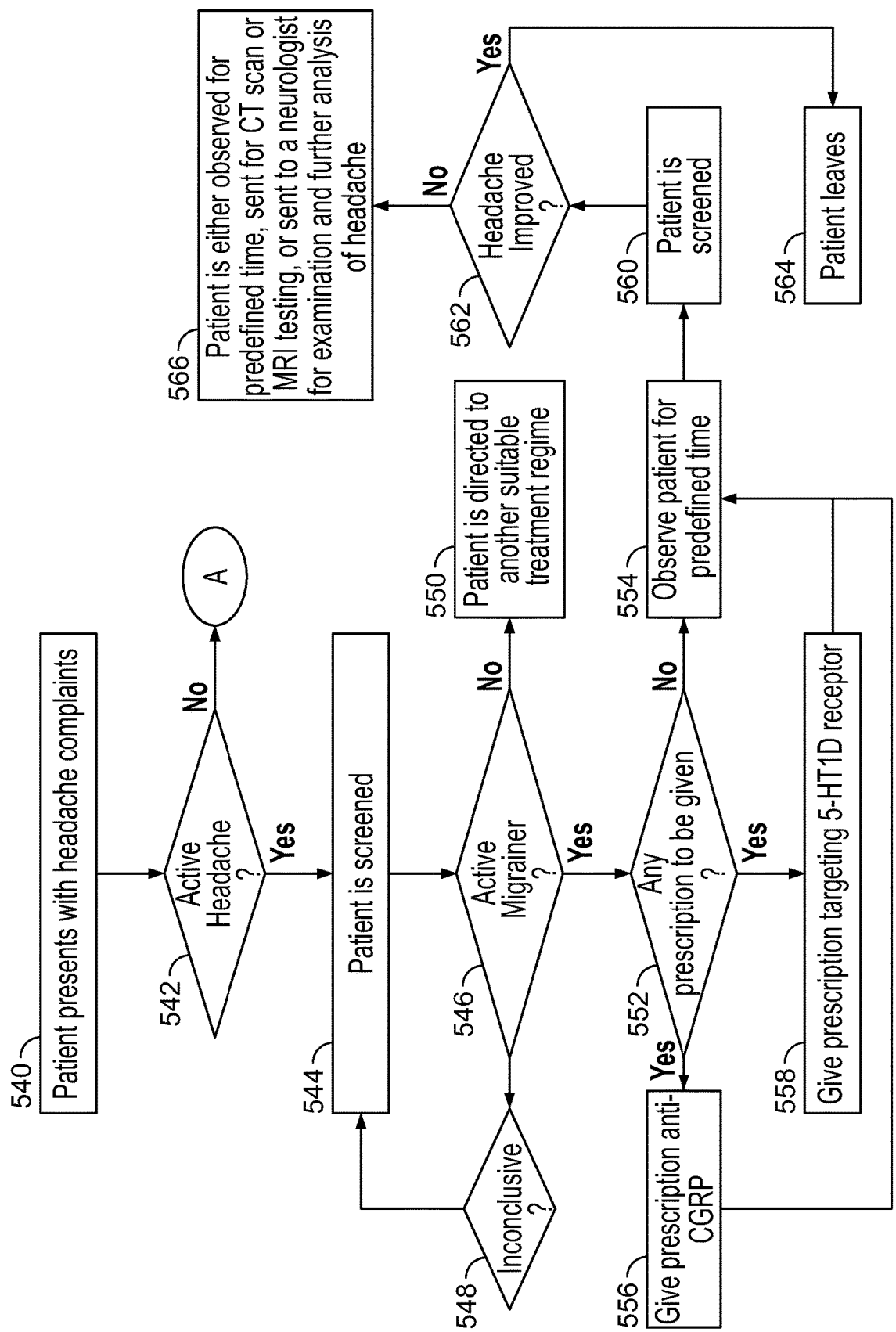
FIG. 5B is a flowchart illustrating the steps of diagnosing and treating a migraine in a patient, in accordance with an embodiment of the present specification.

FIG. 5B is a flowchart illustrating the steps of diagnosing and treating a migraine in a patient, in accordance with an embodiment of the present specification. At step 540, a patient presents with a headache. At step 542, it is determined if the patient is suffering from an active headache. At step 544, if the patient is suffering from an active headache, the patient is screened by using the methods of the present specification. At step 546, the results of screening of the active headache are analyzed and it is determined if the patient is an active migrainer. If the results of the analysis are inconclusive at step 548, step 544 is repeated. In an embodiment, the analyzes involves obtaining an acoustic spectrogram of the patient as explained with respect to FIG. 5A. If the patient is found to not be an active migrainer, at step 550, is the patient is diverted to another suitable treatment regime. In an embodiment, in order to determine if the patient is an active migrainer, the patient's spectrogram is compared with pre-recorded spectrograms of persons suffering from migraine.

At step 552, if the patient's spectrogram is indicating migraine, it is determined if it is required to give the patient prescription drugs. At step 554 if prescription drugs are not required, the patient is kept under observation for a predefined time. Next, treatment by way of anti-migraine prescription medicine, anti-CGRP (calcitonin gene-related peptide) migraine medication at step 556, or anti-SHT1D (human serotonin 1D receptor variant) migraine medication at step 558, is provided to the patient and the patient is observed for a predefined period of time. These medications are of low risk to the patient. At step 560, after providing treatment and keeping the patient under observation, the patient is screened again by using the methods of the present specification. At step 562 if there is improvement in the patient's headache/condition, the treatment is considered a success and the patient obtains relief at step 564. At step 566, if the patient's condition has not improved, the patient is either observed for predefined time; or sent for CT scan or MRI testing; or sent to Neurologist for examination and further analysis of headache.

At step 568 it is determined if the patient is suffering from a chronic headache. At step 570, if the patient is suffering from a chronic headache, the patient is screened by using the methods of the present specification. At step 572, the results of screening of the chronic headache are analyzed and it is determined if the patient is an active migrainer. If the results of the analysis are inconclusive at step 574, step 570 is repeated. In an embodiment, the analyzes involve obtaining an acoustic spectrogram of the patient as explained with respect to FIG. 5A. If the patient is found to not be an active migrainer, at step 576, is the patient is diverted to another suitable treatment regime. In an embodiment, in order to determine if the patient is an active migrainer, the patient's spectrogram is compared with pre-recorded spectrograms of persons suffering from migraine. At step 578, if the patient's spectrogram is indicating migraine, it is determined if it is required to give the patient prescription drugs. At step 580 if prescription drugs are not required, the patient is kept under observation for a predefined time. Next, treatment by way of anti-migraine prescription medicine, anti-CGRP (calcitonin gene-related peptide) migraine medication at step 582, or anti-SHT1D (human serotonin 1D receptor variant) migraine medication at step 584, is provided to the patient and the patient is observed for a predefined period of time. These medications are of low risk to the patient. At step 586, after providing treatment and keeping the patient under observation, the patient is screened again by using the methods of the present specification. At step 588 if there is improvement in the patient's headache/condition, the treatment is considered a success and the patient obtains relief at step 590. At step 592, if the patient's condition has not improved, the patient is either observed for predefined time; or sent for CT scan or MRI testing; or sent to Neurologist for examination and further analysis of headache. At step 594, the patients screening results of step 586 and 562 are analyzed to determine the pathologies not improved by Rx medication and effect of Rx medication on such pathologies.

Figure 7A:
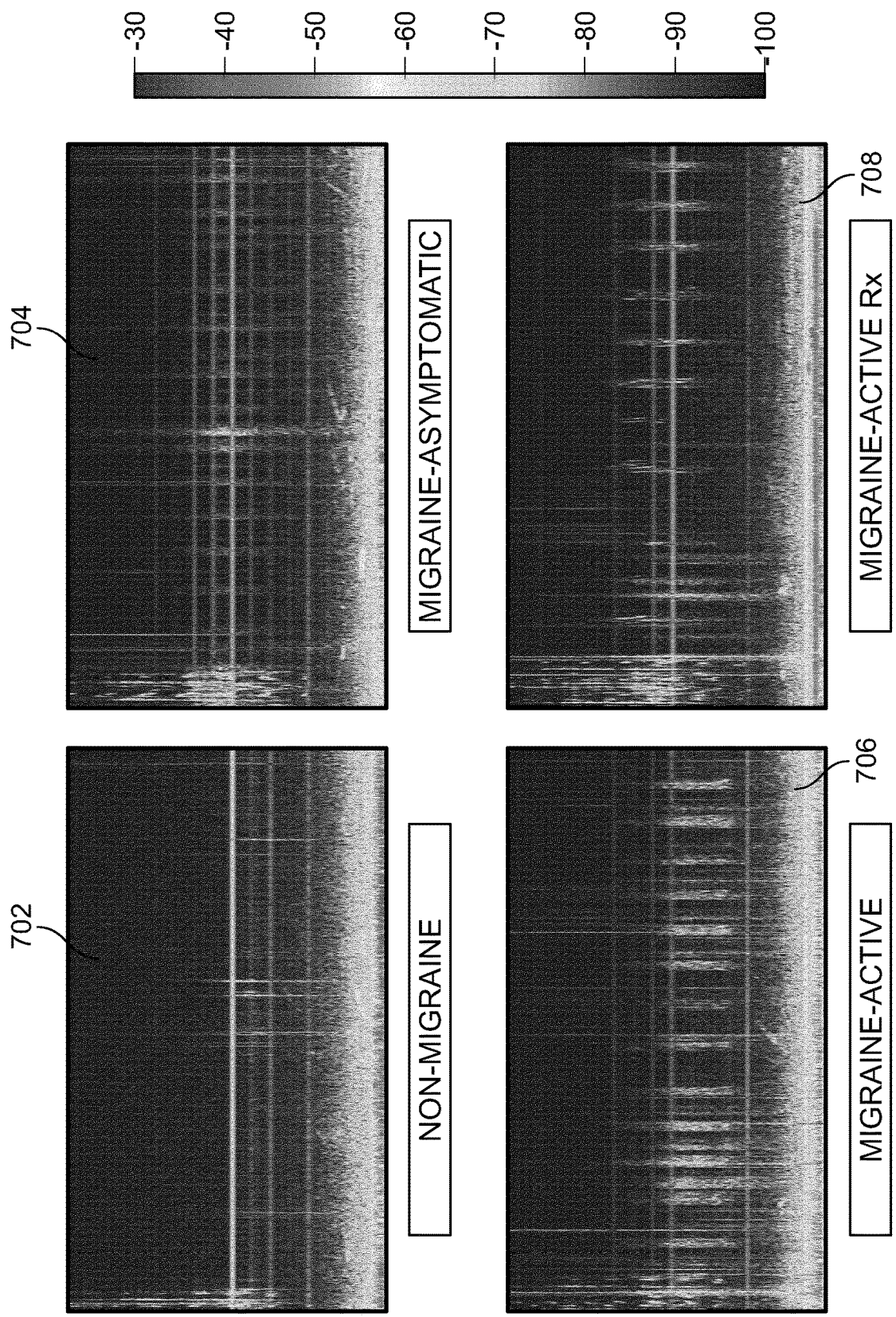
FIG. 7A illustrates two dimensional (2D) spectrographs representing data obtained from a plurality of patients, in accordance with an embodiment of the presentation.

FIG. 7A illustrates two dimensional (2D) spectrographs representing data obtained from a plurality of patients, in accordance with an embodiment of the presentation. In the figure, 2D spectrograph 702 represents data obtained from a first patient who does not have a history of migraine; 2D spectrograph 704 represents data obtained from a second patient who has a history of migraine, however was not experiencing symptoms of migraine (asymptomatic) at the time when the data was obtained; 2D spectrograph 706 represents data obtained from the same second patient who has a history of migraine, and was also experiencing symptoms of migraine at the time when the data was obtained; 2D spectrograph 708 represents data obtained from the same second patient after taking medication for the migraines, the data having been obtained at a time when the migraine symptoms had subsided.

Figure 7B:
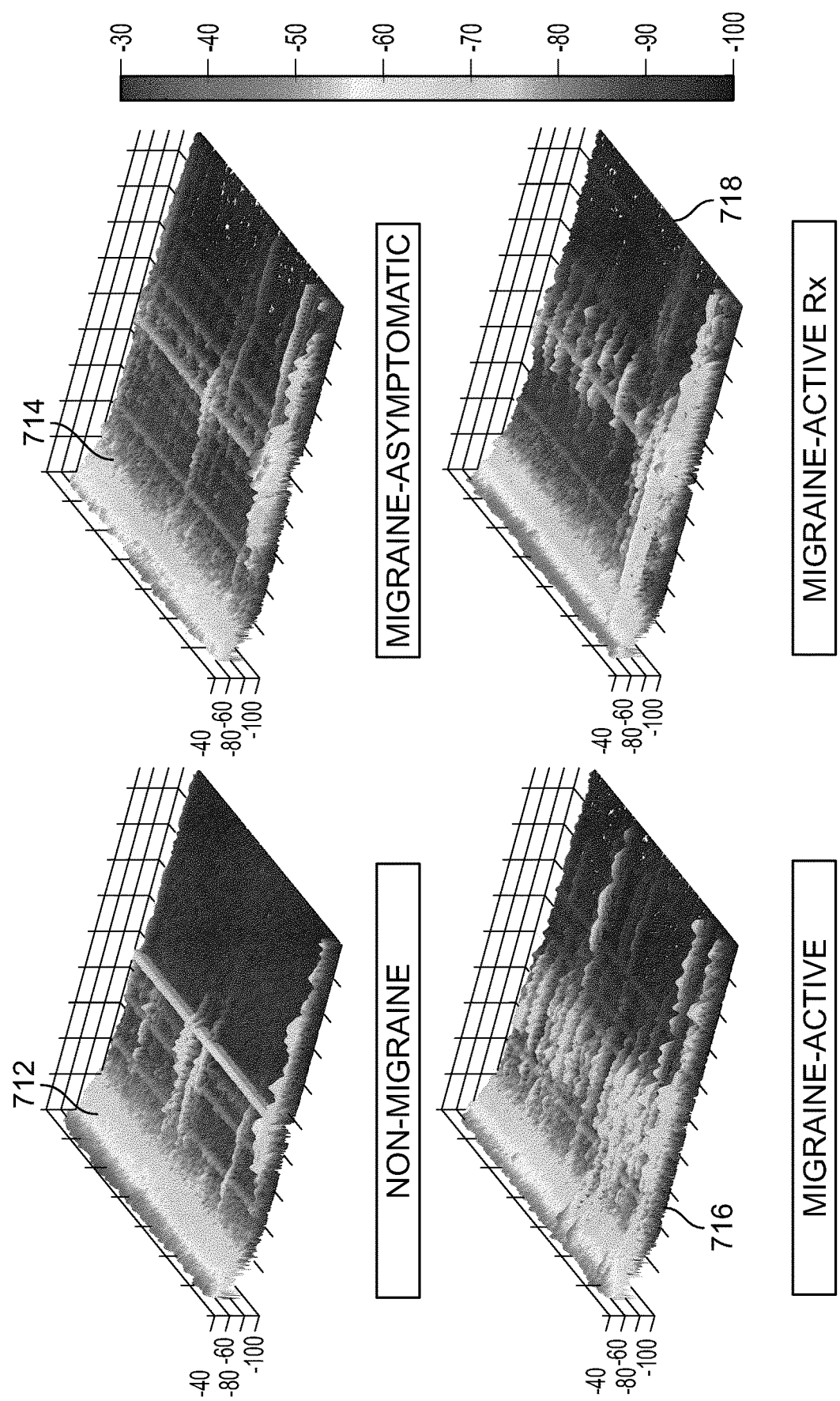
FIG. 7B illustrates three dimensional (3D) spectrographs representing data obtained from a plurality of patients, in accordance with an embodiment of the specification.

FIG. 7B illustrates three dimensional (3D) spectrographs representing data obtained from a plurality of patients, in accordance with an embodiment of the specification. In the figure, 3D spectrograph 712 represents data obtained from a first patient who does not have a history of migraine; 3D spectrograph 714 represents data obtained from a second patient who has a history of migraine, however was not experiencing symptoms of migraine (asymptomatic) at the time when the data was obtained; 3D spectrograph 716 represents data obtained from the same second patient who has a history of migraine, and was also experiencing symptoms of migraine at the time when the data was obtained; and 3D spectrograph 718 represents data obtained from the same second patient after taking medication for the migraines, the data having been obtained at a time when the migraine symptoms had subsided. As can be observed from the spectrographs illustrated in FIGS. 7A and 7B, each patient condition provides a unique data signature.

Figure 7C:
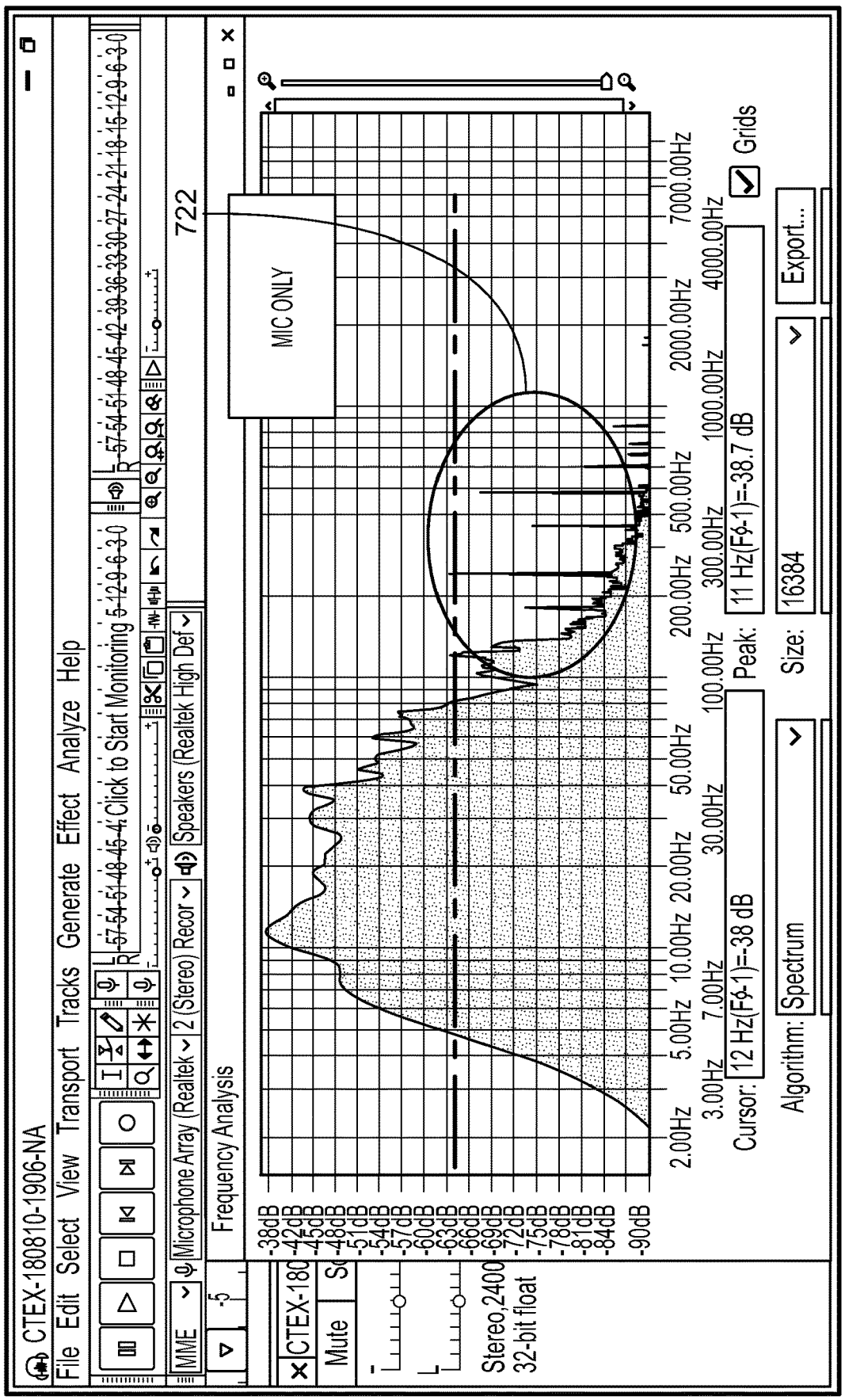
FIG. 7C illustrates graphical representation of audio data collected from different subjects, in accordance with an embodiment of the present specification.
Figure 7C:
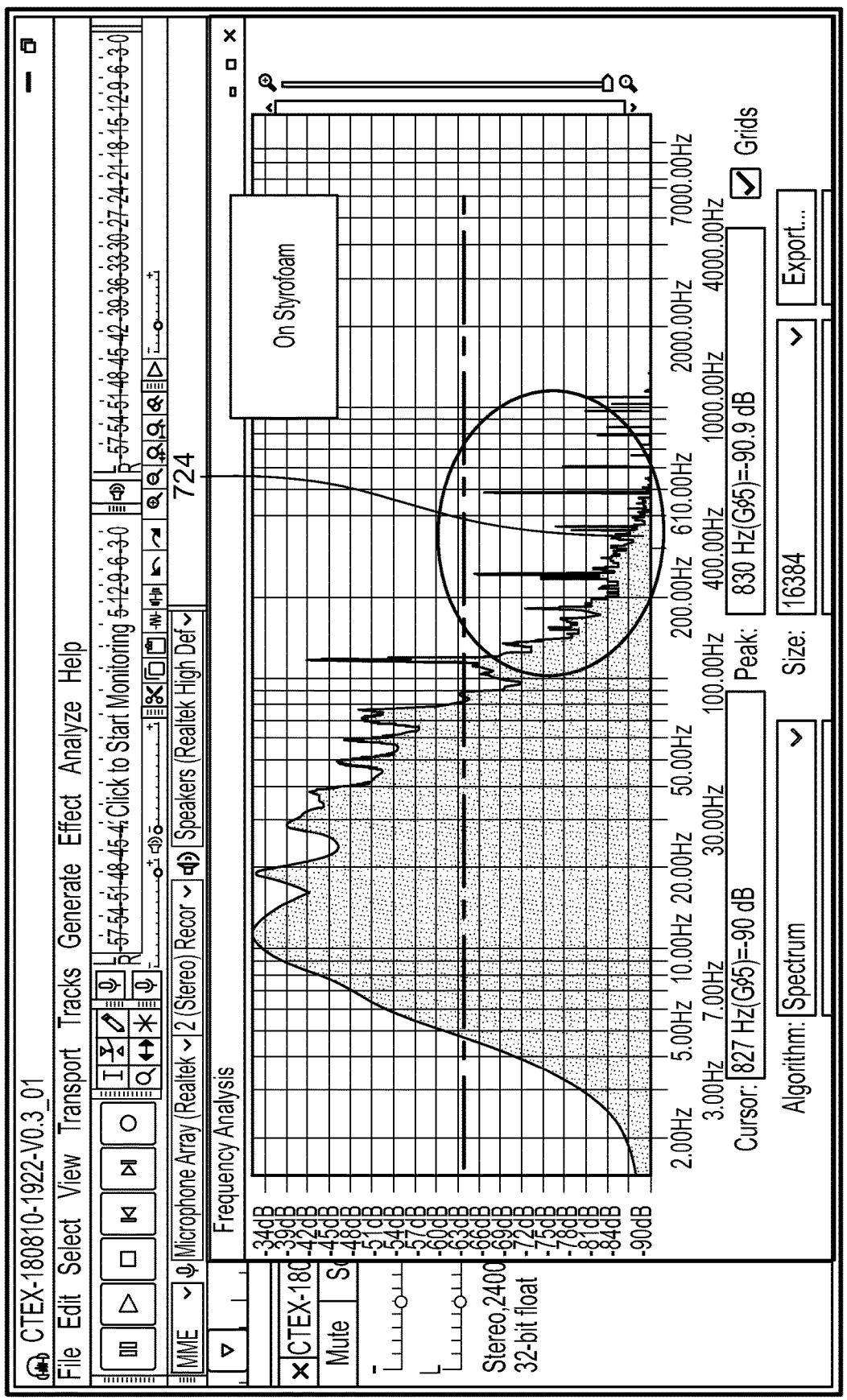
Figure 7C:
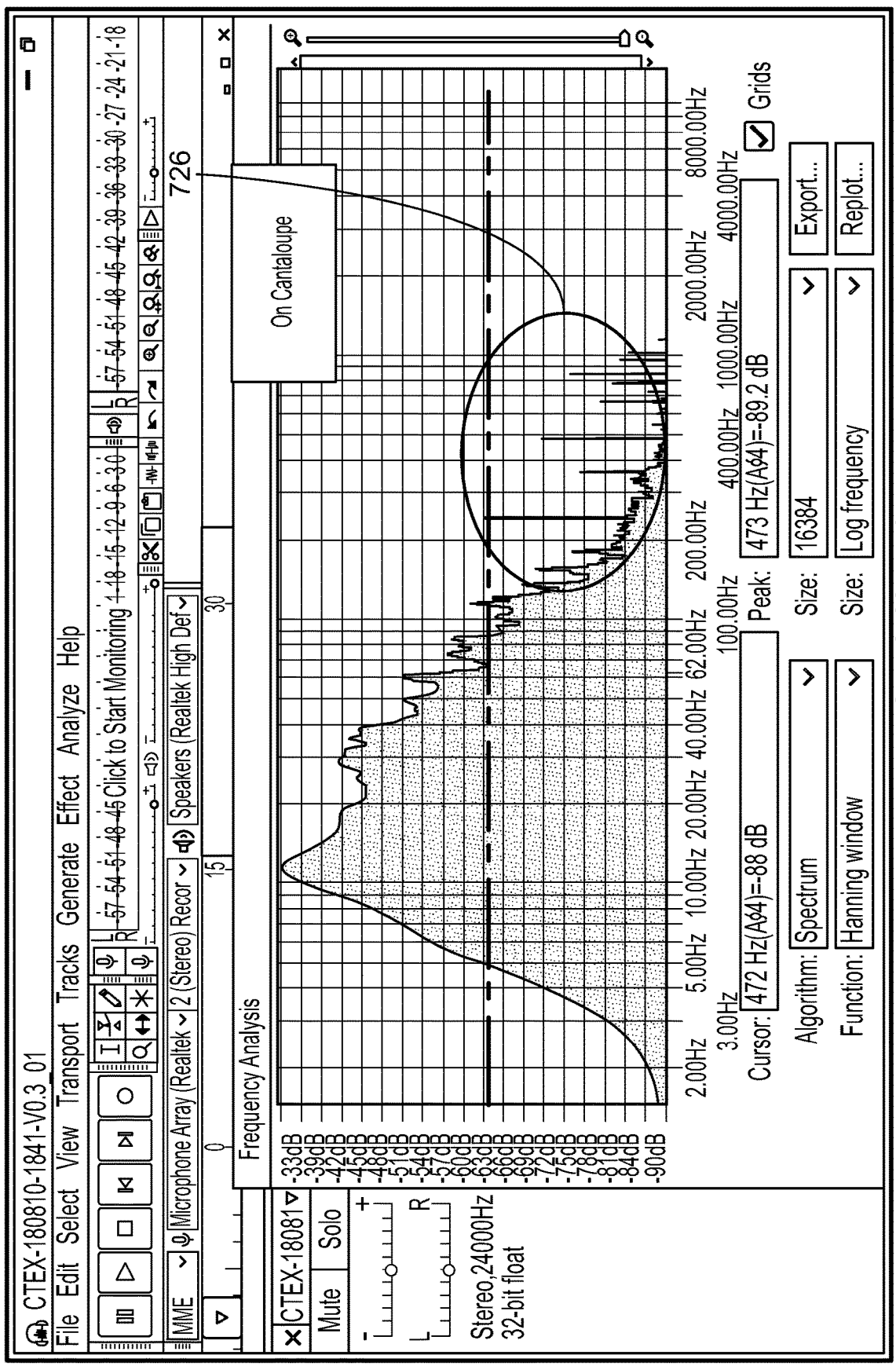
Figure 7C:
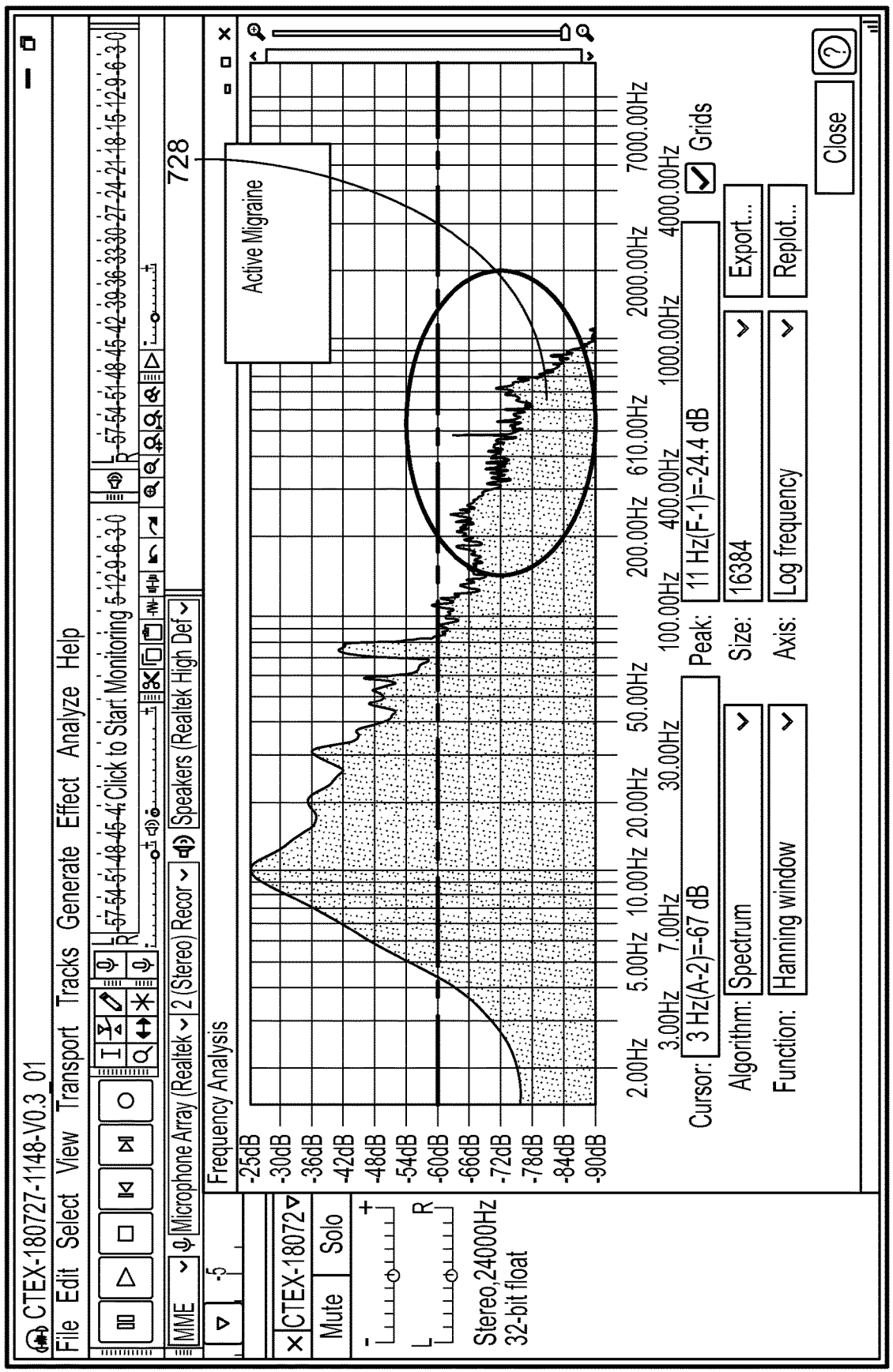

FIG. 7C illustrates graphical representation of audio data collected from different subjects, in accordance with an embodiment of the present specification. Plot 722 illustrates audio data collected when no subject is connected to a microphone of the headset of the present specification. Plot 724 illustrates audio data collected when the microphone of the headset of the present specification is connected to a piece of Styrofoam. Plot 726 illustrates audio data collected when the microphone of the headset of the present specification is connected to a piece of cantaloupe. Plot 728 illustrates audio data collected when the microphone of the headset of the present specification is connected to a patient suffering from active migraine. FIG. 7C illustrates how the data signature 728 of the patient suffering from active migraine is different from all other plots 722,724 and 726.

Figure 7D:
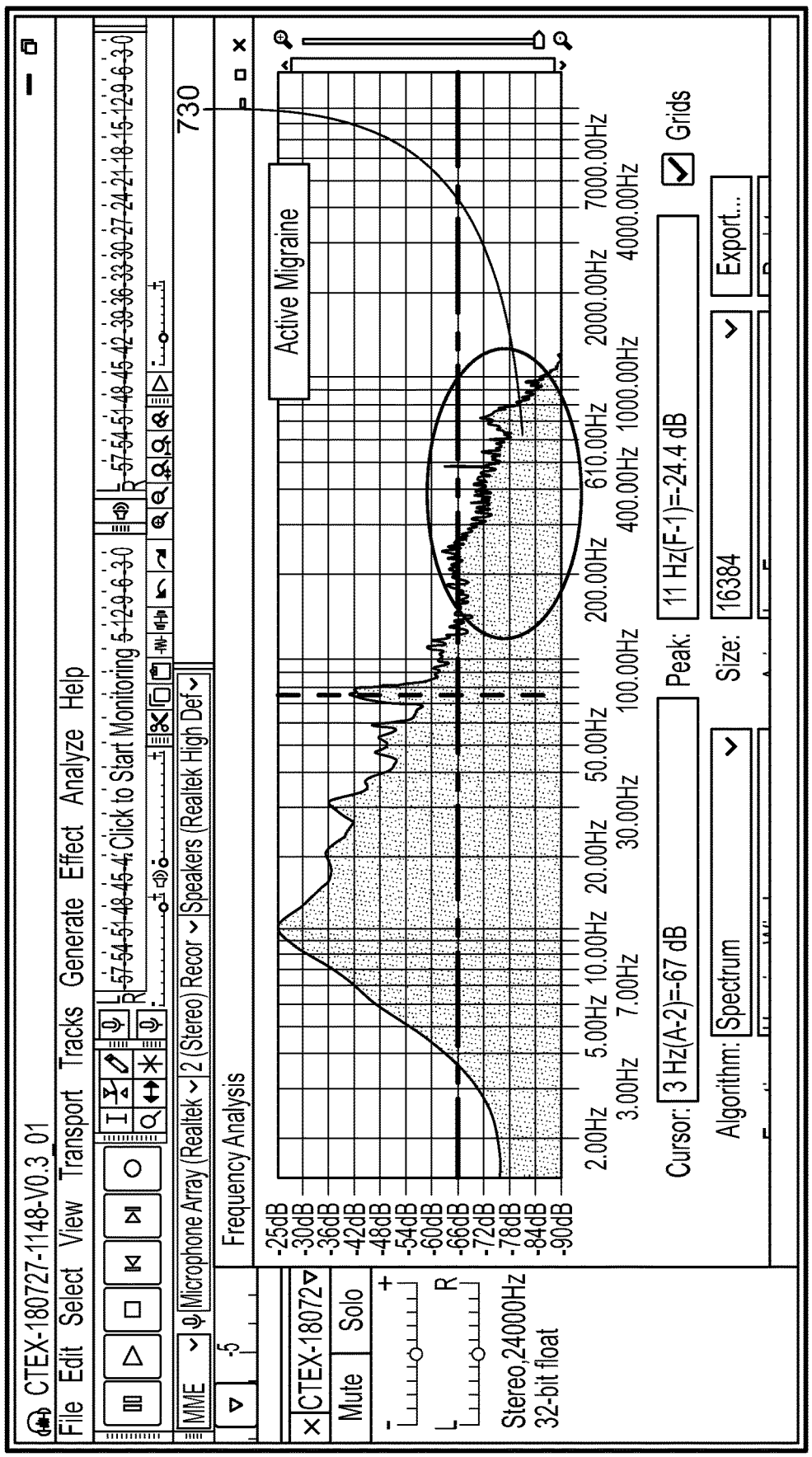
FIG. 7D is a graphical representation of a unique data signature of a person suffering from migraine as compared to that of a person not suffering from migraine over a slice of time, in accordance with an embodiment of the present specification.
Figure 7D:
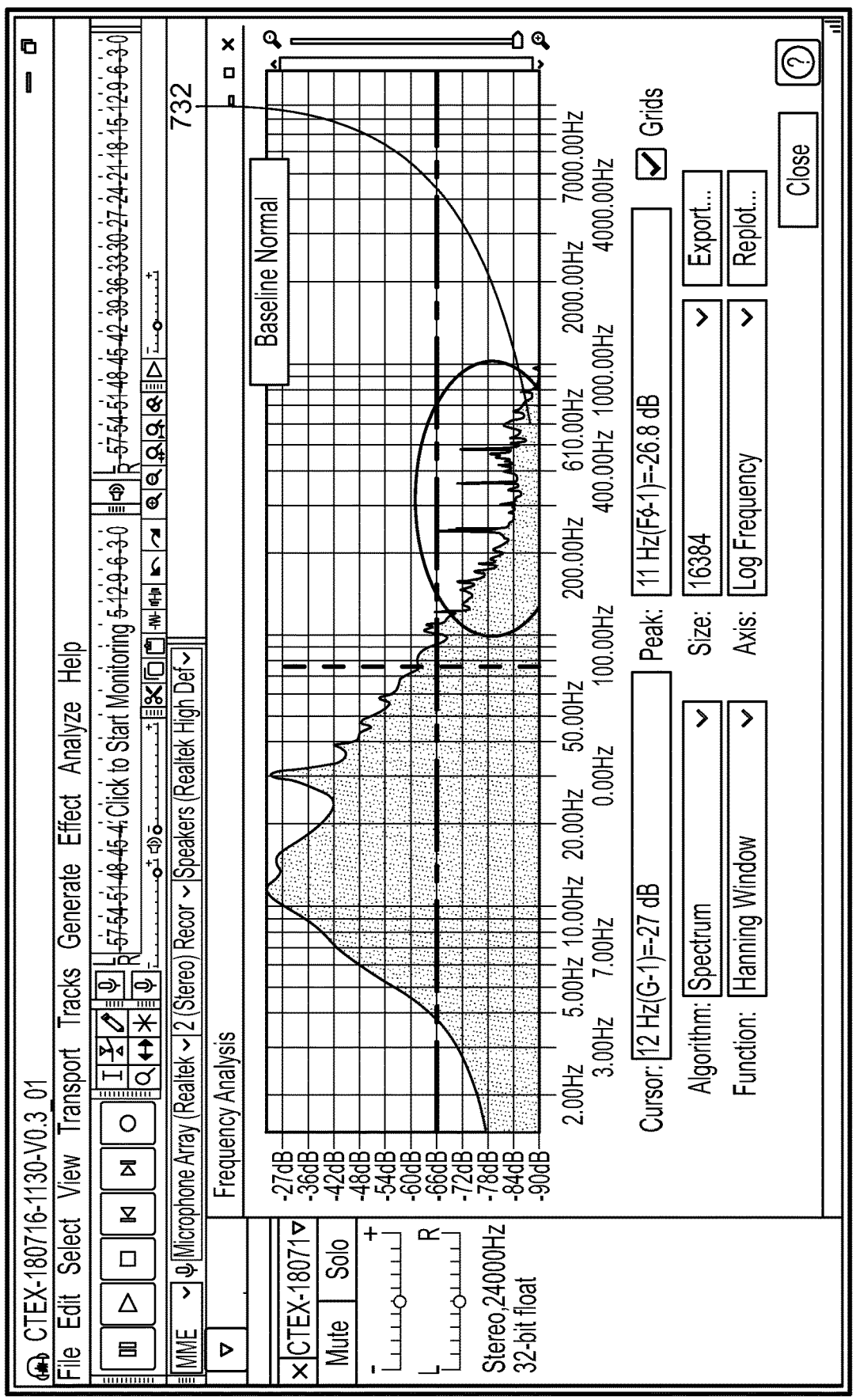
Figure 7E:
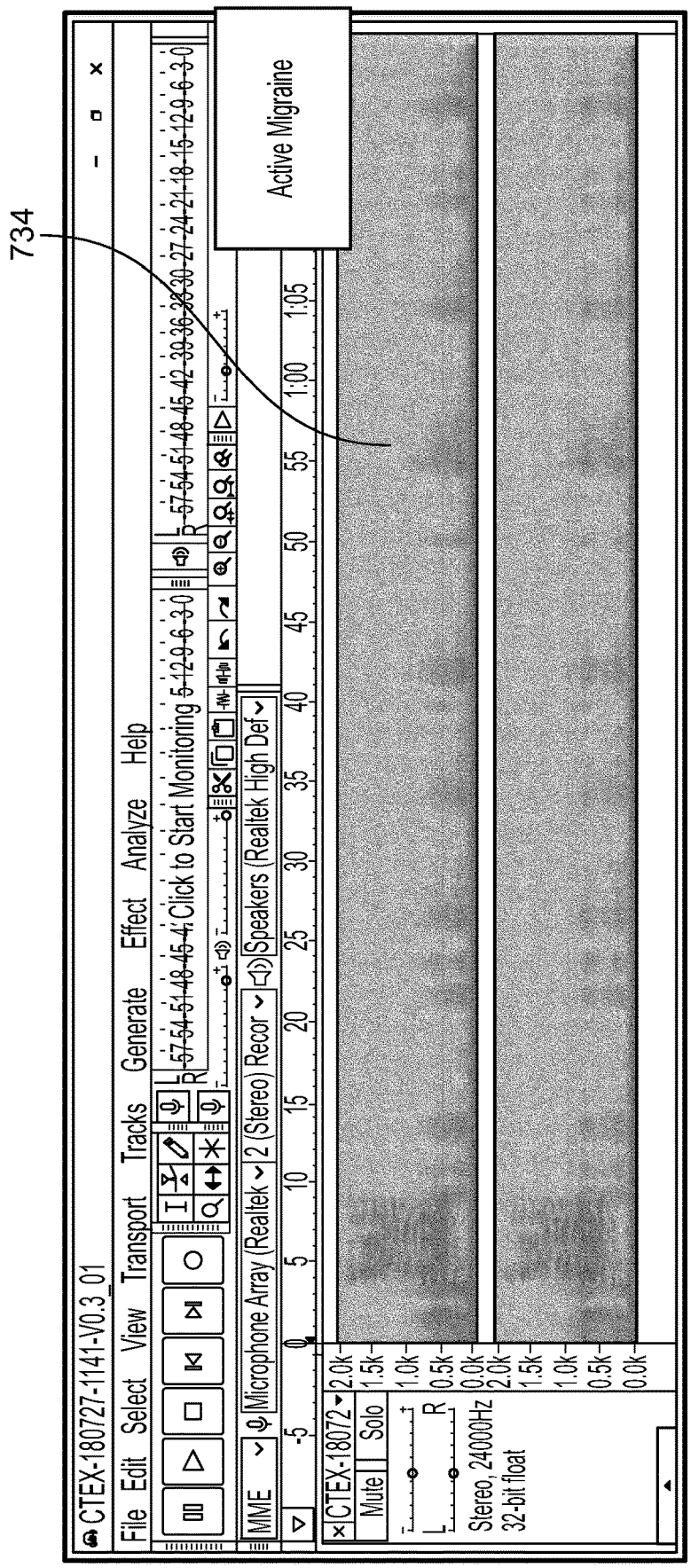
FIG. 7E is a graphical representation of a unique data signature of a person suffering from migraine as compared to that of a person not suffering from migraine captured over a time period ranging from 1.5-2 seconds, in accordance with an embodiment of the present specification.
Figure 7E:
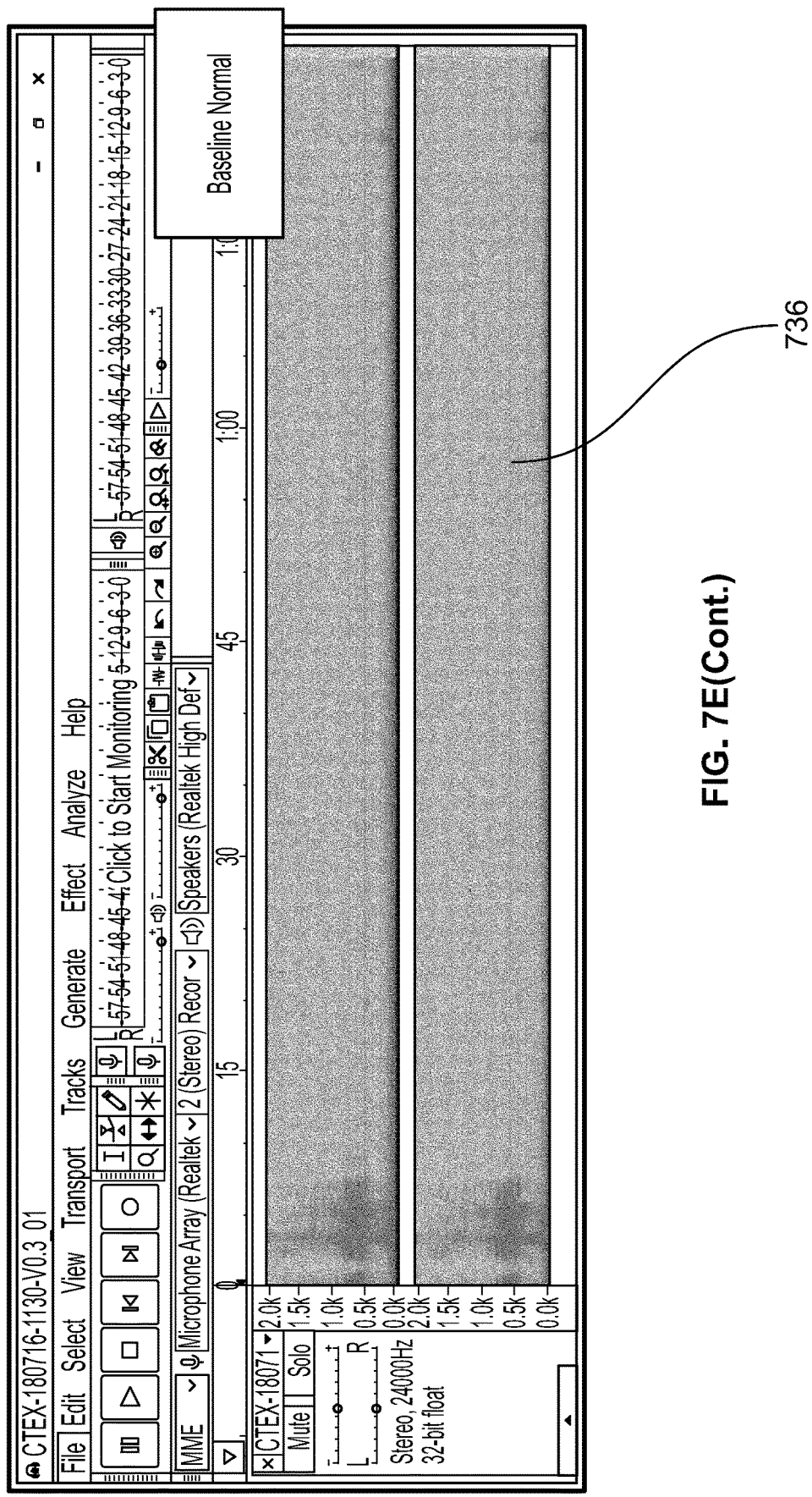

FIG. 7D is a graphical representation of a unique data signature of a person suffering from migraine as compared to that of a person not suffering from migraine as determined over frequency range, in accordance with an embodiment of the present specification. Plot 730 depicts the data obtained from a person suffering from active migraine while plot 732 depicts the data obtained from a person with no migraine symptoms, wherein the data corresponds to a frequency greater than 200 Hz. FIG. 7E is a graphical representation of a unique data signature of a person suffering from migraine as compared to that of a person not suffering from migraine captured over a time period ranging from 1.5-2 seconds, in accordance with an embodiment of the present specification. Plot 734 depicts the data obtained from a person suffering from active migraine while plot 736 depicts the data obtained from a person with no migraine symptoms, wherein the data corresponds to a frequency greater than 200 Hz and is captured over a time period ranging from 1.5-2 seconds.

Figure 7F:
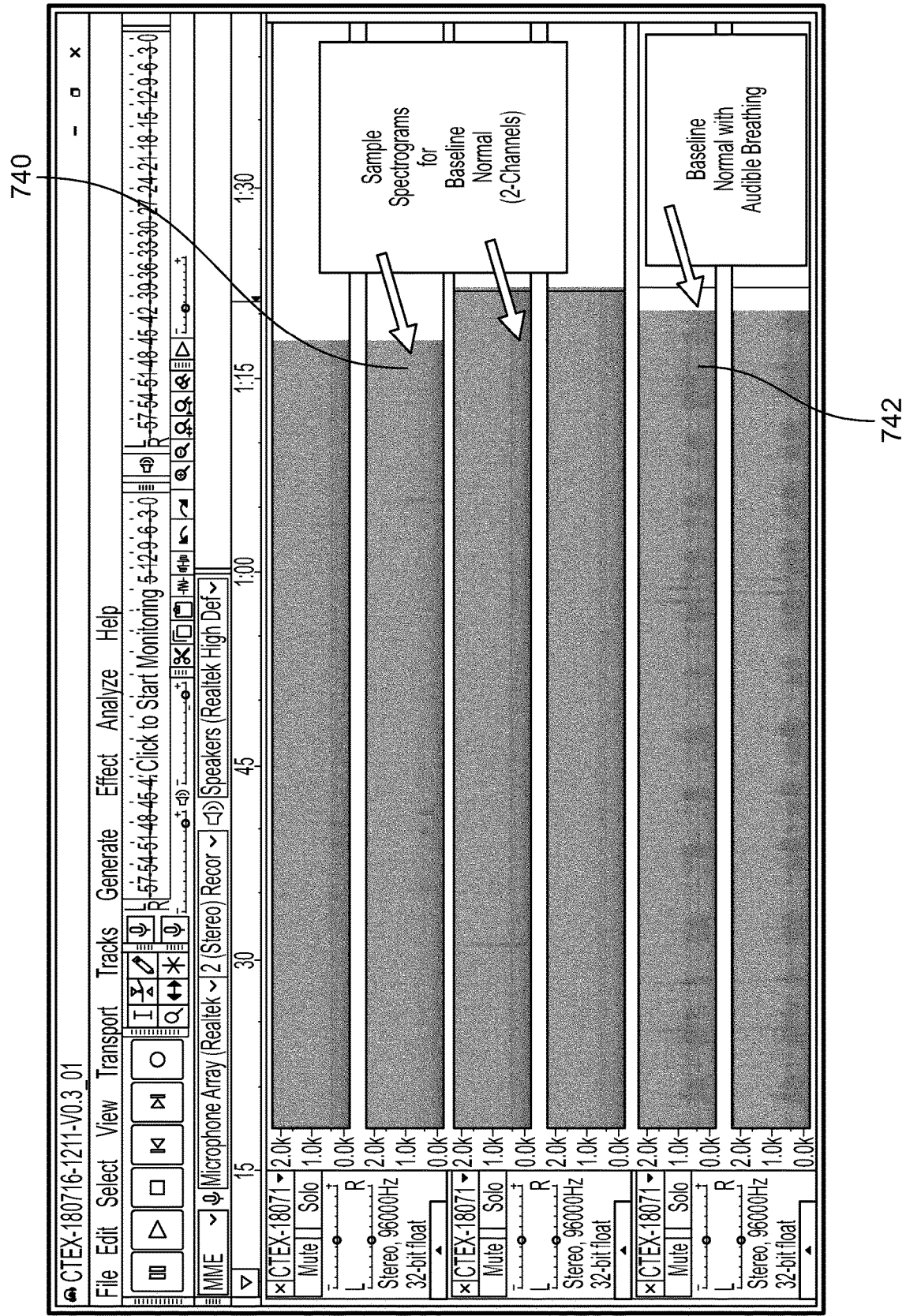
FIG. 7F is a graphical representation of a unique data signature of a person not experiencing migraine as compared to that of the same person breathing audibly, in accordance with an embodiment of the present specification.
Figure 7G:
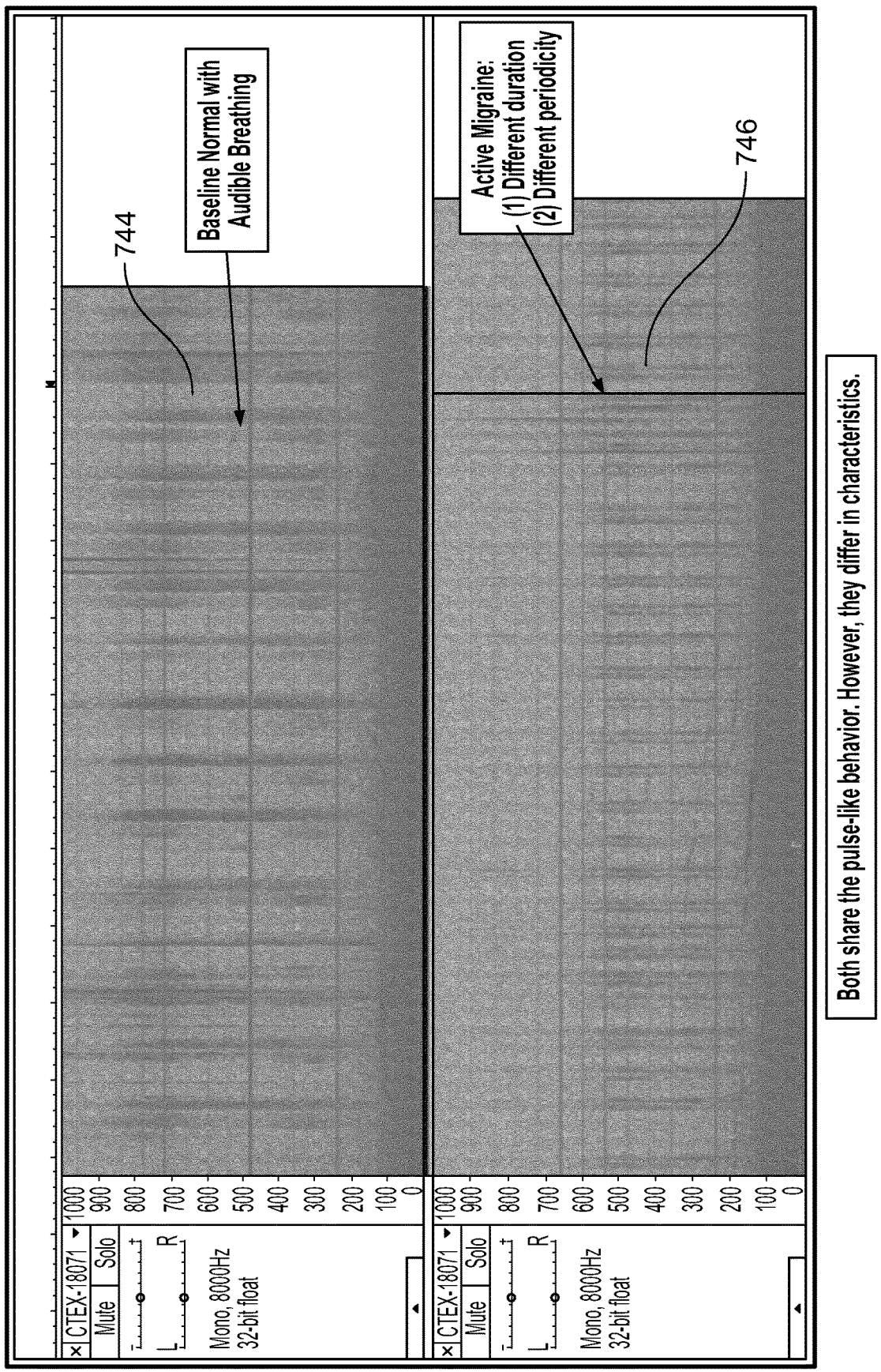
FIG. 7G is a graphical representation of a unique data signature of a person not experiencing migraine breathing audibly and a person experiencing migraine symptoms, in accordance with an embodiment of the present specification.

FIG. 7F is a graphical representation of a unique data signature of a person not experiencing migraine as compared to that of the same person breathing audibly, in accordance with an embodiment of the present specification. Plot 740 depicts the data obtained from a person not experiencing migraine while plot 742 depicts the data obtained from the same person while the person was breathing audibly. FIG. 7G is a graphical representation of a unique data signature of a person not experiencing migraine breathing audibly and a person experiencing migraine symptoms, in accordance with an embodiment of the present specification. Plot 744 depicts the data obtained from a person not experiencing migraine and breathing audibly while plot 746 depicts the data obtained from a person experiencing migraine symptoms. Plots 740, 742, 744 and 746 illustrate that the spectrographs obtained from persons not having migraines with audible breathing demonstrate different characteristics as compared to the spectrographs obtained from persons suffering from active migraine.

Figure 7H:
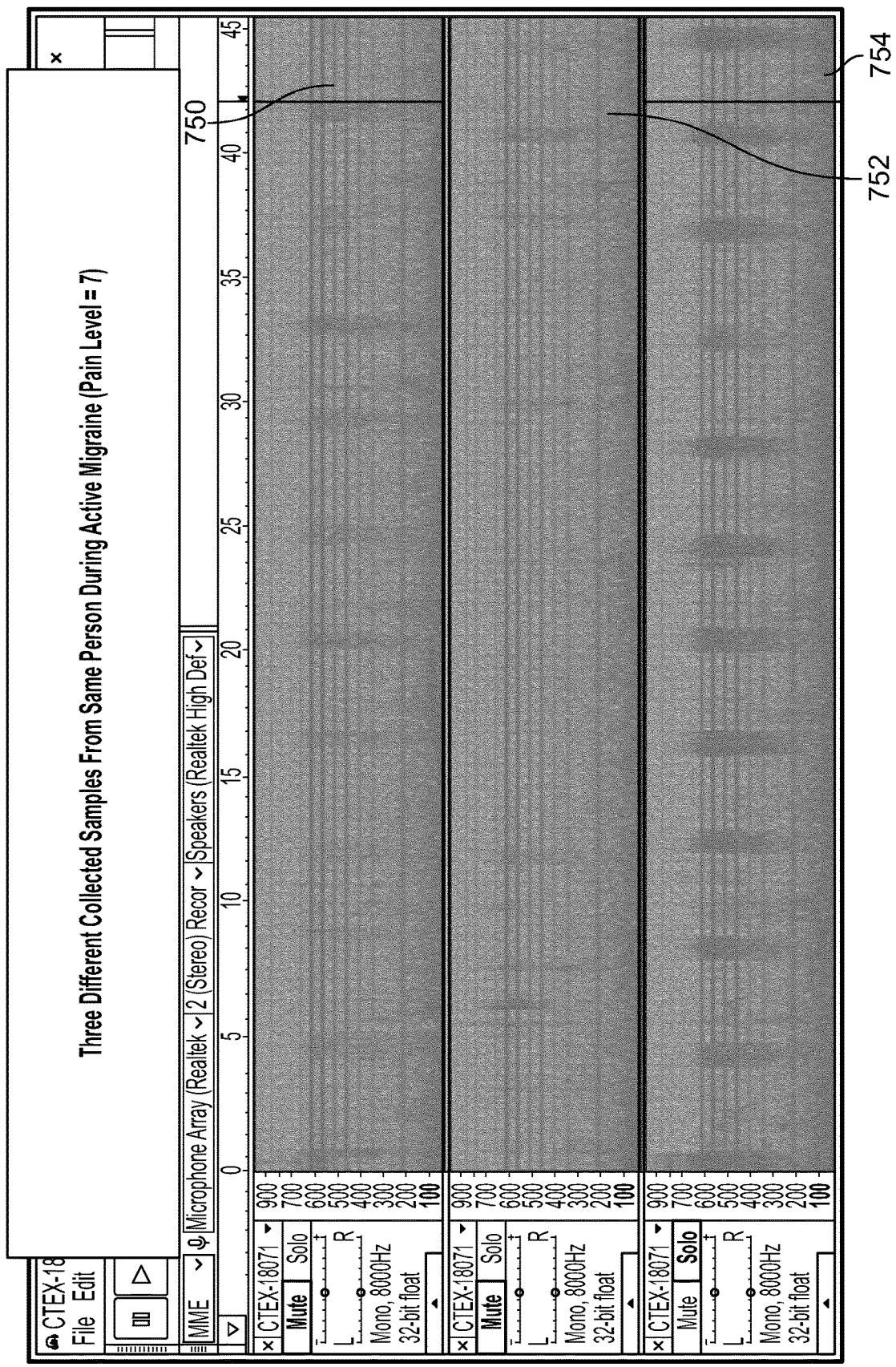
FIG. 7H is a graphical representation of a unique data signature of a person experiencing migraine symptoms obtained over a time period of approximately 1.5 seconds, in accordance with an embodiment of the present specification.
Figure 71:
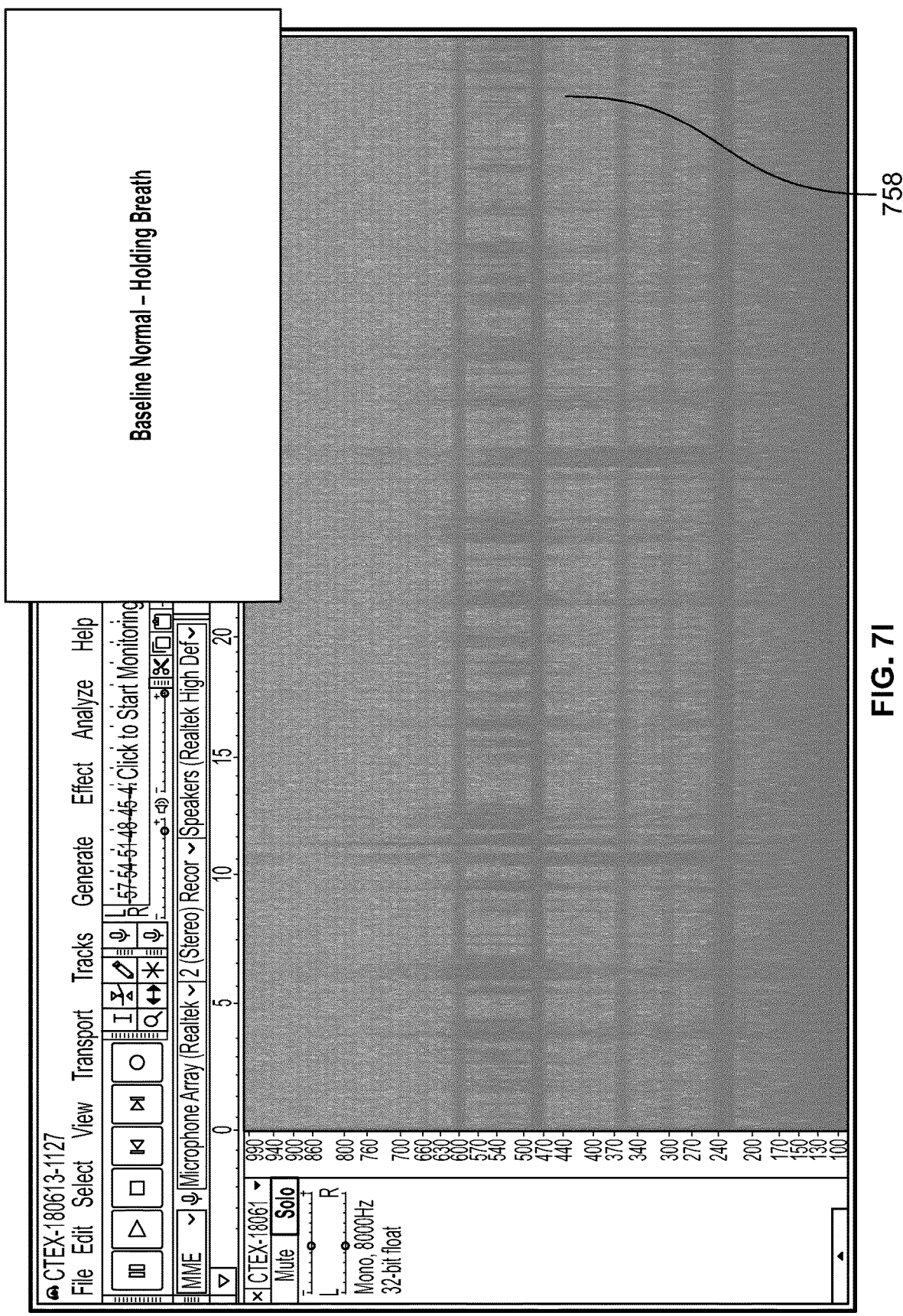
Figure 7I:
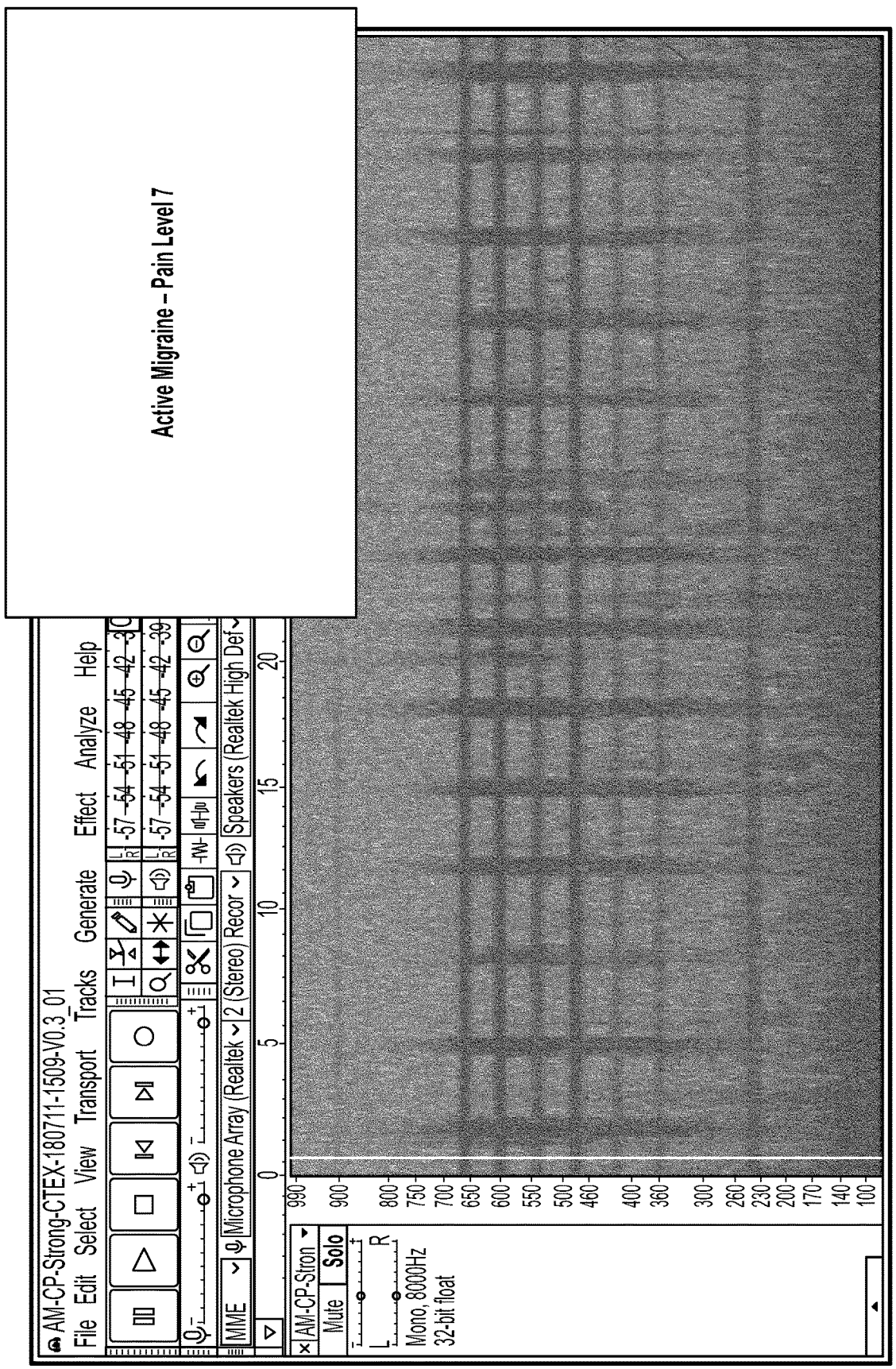
FIG. 7I is a graphical representation of a unique data signature of a person not experiencing migraine and holding his breath; and a person experiencing migraine symptoms, in accordance with an embodiment of the present specification.

FIG. 7H is a graphical representation of a unique data signature of a person experiencing migraine symptoms obtained over a time period of approximately 1.5 seconds, in accordance with an embodiment of the present specification. Plots 750, 752 and 754 are spectrograms corresponding to one person experiencing a pain level of '7', obtained at an 8 kHz sampling rate, Hanning Window size of 1024 (which is in between a narrowband and a wideband) scaled to focus on 100-1000 Hz frequency range. FIG. 7I is a graphical representation of a unique data signature of a person not experiencing migraine and holding his breath; and a person experiencing migraine symptoms, in accordance with an embodiment of the present specification. Plot 756 depicts the data obtained from a person not experiencing migraine and holding his breath while plot 758 depicts the data obtained from a person experiencing migraine at a pain level of '7'.

Figure 7J:
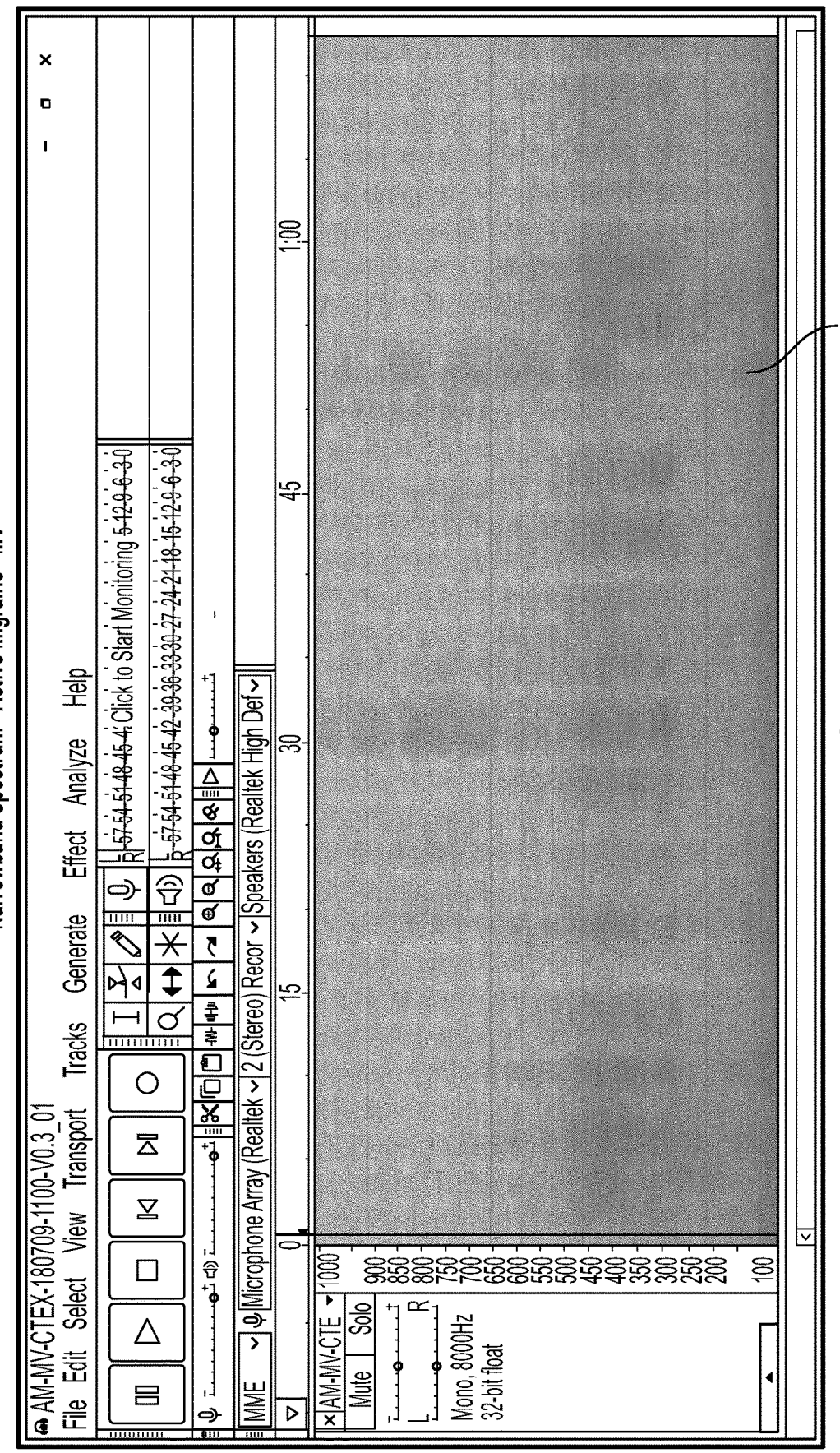
FIG. 7J illustrates a narrowband spectrogram of a person experiencing an active migraine pain, in accordance with an embodiment of the present specification.

FIG. 7J illustrates a narrowband spectrogram of a person experiencing an active migraine pain, in accordance with an embodiment of the present specification. Plot 760 is a narrowband spectrogram created at a high-resolution frequency analysis, wherein the Window size is 32768 and the frequency ranges from 80 Hz to 300 Hz making individual harmonics visible.

Figure 7K:
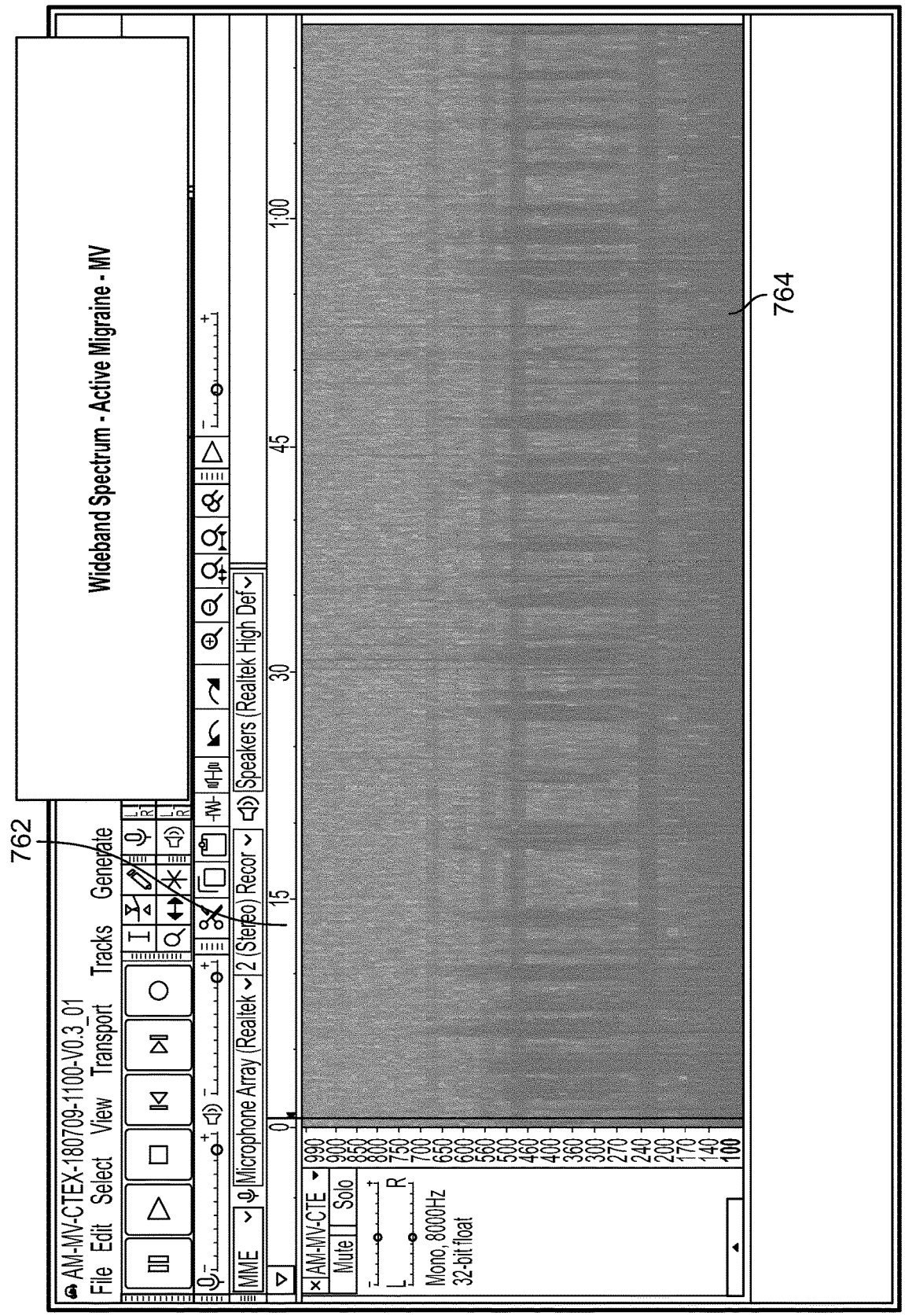
FIG. 7K illustrates a wideband spectrogram of a person experiencing an active migraine pain, in accordance with an embodiment of the present specification.
Figure 7L:
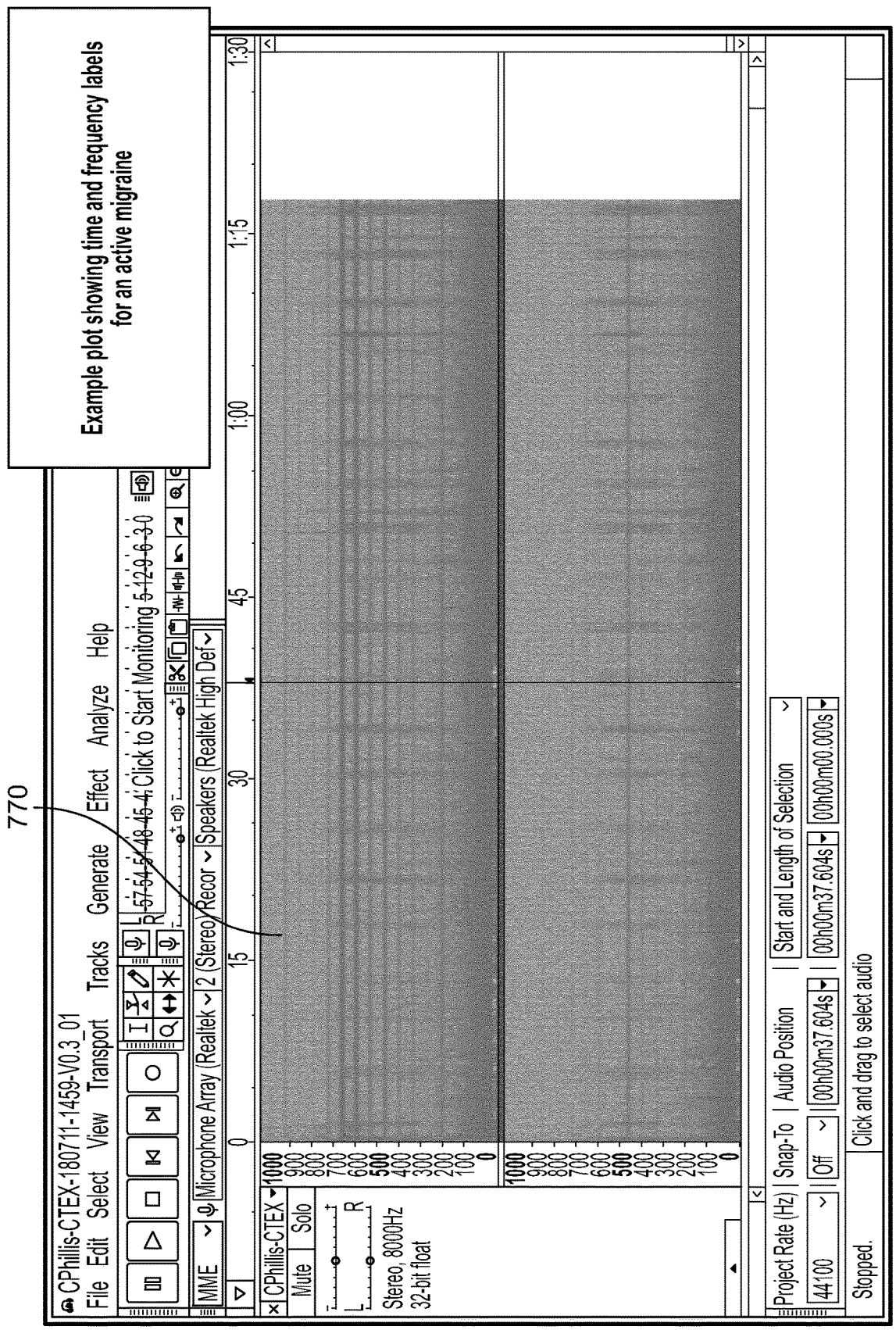
FIG. 7L illustrates a spectrogram 770 of a person experiencing an active migraine pain showing time and frequency levels, in accordance with an embodiment of the present specification.

FIG. 7K illustrates a wideband spectrogram of a person experiencing an active migraine pain, in accordance with an embodiment of the present specification. Plot 762 is a wideband spectrogram created with a coarse frequency analysis over a short segment of the time signal. Plot 762 shows vertical lines 764 corresponding to the rapid increase in amplitude. These vertical lines are not visible in the narrowband spectrogram 760 shown in FIG. 7J. FIG. 7L illustrates a spectrogram 770 of a person experiencing an active migraine pain showing time and frequency levels, in accordance with an embodiment of the present specification.

Figure 8A:
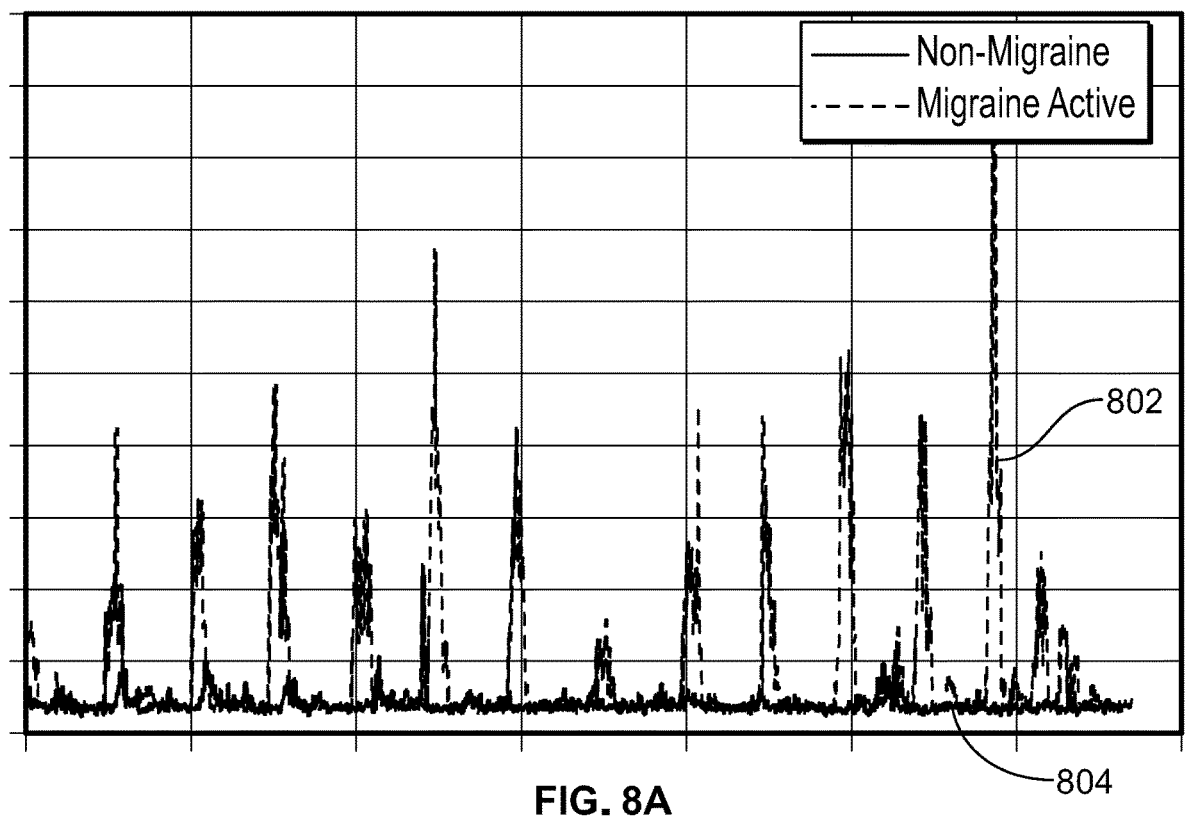
FIG. 8A is a graphical representation of a unique data signature of a person suffering from migraine, in accordance with an embodiment of the present specification.
Figure 8B:
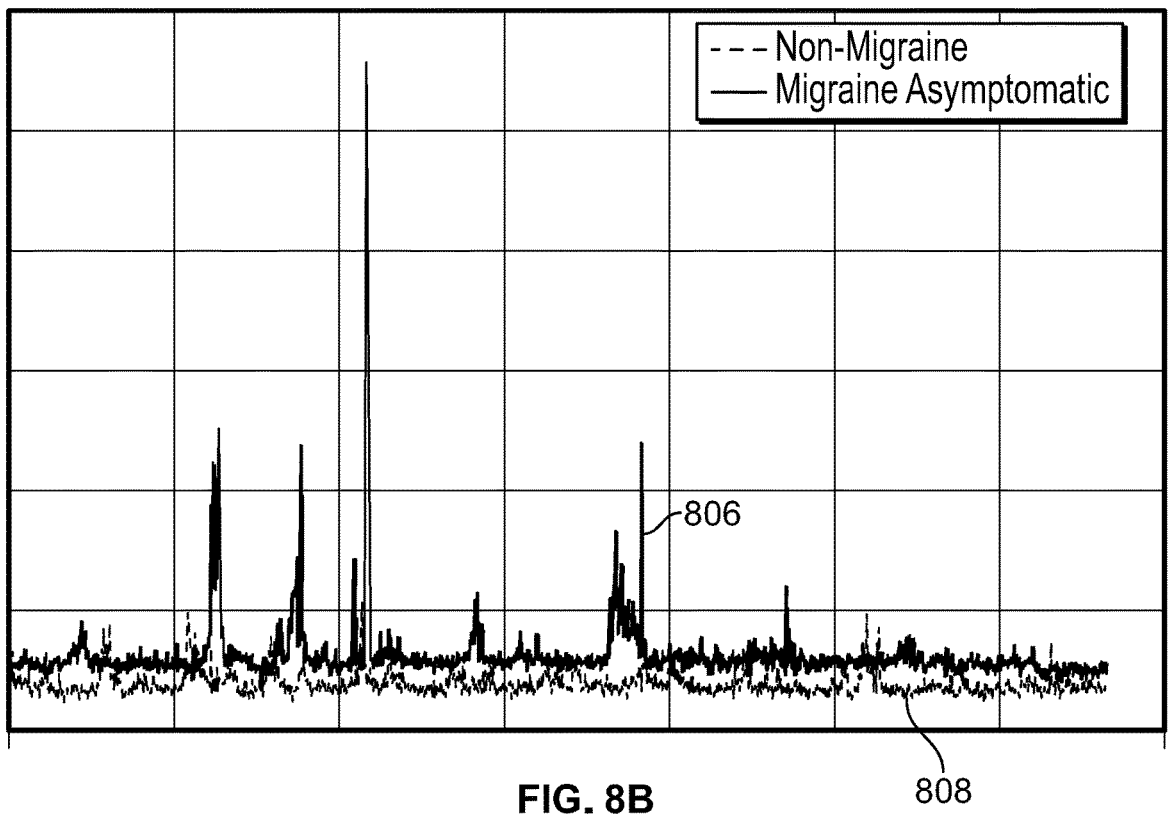
FIG. 8B is a graphical representation of a unique data signature of a person suffering from migraine but not displaying symptoms, in accordance with an embodiment of the present specification.
Figure 8C:
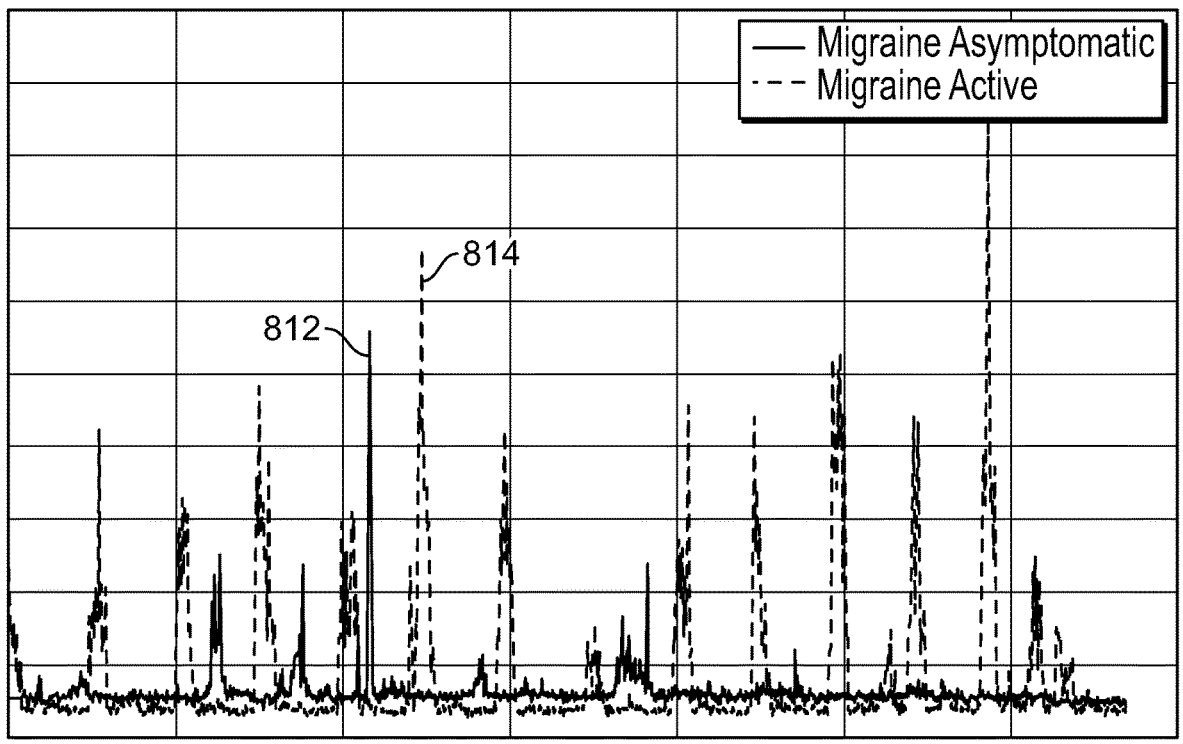
FIG. 8C is a graphical representation of a unique data signature of a person suffering from migraine but not displaying symptoms versus data signature of a person suffering from migraine and also displaying symptoms, in accordance with an embodiment of the present specification.

In an embodiment, the present specification provides unique signatures obtained from recorded vibrations generated from cardiac cycles of patients suffering from migraines, by using the signal analyzer employing AI and deep learning based algorithms. FIG. 8A is a graphical representation of a unique data signature of a person suffering from migraine, in accordance with an embodiment of the present specification. Plot 802 depicts a unique signature obtained from recorded vibrations generated from cardiac cycles of a patient suffering from migraine, while plot 804 depicts data obtained from a person not suffering from migraine. FIG. 8B is a graphical representation of a unique data signature of an asymptomatic migraine patient from migraine but not displaying symptoms, in accordance with an embodiment of the present specification. Plot 806 depicts a unique signature obtained from recorded vibrations generated from cardiac cycles of a patient suffering from migraine but not displaying symptoms (an "asymptomatic migraine patient", as described above), while plot 808 depicts data obtained from a person not suffering from migraine. FIG. 8C is a graphical representation of a unique data signature of a person suffering from migraine but not displaying symptoms versus data signature of a person suffering from migraine and also displaying symptoms, in accordance with an embodiment of the present specification. Plot 812 depicts a unique signature obtained from recorded vibrations generated from cardiac cycles of a patient suffering from migraine but not displaying symptoms, while plot 814 depicts similarly obtained data from a person suffering from migraine and also displaying symptoms of the disease. As can be observed from the plots of FIG. 8C the unique data signatures of asymptomatic migraine patients is different from that of migraine patients displaying symptoms of the disease and can be used to differentiate between the two category of migraine patients while diagnosing said categories of patients.

Figure 8D:
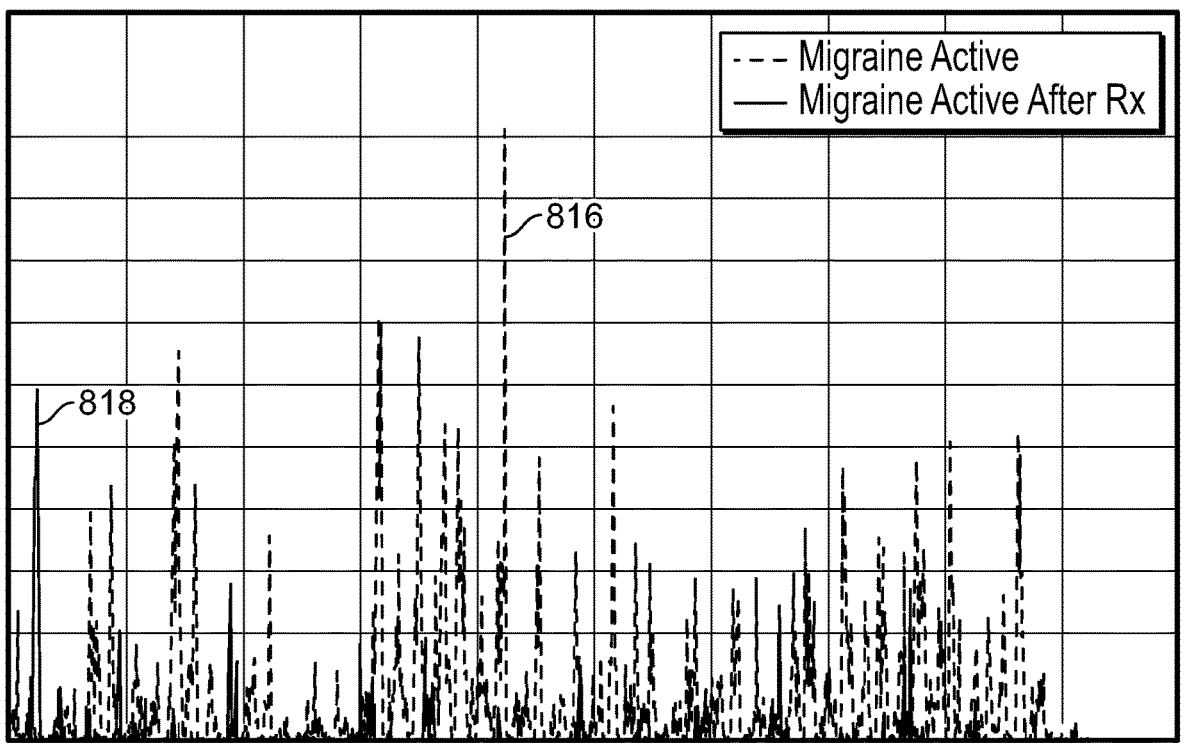
FIG. 8D is a graphical representation of a unique data signature of a person suffering from migraine and displaying symptoms versus data signature the same person after thirty minutes of taking medication for treating migraine, in accordance with an embodiment of the present specification.

FIG. 8D is a graphical representation of a unique data signature of a person suffering from migraine and displaying symptoms versus data signature the same person after thirty minutes of taking medication for treating migraine, in accordance with an embodiment of the present specification. Plot 816 depicts a unique signature obtained from recorded vibrations generated from cardiac cycles of a patient suffering from migraine and displaying symptoms of the disease, while plot 818 depicts unique signature obtained from vibrations generated from cardiac cycles of the same patient recorded thirty minutes after the person has taken medication for treating migraine. As can be observed from the plots of FIG. 8C the unique data signatures of patients before and after taking migraine medication can easily be differentiated by using said data signatures. Hence, the unique data signatures provided by the present specification, in an embodiment, may be used to monitor/compare the effectiveness of different migraine medications and the time taken for the medications to take effect.

Figure 8E:
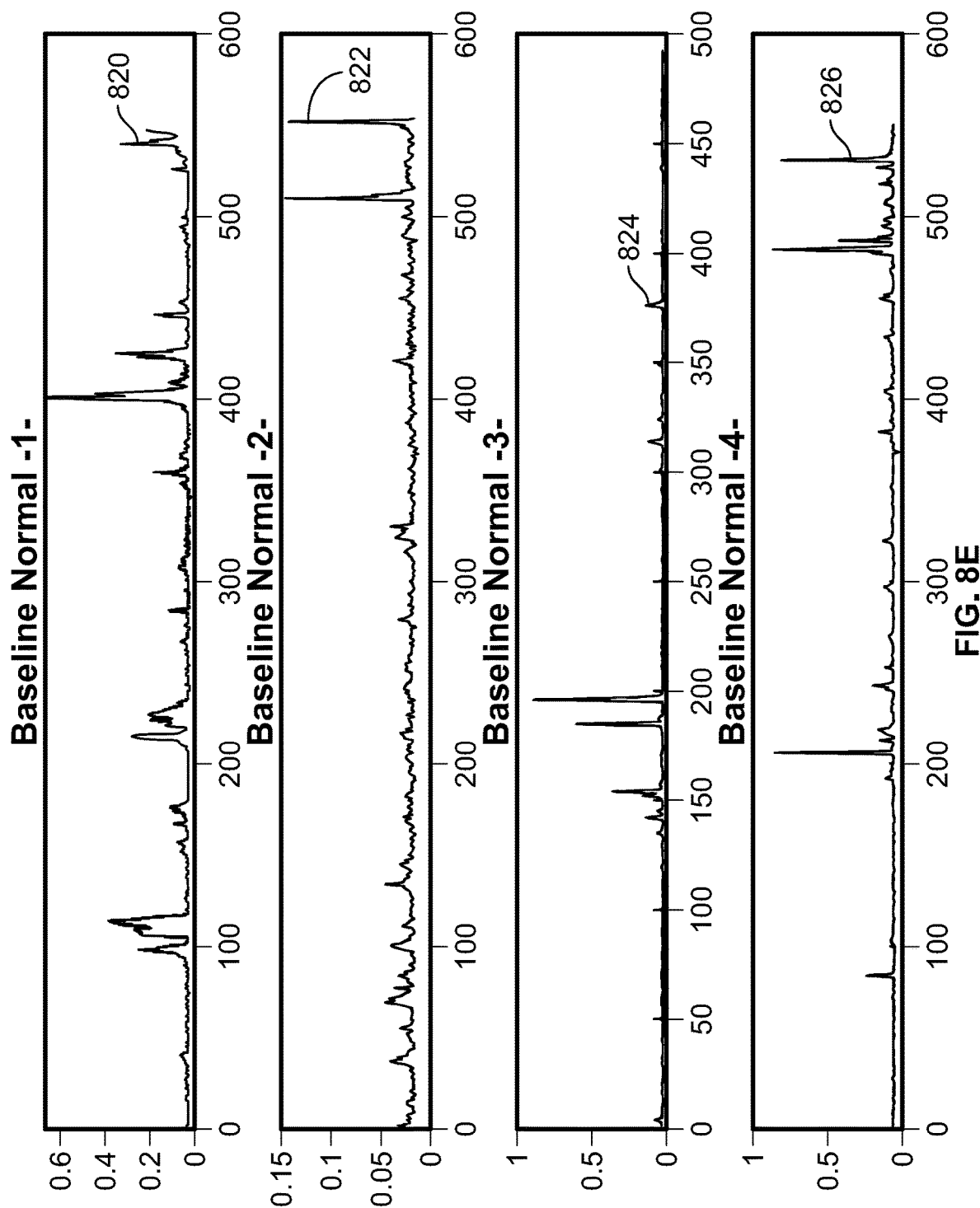
FIG. 8E illustrates graphical representations of unique data signatures of a plurality of normal persons, in accordance with an embodiment of the present specification.
Figure 8F:
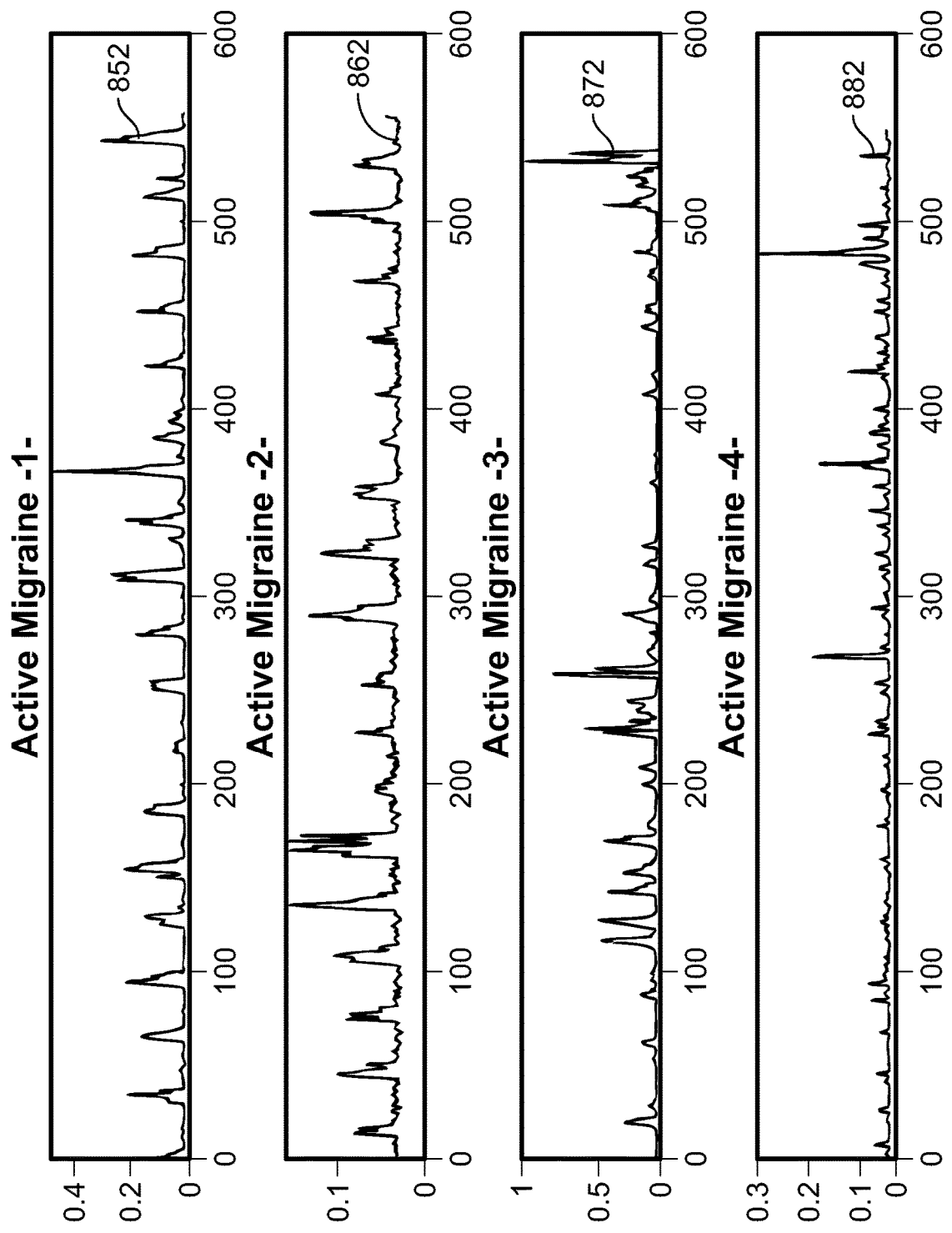
FIG. 8F illustrates graphical representations of unique data signatures of a plurality of persons suffering from migraine, in accordance with an embodiment of the present specification.
Figure 8G:
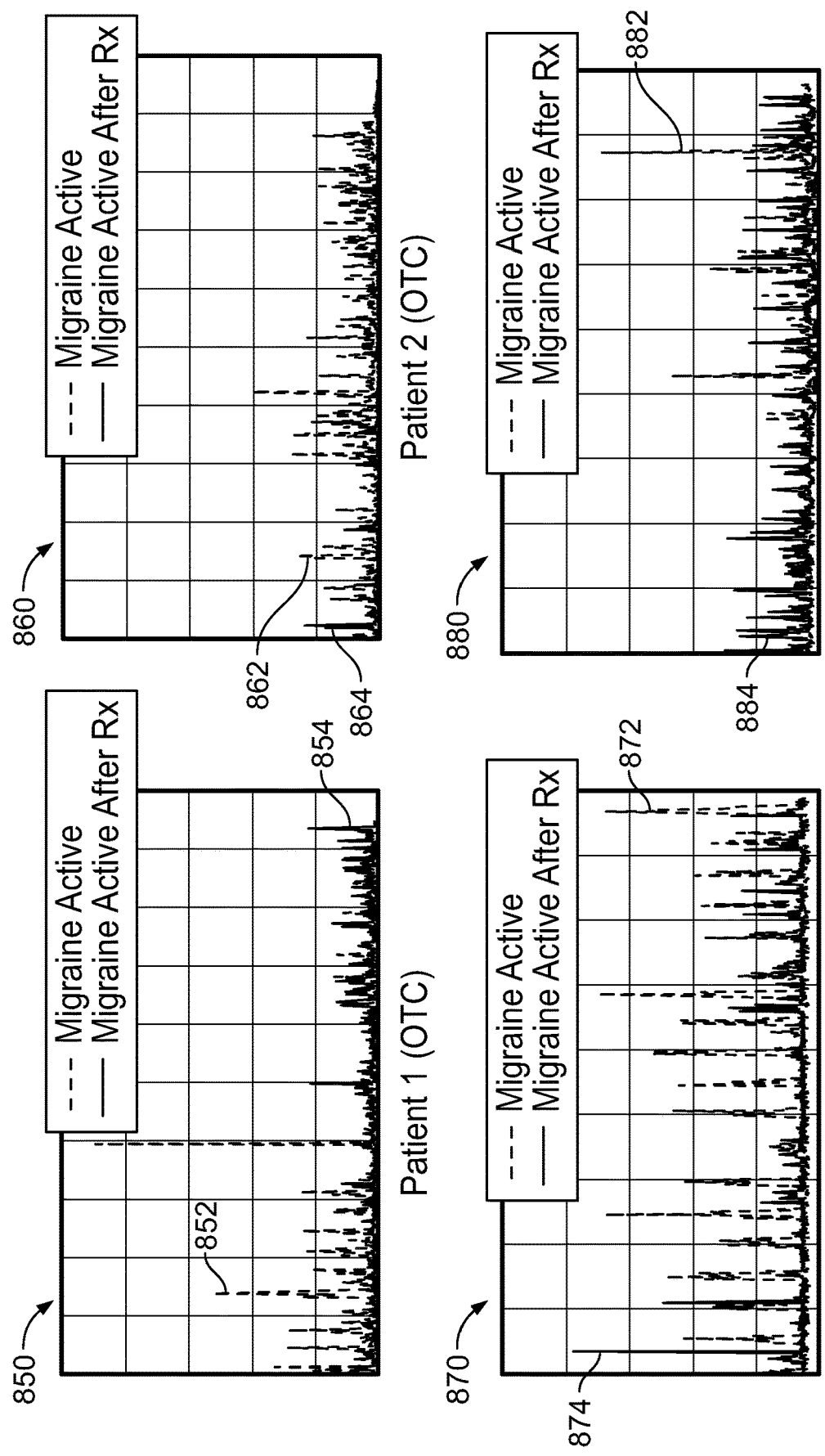
FIG. 8G illustrates graphical representations of unique data signature of a plurality of persons suffering from migraine and displaying symptoms before and after taking medication for treating migraine, in accordance with an embodiment of the present specification.

FIG. 8E illustrates graphical representations of unique data signature of a plurality of persons not suffering from migraine, in accordance with an embodiment of the present specification. Plots 852, 862, 872 and 882 depict unique data signatures obtained from recorded vibrations generated from cardiac cycles of a first, second, third and fourth patient respectively, all not suffering from migraine and displaying no symptoms of the disease. FIG. 8F illustrates graphical representations of unique data signature of a plurality of persons suffering from migraine and displaying symptoms before taking medication for treating migraine, in accordance with an embodiment of the present specification. Plots 852, 862, 872 and 882 depict unique data signatures obtained from recorded vibrations generated from cardiac cycles of a first, second, third and fourth patient respectively, all suffering from migraine and displaying symptoms of the disease. FIG. 8G illustrates graphical representations of unique data signature of a plurality of persons suffering from migraine and displaying symptoms before and after taking medication for treating migraine, in accordance with an embodiment of the present specification. Graphs 850, 860, 870 and 880 illustrate plots 852, 862, 872 and 882 depicting unique data signatures obtained from recorded vibrations generated from cardiac cycles of a first, second, third and fourth patient respectively, all suffering from migraine and displaying symptoms of the disease; and plots 854, 864, 874 and 884 depicting unique signatures obtained from vibrations generated from cardiac cycles of the first, second, third and fourth patients respectively recorded thirty minutes after said persons have taken medication for treating migraine. As can be seen in FIGS. 8E, 8F and 8G, each migraine patient exhibits a unique data signature before and after being treated.

Figure 9:
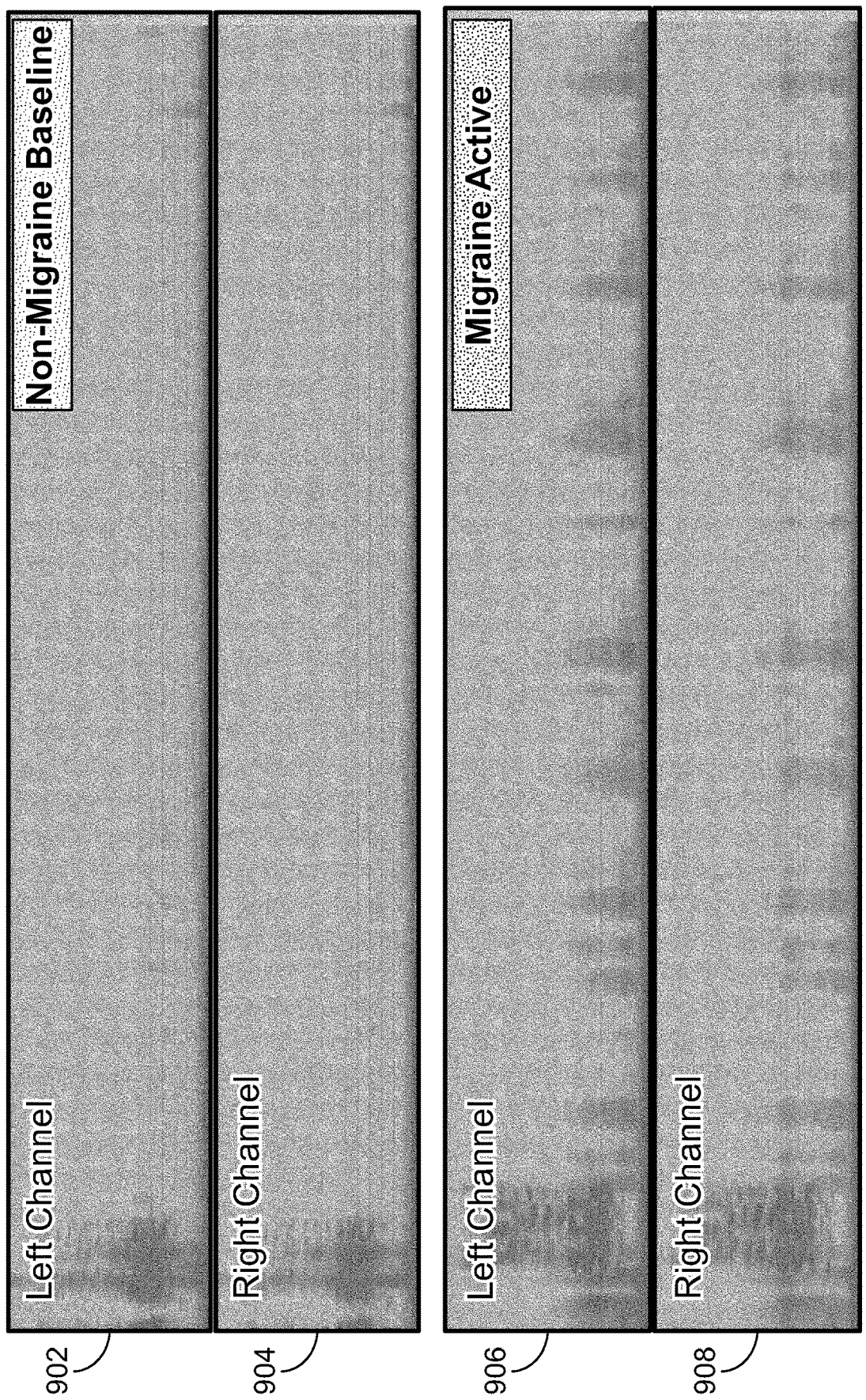
FIG. 9 illustrates graphical representation of two channel audio inputs from a person experiencing migraine symptoms and a person not experiencing migraine symptoms, in accordance with an embodiment of the present specification.

In an embodiment, the present specification provides AI based methods of detection and analysis of human emotion/speech by detecting changes in tone, volume, speed and voice quality; and using said detected speech attributes to determine emotions like anger, joy, pain and laughter. In embodiments, such audio files obtained by detecting and analysis speech of a plurality of persons are recorded in a database and are compared against a patient's audio data to determine if the patient is suffering from one or more predefined pathologies such as migraine by using specialized computing algorithms, as described in the context of the present specification. For example, even if a patient is saying that he is experiencing symptoms of migraine, his speech may be detected and analyzed by using the method of the present specification, and if a emotions of joy and laughter are detected, then it is determined that the patient is not suffering from migraine symptoms. FIG. 9 illustrates graphical representation of two channel audio inputs from a person experiencing migraine symptoms and a person not experiencing migraine symptoms, in accordance with an embodiment of the present specification. Plot 902 and 904 depict the speech of a person not suffering from migraine recorded via a left and right recording channel respectively. Plot 906 and 908 depict the speech of a person suffering from migraine recorded via a left and right recording channel respectively. The plots illustrate the difference between speech data obtained from a person suffering from migraine and the person who is recording the session, demonstrating that speech data may be used for migraine diagnosis. In embodiments, speech data may be obtained from a person suffering from migraine and compared to speech data of another person who is not suffering from migraine, wherein said differences in speech data may be used for migraine diagnosis.

In an embodiment, the diagnostic system of the present specification comprises a facial (emotion) recognition Biometric Artificial Intelligence (BAI) technology for determining and recording a patient's facial expressions which are indicative of the patient's emotions. In an embodiment, the recorded facial expressions are evaluated in conjunction with the patient's response to pre-treatment questionnaire to diagnose the patient's pathological condition. BAI can identify a patient's unique facial patterns based on facial textures and shapes. The facial images recorded by BAI enable the AI based diagnostic algorithm of the present specification to compare selected facial emotional features to those pre-recorded in a database, to enhance the accuracy of the algorithm. In embodiments, BAI based facial expression recognition enables detection of patterns in the recorded facial images that are representative of an active migraine (pain expression) versus an asymptomatic migraine. Hence, the present specification provides an A.I. driven platform for diagnosing migraines, that incorporates EMR/pre-treatment questionnaire, integrated with facial and speech emotional recognition to enhance the algorithm to provide greater accuracy and productiveness.

The diagnostic system and method of the present specification provides numerous benefits and advantages over known migraine assessment approaches. In embodiments, the specification utilizes a passive microphone approach that analyzes signals by an algorithm and classifies them, which allows an objective detection of migraines, non-invasively. Moreover, the low cost non-invasive, acoustic based approach removes the subjective diagnosis of migraines, therefore, enhancing the screening, diagnosis and prescription of drug appropriate forms of therapy. Furthermore, the diagnostic system and method of the present specification can detect a normal condition (not suffering from migraine) from an asymptomatic migraine; an asymptomatic migraine from an active migraine and an active migraine from an active migraine after having received therapy.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A system for diagnosing one or more pathologies in a patient, the system comprising:
   a headset comprising at least one microphone, acoustic sensor, or accelerometer to passively receive vibrations from cerebral vasculature of the patient's brain;
   at least one computing device coupled with the headset for processing the received vibrations to obtain a signal;
   a signal analyzer coupled with the at least one computing device and configured to analyze the signal to identify a pattern indicative of the one or more predefined pathologies, wherein the one or more predefined pathologies comprise at least one of tension headaches, migraines, vascular dementia, Alzheimer's disease, epilepsy, vascular Parkinson's disease, cerebral vasospasm, or meningitis; and a second computing device configured to receive the pattern, compare the pattern to a plurality of predefined patterns indicative of the one or more predefined pathologies, and categorize the pattern as being representative of the one or more predefined pathologies, wherein the plurality of predefined patterns comprises acoustic signal data indicative of a plurality of different migraine types.

2. The system of claim 1 wherein the signal analyzer is configured to differentiate between each of the predefined pathologies and output an audio or visual indicator that specifically identifies one of the predefined pathologies while concurrently excluding a remainder of the predefined pathologies.

3. The system of claim 1 wherein the signal analyzer is not configured to identify a traumatic brain injury, stroke, aneurysm, or hemorrhage.

4. The system of claim 1 wherein the headset comprises two microphones, wherein each of the two microphones is provided within each ear covering of the headset.

5. The system of claim 4, wherein the headset comprises a pre-amplifier, a frequency equalizer and a noise cancellation module.

6. The system of claim 1 wherein the at least one microphone captures and outputs bi-hemispheric data and has an output for detecting vibrations in a range of 0-750 kHz.

7. The system of claim 1 wherein the headset comprises a signal quality indicator configured to indicate a quality of the vibrations being received, a light source configured to visually indicate that the headset is in an operational mode, and a light array configured to indicate a level of battery charge.

8. The system of claim 1 wherein the at least one computing device comprises at least one of an Internet of Things (IoT) device, mobile phone, tablet device, desktop computer or laptop computer.

9. The system of claim 1 wherein the at least one microphone, acoustic sensor, or accelerometer is configured to be positioned within a predefined distance of at least one of the patient's basilar artery, anterior inferior cerebellar artery, anterior vestibular artery, internal auditory artery, common cochlear artery, internal carotid artery, or ophthalmic artery.

10. The system of claim 9 wherein the predefined distance is 10 mm.

11. The system of claim 1 wherein the at least one microphone, acoustic sensor, or accelerometer is configured to be positioned outside of a predefined distance from at least one of the patient's zygoma, external carotid artery, internal maxillary artery, facial artery, or occipital artery.

12. The system of claim 11 wherein the predefined distance is 5 mm.

13. The system of claim 1 wherein the at least one microphone, acoustic sensor, accelerometer is configured to be positioned within a first predefined distance of at least one of the patient's basilar artery, anterior inferior cerebellar artery, anterior vestibular artery, internal auditory artery, common cochlear artery, internal carotid artery, or ophthalmic artery and outside of a second predefined distance from at least one of the patient's zygoma, external carotid artery, internal maxillary artery, facial artery, or occipital artery, wherein the first predefined distance is less than the second predefined distance.

14. The system of claim 13 wherein the first predefined distance is within a range of 0 mm to 5 mm and wherein the second predefined distance is at least 5 mm.

15. The system of claim 1 further comprising one or more databases coupled with the signal analyzer, wherein the one or more databases comprises pre-determined signal classifications comprising specific frequencies, frequency ranges, energies, energy ranges, periodicities or periodicity ranges unique to each of the predefined pathologies.

16. The system of claim 15 wherein the signal analyzer comprises one or more algorithms configured to detect one or more of the predefined pathologies present in the signal by comparing the analyzed signal with the pre-determined signal classifications comprising specific frequencies unique to each of the predefined pathologies.

17. The system of claim 1 wherein the plurality of different migraine types comprise aura, without aura, basilar, hemiplegic, ophthaloplegic, vestibular or chronic.

18. The system of claim 1 wherein the plurality of predefined patterns is derived from signal measurements taken from individuals other than the patient.

19. A method for determining if a patient is suffering from a condition, the method comprising:
    positioning at least one microphone, acoustic sensor, or accelerometer within a first predefined distance of at least one of the patient's basilar artery, anterior inferior cerebellar artery, anterior vestibular artery, internal auditory artery, common cochlear artery, internal carotid artery, or ophthalmic artery and outside of a second predefined distance from at least one of the patient's zygoma, external carotid artery, internal maxillary artery, facial artery, or occipital artery, wherein the first predefined distance is less than the second predefined distance;
    capturing a signal transduced through a medium, wherein the medium is at least one of air, tissue, bone, vasculature, or nerves, wherein the signal is caused by blood flow in a cerebral vasculature of the patient's brain and is not a function of a second signal originating external to the patient, and wherein the signal is captured using at least one of the accelerometer, the acoustic sensor, or the microphone;
    digitizing the captured signal using a first component in data communication with the accelerometer, acoustic sensor, or microphone;
    transmitting the digitized captured signal to a signal analyzer using a second component in data communication with the first component;
    using the signal analyzer, acquiring the digitized captured signal and processing the acquired digitized captured signal to identify a signature, wherein the signature is a function of a non-zero amplitude, frequency and periodicity of the signal, wherein the signature is uniquely indicative of the condition, and wherein the condition is one of a tension headache, a migraine, vascular dementia, Alzheimer's disease, epilepsy, vascular Parkinson's disease, cerebral vasospasm or meningitis; and
    using a computing device, receiving the signature, comparing the signature to one of a plurality of predefined patterns indicative of the condition, and categorizing the signature as being representative of the condition, wherein the plurality of predefined patterns includes acoustic signal data indicative of a plurality of different migraine types.

20. The method of claim 19 wherein the first predefined distance is within a range of 0 mm to 5 mm and wherein the second predefined distance is at least 5 mm.

21. The method of claim 19 further comprising accessing one or more databases, wherein the one or more databases comprises pre-determined signal classifications comprising specific frequencies, frequency ranges, energies, energy ranges, periodicities or periodicity ranges unique to the condition.

22. The method of claim 19 wherein the signal analyzer comprises one or more algorithms configured to detect data indicative of the condition present in the signal by comparing the signal with pre-determined signal classifications comprising specific frequencies unique to the condition.

23. The method of claim 19 wherein the plurality of different migraine types comprise aura, without aura, basilar, hemiplegic, ophthaloplegic, vestibular or chronic.

24. The method of claim 19 wherein the plurality of predefined patterns is derived from signal measurements taken from individuals other than the patient.

* * * * *